US012622803B2

(12) United States Patent
Sweeney

(10) Patent No.: US 12,622,803 B2
(45) Date of Patent: May 12, 2026

(54) FLUID COLLECTION DEVICES, SYSTEMS, AND METHODS

(71) Applicant: PUREWICK CORPORATION, El Cajon, CA (US)

(72) Inventor: Lyndsay Alison Sweeney, Decatur, GA (US)

(73) Assignee: PUREWICK CORPORATION, Covington, GA (US)

( * ) Notice: Subject to any disclaimer, the term of this patent is extended or adjusted under 35 U.S.C. 154(b) by 1324 days.

(21) Appl. No.: 17/051,600

(22) PCT Filed: Apr. 29, 2019

(86) PCT No.: PCT/US2019/029616
§ 371 (c)(1),
(2) Date: Oct. 29, 2020

(87) PCT Pub. No.: WO2019/212956
PCT Pub. Date: Nov. 7, 2019

(65) Prior Publication Data
US 2021/0236324 A1 Aug. 5, 2021

Related U.S. Application Data

(60) Provisional application No. 62/665,711, filed on May 2, 2018.

(51) Int. Cl.
*A61F 5/455* (2006.01)
*A61F 5/44* (2006.01)

(52) U.S. Cl.
CPC ............ *A61F 5/455* (2013.01); *A61F 5/4401* (2013.01)

(58) Field of Classification Search
CPC ........ A61F 5/455; A61F 5/4401; A61F 5/451; A61F 5/453; A61F 5/44; A61F 5/4404
See application file for complete search history.

(56) References Cited

U.S. PATENT DOCUMENTS 737,443 A 8/1903 Mooers
1,015,905 A 1/1912 Northrop
(Continued)

FOREIGN PATENT DOCUMENTS

AU 2018216821 A1 8/2019
AU 2021299304 A1 2/2023
(Continued)

OTHER PUBLICATIONS

US 9,908,683 B2, 03/2018, Sandhausen et al. (withdrawn)
(Continued)

*Primary Examiner* — Rebecca E Eisenberg
*Assistant Examiner* — Ted Yang
(74) *Attorney, Agent, or Firm* — Ballard Spahr LLP

(57) ABSTRACT

Example fluid collection devices and methods of assembling the fluid collection devices. The fluid collection devices include a fluid impermeable barrier and a fluid permeable body. The fluid impermeable barrier at least partially defines a chamber and includes an opening extending therethrough. The opening is configured to be positioned adjacent to or receive therein a urethra of a subject. The fluid permeable body has a singular porous material in a substantially cylindrical shape and positioned at least partially within the chamber.

7 Claims, 11 Drawing Sheets

(56) References Cited

U.S. PATENT DOCUMENTS

| | | | |
|---|---|---|---|
| 1,032,841 A | 7/1912 | Koenig | |
| 1,178,644 A | 4/1916 | Johnson | |
| 1,387,726 A | 8/1921 | Karge | |
| 1,742,080 A | 12/1929 | Jones | |
| 1,979,899 A | 11/1934 | Obrien et al. | |
| 2,241,010 A | 5/1941 | Chipley | |
| 2,262,772 A | 11/1941 | Peder | |
| 2,326,881 A | 8/1943 | Packer | |
| 2,379,346 A | 6/1945 | Farrell | |
| 2,485,555 A | 10/1949 | Bester | |
| 2,571,357 A | 10/1951 | Charles | |
| 2,613,670 A | 10/1952 | Edward | |
| 2,616,426 A | 11/1952 | Adele | |
| 2,644,234 A | 7/1953 | Earl | |
| 2,648,335 A | 8/1953 | Chambers | |
| 2,859,786 A | 11/1958 | Tupper | |
| 2,944,551 A | 7/1960 | Carl | |
| 2,968,046 A | 1/1961 | Duke | |
| 2,971,512 A | 2/1961 | Reinhardt | |
| 3,032,038 A | 5/1962 | Swinn | |
| 3,077,883 A | 2/1963 | Hill | |
| 3,087,938 A | 4/1963 | Hans et al. | |
| 3,114,916 A | 12/1963 | Hadley | |
| 3,169,528 A | 2/1965 | Knox et al. | |
| 3,171,506 A | 3/1965 | Therkel | |
| 3,175,719 A | 3/1965 | Herndon | |
| 3,194,238 A | 7/1965 | Breece | |
| 3,198,994 A | 8/1965 | Hildebrandt et al. | |
| 3,221,742 A | 12/1965 | Egon | |
| 3,312,221 A | 4/1967 | Overment | |
| 3,312,981 A | 4/1967 | Mcguire et al. | |
| 3,349,768 A | 10/1967 | Keane | |
| 3,362,590 A | 1/1968 | Gene | |
| 3,366,116 A | 1/1968 | Huck | |
| 3,398,848 A | 8/1968 | Donovan | |
| 3,400,717 A | 9/1968 | Bruce et al. | |
| 3,406,688 A | 10/1968 | Bruce | |
| 3,424,163 A | 1/1969 | Gravdahl | |
| 3,425,471 A | 2/1969 | Yates | |
| 3,434,565 A | 3/1969 | Fischer | |
| 3,511,241 A | 5/1970 | Lee | |
| 3,512,185 A | 5/1970 | Ellis | |
| 3,520,300 A | 7/1970 | Flower | |
| 3,528,423 A | 9/1970 | Lee | |
| 3,608,552 A | 9/1971 | Broerman | |
| 3,613,123 A | 10/1971 | Langstrom | |
| 3,648,700 A | 3/1972 | Warner | |
| 3,651,810 A | 3/1972 | Ormerod | |
| 3,661,155 A | 5/1972 | Lindan | |
| 3,683,918 A | 8/1972 | Pizzella | |
| 3,699,815 A | 10/1972 | Holbrook | |
| 3,726,277 A | 4/1973 | Hirschman | |
| 3,742,952 A | 7/1973 | Magers et al. | |
| 3,757,355 A | 9/1973 | Allen et al. | |
| 3,788,324 A | 1/1974 | Lim | |
| 3,843,016 A | 10/1974 | Bornhorst et al. | |
| 3,863,638 A | 2/1975 | Rogers et al. | |
| 3,863,798 A | 2/1975 | Kurihara et al. | |
| 3,864,759 A | 2/1975 | Horiuchi | |
| 3,865,109 A | 2/1975 | Elmore et al. | |
| 3,881,486 A | 5/1975 | Fenton | |
| 3,881,489 A | 5/1975 | Hartwell | |
| 3,915,189 A | 10/1975 | Holbrook et al. | |
| 3,931,650 A | 1/1976 | Miller | |
| 3,998,228 A | 12/1976 | Poidomani | |
| 3,999,550 A | 12/1976 | Martin | |
| 4,006,793 A | 2/1977 | Robinson | |
| 4,015,604 A | 4/1977 | Csillag | |
| 4,020,843 A | 5/1977 | Kanall | |
| 4,022,213 A | 5/1977 | Stein | |
| 4,027,776 A | 6/1977 | Douglas | |
| 4,031,897 A | 6/1977 | Graetz | |
| 4,064,962 A | 12/1977 | Hunt | |
| 4,069,817 A | 1/1978 | Fenole et al. | |
| 4,084,589 A | 4/1978 | Kulvi | |
| 4,096,897 A | 6/1978 | Cammarata | |
| 4,116,197 A | 9/1978 | Bermingham | |
| 4,180,178 A | 12/1979 | Turner | |
| 4,187,953 A | 2/1980 | Turner | |
| 4,194,508 A | 3/1980 | Anderson | |
| 4,200,102 A | 4/1980 | Duhamel et al. | |
| 4,202,058 A | 5/1980 | Anderson | |
| 4,203,503 A | 5/1980 | Bertotti et al. | |
| 4,209,076 A | 6/1980 | Bertotti et al. | |
| 4,223,677 A | 9/1980 | Anderson | |
| 4,233,025 A | 11/1980 | Larson et al. | |
| 4,233,978 A | 11/1980 | Hickey | |
| 4,246,901 A * | 1/1981 | Frosch | A61F 5/455 |
| | | | 4/144.3 |
| 4,253,542 A | 3/1981 | Ruspa et al. | |
| 4,257,418 A * | 3/1981 | Hessner | A61F 13/51121 |
| | | | 604/397 |
| 4,270,539 A | 6/1981 | Frosch et al. | |
| 4,280,498 A | 7/1981 | Jensen | |
| 4,281,655 A | 8/1981 | Terauchi | |
| 4,292,916 A | 10/1981 | Bradley et al. | |
| 4,330,239 A | 5/1982 | Gannaway | |
| 4,345,341 A | 8/1982 | Saito | |
| 4,349,029 A | 9/1982 | Mott | |
| 4,352,356 A | 10/1982 | Tong | |
| 4,360,933 A | 11/1982 | Kimura et al. | |
| 4,365,363 A | 12/1982 | Windauer | |
| 4,375,841 A | 3/1983 | Vielbig | |
| 4,387,726 A | 6/1983 | Denard | |
| 4,403,991 A | 9/1983 | Hill | |
| 4,421,511 A | 12/1983 | Steer et al. | |
| 4,425,130 A | 1/1984 | Desmarais | |
| 4,446,986 A | 5/1984 | Bowen et al. | |
| 4,453,938 A | 6/1984 | Brendling | |
| 4,457,314 A | 7/1984 | Knowles | |
| 4,476,879 A | 10/1984 | Jackson | |
| 4,526,688 A | 7/1985 | Schmidt et al. | |
| 4,528,703 A | 7/1985 | Kraus | |
| 4,533,354 A | 8/1985 | Jensen et al. | |
| 4,533,357 A | 8/1985 | Hall | |
| D280,438 S | 9/1985 | Wendt | |
| 4,551,141 A | 11/1985 | Mcneil | |
| 4,553,968 A * | 11/1985 | Komis | A41B 9/023 |
| | | | 604/351 |
| 4,568,341 A * | 2/1986 | Mitchell | A61F 13/15699 |
| | | | 604/378 |
| 4,581,026 A | 4/1986 | Schneider | |
| 4,583,983 A | 4/1986 | Einhorn et al. | |
| 4,589,516 A | 5/1986 | Inoue et al. | |
| 4,601,716 A | 7/1986 | Smith | |
| 4,610,675 A * | 9/1986 | Triunfol | A61F 5/455 |
| | | | 4/144.3 |
| 4,620,333 A | 11/1986 | Ritter | |
| 4,626,250 A | 12/1986 | Schneider | |
| 4,627,846 A | 12/1986 | Ternstroem | |
| 4,631,061 A * | 12/1986 | Martin | A61F 5/451 |
| | | | 604/323 |
| 4,650,477 A | 3/1987 | Johnson | |
| 4,655,754 A | 4/1987 | Richmond et al. | |
| 4,656,675 A | 4/1987 | Fajnsztajn | |
| 4,681,570 A | 7/1987 | Dalton | |
| 4,681,572 A | 7/1987 | Tokarz et al. | |
| 4,681,577 A * | 7/1987 | Stern | A61F 13/47 |
| | | | D24/126 |
| 4,692,160 A | 9/1987 | Nussbaumer | |
| 4,707,864 A * | 11/1987 | Ikematsu | A61G 9/006 |
| | | | 4/144.3 |
| 4,713,065 A | 12/1987 | Koot | |
| 4,713,066 A | 12/1987 | Komis | |
| 4,723,953 A | 2/1988 | Pratt et al. | |
| 4,735,841 A | 4/1988 | Sourdet | |
| 4,743,236 A | 5/1988 | Manschot | |
| 4,747,166 A * | 5/1988 | Kuntz | A61F 5/455 |
| | | | 4/144.1 |
| 4,752,944 A | 6/1988 | Conrads et al. | |
| 4,769,215 A | 9/1988 | Ehrenkranz | |
| 4,771,484 A | 9/1988 | Mozell | |
| 4,772,280 A | 9/1988 | Rooyakkers | |

(56)                    References Cited

U.S. PATENT DOCUMENTS

| | | | |
|---|---|---|---|
| 4,784,654 A | 11/1988 | Beecher | |
| 4,790,830 A | 12/1988 | Hamacher | |
| 4,790,835 A | 12/1988 | Elias | |
| 4,791,686 A | 12/1988 | Taniguchi et al. | |
| 4,795,449 A | 1/1989 | Schneider et al. | |
| 4,798,603 A | 1/1989 | Meyer et al. | |
| 4,799,928 A | 1/1989 | Crowley | |
| 4,804,377 A | 2/1989 | Hanifl et al. | |
| 4,812,053 A | 3/1989 | Bhattacharjee | |
| 4,813,943 A * | 3/1989 | Smith | A61F 5/4408 |
| | | | 604/350 |
| 4,820,291 A | 4/1989 | Terauchi et al. | |
| 4,820,297 A | 4/1989 | Kaufman et al. | |
| 4,841,728 A | 6/1989 | Jean et al. | |
| 4,846,818 A | 7/1989 | Keldahl et al. | |
| 4,846,819 A | 7/1989 | Welch | |
| 4,846,824 A | 7/1989 | Schultz et al. | |
| 4,846,909 A | 7/1989 | Klug et al. | |
| 4,865,595 A | 9/1989 | Heyden | |
| 4,880,417 A | 11/1989 | Yabrov et al. | |
| 4,882,794 A | 11/1989 | Stewart | |
| 4,883,465 A | 11/1989 | Brennan | |
| 4,886,498 A | 12/1989 | Newton | |
| 4,886,508 A * | 12/1989 | Washington | A61F 5/455 |
| | | | 604/347 |
| 4,886,509 A | 12/1989 | Mattsson | |
| 4,889,532 A | 12/1989 | Metz et al. | |
| 4,889,533 A | 12/1989 | Beecher | |
| 4,890,691 A | 1/1990 | Ching-Ho | |
| 4,895,140 A | 1/1990 | Bellak | |
| 4,903,254 A | 2/1990 | Haas | |
| 4,904,248 A * | 2/1990 | Vaillancourt | A61F 5/455 |
| | | | 604/327 |
| 4,905,692 A * | 3/1990 | More | D04B 1/18 |
| | | | 606/151 |
| 4,911,262 A | 3/1990 | Tani et al. | |
| 4,930,997 A | 6/1990 | Bennett | |
| 4,936,838 A | 6/1990 | Cross et al. | |
| 4,950,262 A | 8/1990 | Takagi | |
| 4,955,922 A | 9/1990 | Terauchi | |
| 4,957,487 A | 9/1990 | Gerow | |
| 4,965,460 A | 10/1990 | Tanaka et al. | |
| 4,986,823 A | 1/1991 | Anderson et al. | |
| 4,987,849 A | 1/1991 | Sherman | |
| 5,002,541 A * | 3/1991 | Conkling | A61F 5/44 |
| | | | 604/324 |
| 5,004,463 A | 4/1991 | Nigay | |
| 5,013,308 A | 5/1991 | Sullivan et al. | |
| 5,031,248 A * | 7/1991 | Kemper | A41B 9/008 |
| | | | 2/400 |
| 5,045,077 A | 9/1991 | Blake | |
| 5,045,283 A | 9/1991 | Patel | |
| 5,049,144 A | 9/1991 | Payton | |
| 5,053,339 A | 10/1991 | Patel | |
| 5,057,092 A | 10/1991 | Webster | |
| 5,058,088 A | 10/1991 | Haas et al. | |
| 5,071,347 A | 12/1991 | Mcguire | |
| 5,078,707 A | 1/1992 | Peter | |
| 5,084,037 A | 1/1992 | Barnett | |
| 5,100,396 A | 3/1992 | Zamierowski | |
| 5,102,404 A | 4/1992 | Goldberg et al. | |
| 5,112,324 A | 5/1992 | Wallace | |
| 5,137,033 A | 8/1992 | Norton | |
| 5,147,301 A | 9/1992 | Ruvio | |
| 5,176,667 A | 1/1993 | Debring | |
| 5,195,997 A * | 3/1993 | Carns | A61F 5/455 |
| | | | 604/347 |
| 5,196,654 A | 3/1993 | Diflora et al. | |
| 5,199,444 A | 4/1993 | Wheeler | |
| 5,203,699 A | 4/1993 | Mcguire | |
| 5,244,458 A | 9/1993 | Takasu | |
| 5,246,454 A | 9/1993 | Peterson | |
| 5,267,988 A * | 12/1993 | Farkas | A47K 11/12 |
| | | | 4/144.3 |
| 5,275,307 A | 1/1994 | Freese | |
| 5,282,795 A | 2/1994 | Finney | |
| 5,294,983 A | 3/1994 | Ersoz et al. | |
| 5,295,979 A | 3/1994 | Delaurentis et al. | |
| 5,295,983 A * | 3/1994 | Kubo | A61F 5/455 |
| | | | 4/144.3 |
| 5,300,052 A | 4/1994 | Kubo | |
| 5,304,749 A | 4/1994 | Crandell | |
| 5,312,383 A | 5/1994 | Kubalak | |
| 5,318,550 A | 6/1994 | Cermak et al. | |
| 5,330,457 A * | 7/1994 | Cohen | A61F 5/4401 |
| | | | 604/358 |
| 5,330,459 A | 7/1994 | Lavon et al. | |
| 5,334,174 A | 8/1994 | Street | |
| 5,334,176 A | 8/1994 | Buenger et al. | |
| 5,340,840 A | 8/1994 | Park et al. | |
| 5,382,244 A | 1/1995 | Telang | |
| 5,397,315 A | 3/1995 | Schmidt et al. | |
| 5,409,014 A | 4/1995 | Napoli et al. | |
| 5,409,475 A | 4/1995 | Steer | |
| 5,411,495 A * | 5/1995 | Willingham | A61F 5/455 |
| | | | 600/584 |
| 5,423,784 A | 6/1995 | Metz | |
| 5,423,788 A * | 6/1995 | Rollins | A61F 13/536 |
| | | | 604/378 |
| 5,437,836 A | 8/1995 | Yamada | |
| 5,456,246 A | 10/1995 | Schmieding et al. | |
| 5,466,229 A | 11/1995 | Elson et al. | |
| 5,478,334 A | 12/1995 | Bernstein | |
| 5,499,977 A | 3/1996 | Marx | |
| 5,543,042 A | 8/1996 | Filan et al. | |
| D373,928 S | 9/1996 | Green | |
| 5,582,604 A | 12/1996 | Ahr et al. | |
| 5,592,950 A | 1/1997 | Kopelowicz | |
| 5,593,389 A | 1/1997 | Chang | |
| 5,605,161 A | 2/1997 | Cross | |
| 5,614,699 A | 3/1997 | Yashiro et al. | |
| 5,618,277 A | 4/1997 | Goulter | |
| 5,628,735 A | 5/1997 | Skow | |
| 5,632,736 A | 5/1997 | Block | |
| 5,636,643 A | 6/1997 | Argenta et al. | |
| 5,637,104 A | 6/1997 | Ball et al. | |
| 5,662,633 A | 9/1997 | Doak et al. | |
| 5,674,212 A | 10/1997 | Osborn et al. | |
| 5,678,564 A * | 10/1997 | Lawrence | A61F 5/455 |
| | | | 600/573 |
| 5,678,654 A | 10/1997 | Uzawa | |
| 5,681,297 A | 10/1997 | Hashimoto et al. | |
| 5,687,429 A | 11/1997 | Rahlff | |
| 5,695,485 A | 12/1997 | Duperret et al. | |
| 5,700,254 A | 12/1997 | Mcdowall et al. | |
| 5,701,612 A | 12/1997 | Daneshvar | |
| 5,705,777 A | 1/1998 | Flanigan et al. | |
| 5,735,835 A | 4/1998 | Holland | |
| 5,752,944 A | 5/1998 | Dann et al. | |
| 5,763,333 A | 6/1998 | Suzuki et al. | |
| 5,772,644 A | 6/1998 | Bark et al. | |
| 5,792,132 A | 8/1998 | Garcia | |
| 5,827,243 A | 10/1998 | Palestrant | |
| 5,827,247 A | 10/1998 | Kay | |
| 5,827,250 A | 10/1998 | Fujioka et al. | |
| 5,827,257 A | 10/1998 | Fujioka et al. | |
| D401,699 S | 11/1998 | Herchenbach et al. | |
| 5,859,393 A | 1/1999 | Cummins et al. | |
| 5,865,378 A | 2/1999 | Hollinshead et al. | |
| 5,873,869 A | 2/1999 | Hammons et al. | |
| 5,876,393 A | 3/1999 | Ahr et al. | |
| 5,887,291 A | 3/1999 | Bellizzi | |
| 5,891,125 A | 4/1999 | Plumley | |
| 5,894,608 A | 4/1999 | Birbara | |
| 5,895,349 A | 4/1999 | Tihon | |
| D409,303 S | 5/1999 | Oepping | |
| 5,911,222 A | 6/1999 | Lawrence et al. | |
| 5,956,782 A | 9/1999 | Olguin | |
| 5,957,904 A * | 9/1999 | Holland | A61F 5/455 |
| | | | 604/352 |
| 5,968,026 A | 10/1999 | Osborn et al. | |
| 5,972,505 A | 10/1999 | Phillips et al. | |
| 6,007,526 A | 12/1999 | Passalaqua et al. | |

(56) References Cited

U.S. PATENT DOCUMENTS

| | | | |
|---|---|---|---|
| 6,039,060 | A | 3/2000 | Rower |
| 6,050,983 | A | 4/2000 | Moore et al. |
| 6,059,762 | A | 5/2000 | Boyer et al. |
| 6,063,064 | A | 5/2000 | Tuckey et al. |
| 6,098,625 | A | 8/2000 | Winkler |
| 6,105,174 | A | 8/2000 | Karlsten et al. |
| 6,113,582 | A | 9/2000 | Dwork |
| 6,117,163 | A | 9/2000 | Bierman |
| 6,123,398 | A | 9/2000 | Arai et al. |
| 6,129,718 | A | 10/2000 | Wada et al. |
| 6,131,964 | A | 10/2000 | Sareshwala |
| 6,152,902 | A | 11/2000 | Christian et al. |
| 6,164,569 | A | 12/2000 | Hollinshead et al. |
| 6,177,606 | B1 | 1/2001 | Etheredge et al. |
| 6,209,142 | B1 | 4/2001 | Mattsson et al. |
| 6,220,050 | B1 | 4/2001 | Cooksey |
| 6,244,311 | B1 | 6/2001 | Hand et al. |
| 6,248,096 | B1 | 6/2001 | Dwork et al. |
| 6,263,887 | B1 | 7/2001 | Dunn |
| 6,283,246 | B1 | 9/2001 | Nishikawa |
| 6,296,627 | B1 | 10/2001 | Edwards |
| 6,311,339 | B1 | 11/2001 | Kraus |
| 6,316,688 | B1 | 11/2001 | Hammons et al. |
| 6,336,919 | B1 | 1/2002 | Davis et al. |
| 6,338,729 | B1 | 1/2002 | Wada et al. |
| 6,352,525 | B1 | 3/2002 | Wakabayashi |
| 6,394,988 | B1 | 5/2002 | Hashimoto |
| 6,395,956 | B1 | 5/2002 | Glasgow et al. |
| 6,398,742 | B1 | 6/2002 | Kim |
| 6,406,463 | B1 | 6/2002 | Brown |
| 6,409,712 | B1 | 6/2002 | Dutari et al. |
| 6,415,888 | B2 | 7/2002 | An et al. |
| 6,416,500 | B1 | 7/2002 | Wada et al. |
| 6,423,045 | B1 | 7/2002 | Wise et al. |
| 6,428,521 | B1 | 8/2002 | Droll |
| 6,428,522 | B1 | 8/2002 | Dipalma et al. |
| 6,446,454 | B1 | 9/2002 | Lee et al. |
| 6,461,340 | B1 | 10/2002 | Lenker et al. |
| 6,467,570 | B1 | 10/2002 | Herold |
| 6,475,198 | B1 | 11/2002 | Lipman et al. |
| 6,479,726 | B1 | 11/2002 | Cole et al. |
| 6,491,673 | B1 | 12/2002 | Palumbo et al. |
| 6,508,794 | B1 | 1/2003 | Palumbo et al. |
| 6,524,292 | B1 | 2/2003 | Dipalma et al. |
| 6,540,729 | B1 | 4/2003 | Wada et al. |
| 6,547,771 | B2 | 4/2003 | Robertson et al. |
| 6,551,293 | B1 | 4/2003 | Mitchell |
| 6,569,133 | B2 | 5/2003 | Cheng et al. |
| D476,518 | S | 7/2003 | Doppelt |
| 6,592,560 | B2 | 7/2003 | Snyder et al. |
| 6,610,038 | B1 | 8/2003 | Dipalma et al. |
| 6,618,868 | B2 | 9/2003 | Minnick |
| 6,620,142 | B1 | 9/2003 | Flueckiger |
| 6,629,651 | B1 | 10/2003 | Male et al. |
| 6,635,037 | B1 | 10/2003 | Bennett |
| 6,635,038 | B2 | 10/2003 | Scovel |
| 6,652,495 | B1 | 11/2003 | Walker |
| 6,666,850 | B1 | 12/2003 | Ahr et al. |
| 6,685,684 | B1 | 2/2004 | Falconer |
| 6,695,828 | B1 | 2/2004 | Dipalma et al. |
| 6,699,174 | B1 | 3/2004 | Bennett |
| 6,700,034 | B1 | 3/2004 | Lindsay et al. |
| 6,702,793 | B1 | 3/2004 | Sweetser et al. |
| 6,706,027 | B2 | 3/2004 | Harvie et al. |
| 6,732,384 | B2 | 5/2004 | Scott |
| 6,736,977 | B1 | 5/2004 | Hall et al. |
| 6,740,066 | B2 | 5/2004 | Wolff et al. |
| 6,764,477 | B1 | 7/2004 | Chen et al. |
| 6,783,519 | B2 | 8/2004 | Samuelsson |
| 6,796,974 | B2 | 9/2004 | Palumbo et al. |
| 6,814,547 | B2 | 11/2004 | Childers et al. |
| 6,849,065 | B2 | 2/2005 | Schmidt et al. |
| 6,857,137 | B2 | 2/2005 | Otto |
| 6,885,690 | B2 | 4/2005 | Aggerstam et al. |
| 6,888,044 | B2 | 5/2005 | Fell et al. |
| 6,893,425 | B2 | 5/2005 | Dunn et al. |
| 6,912,737 | B2 | 7/2005 | Ernest et al. |
| 6,918,899 | B2 | 7/2005 | Harvie |
| 6,979,324 | B2 | 12/2005 | Bybordi et al. |
| 7,018,366 | B2 | 3/2006 | Easter |
| 7,066,411 | B2 | 6/2006 | Male et al. |
| 7,122,023 | B1 | 10/2006 | Hinoki |
| 7,125,399 | B2 | 10/2006 | Miskie |
| 7,131,964 | B2 | 11/2006 | Harvie |
| 7,135,012 | B2 | 11/2006 | Harvie |
| 7,141,043 | B2 | 11/2006 | Harvie |
| D533,972 | S | 12/2006 | La |
| 7,160,273 | B2 | 1/2007 | Greter et al. |
| 7,166,092 | B2 | 1/2007 | Elson et al. |
| 7,171,699 | B2 | 2/2007 | Ernest et al. |
| 7,171,871 | B2 | 2/2007 | Kozak |
| 7,179,951 | B2 | 2/2007 | Krishnaswamy-mirle et al. |
| 7,181,781 | B1 | 2/2007 | Trabold et al. |
| 7,186,245 | B1 | 3/2007 | Cheng et al. |
| 7,192,424 | B2 | 3/2007 | Cooper |
| 7,219,764 | B1 | 5/2007 | Forbes |
| 7,220,250 | B2 | 5/2007 | Suzuki et al. |
| D562,975 | S | 2/2008 | Otto |
| 7,335,189 | B2 | 2/2008 | Harvie |
| 7,358,282 | B2 | 4/2008 | Krueger et al. |
| 7,390,320 | B2 | 6/2008 | Machida et al. |
| 7,438,706 | B2 | 10/2008 | Koizumi et al. |
| 7,488,310 | B2 | 2/2009 | Yang |
| 7,491,194 | B1 | 2/2009 | Oliwa |
| D591,106 | S | 4/2009 | Dominique et al. |
| 7,513,381 | B2 | 4/2009 | Heng et al. |
| 7,520,872 | B2 | 4/2009 | Biggie et al. |
| D593,801 | S | 6/2009 | Wilson et al. |
| 7,540,364 | B2 | 6/2009 | Sanderson |
| 7,549,511 | B2 | 6/2009 | Marocco |
| 7,549,512 | B2 | 6/2009 | Newberry |
| 7,585,293 | B2 | 9/2009 | Vermaak |
| 7,588,560 | B1 | 9/2009 | Dunlop |
| 7,637,905 | B2 | 12/2009 | Saadat et al. |
| 7,658,730 | B2 | 2/2010 | Conley |
| 7,665,359 | B2 | 2/2010 | Barber |
| 7,682,347 | B2 | 3/2010 | Parks et al. |
| 7,687,004 | B2 | 3/2010 | Allen |
| 7,695,459 | B2 | 4/2010 | Gilbert et al. |
| 7,695,460 | B2 | 4/2010 | Wada et al. |
| 7,699,818 | B2 | 4/2010 | Gilbert |
| 7,699,831 | B2 | 4/2010 | Bengtson et al. |
| 7,722,584 | B2 | 5/2010 | Tanaka et al. |
| 7,727,206 | B2 | 6/2010 | Gorres |
| 7,740,620 | B2 | 6/2010 | Gilbert et al. |
| 7,749,205 | B2 | 7/2010 | Tazoe et al. |
| 7,755,497 | B2 | 7/2010 | Wada et al. |
| 7,766,887 | B2 | 8/2010 | Burns et al. |
| 7,803,144 | B1 | 9/2010 | Vollrath |
| D625,407 | S | 10/2010 | Koizumi et al. |
| 7,806,879 | B2 | 10/2010 | Brooks et al. |
| 7,811,272 | B2 | 10/2010 | Lindsay et al. |
| 7,815,067 | B2 | 10/2010 | Matsumoto et al. |
| 7,833,169 | B2 | 11/2010 | Hannon |
| 7,857,806 | B2 | 12/2010 | Karpowicz et al. |
| 7,866,942 | B2 | 1/2011 | Harvie |
| 7,871,385 | B2 | 1/2011 | Levinson et al. |
| 7,875,010 | B2 | 1/2011 | Frazier et al. |
| 7,901,389 | B2 * | 3/2011 | Mombrinie ............. A61M 1/84 |
| | | | 604/317 |
| 7,927,320 | B2 | 4/2011 | Goldwasser et al. |
| 7,927,321 | B2 | 4/2011 | Marland |
| 7,931,634 | B2 | 4/2011 | Swiecicki et al. |
| 7,939,706 | B2 | 5/2011 | Okabe et al. |
| 7,946,443 | B2 | 5/2011 | Stull et al. |
| 7,947,025 | B2 | 5/2011 | Buglino et al. |
| 7,963,419 | B2 | 6/2011 | Burney et al. |
| 7,976,519 | B2 | 7/2011 | Bubb et al. |
| 7,993,318 | B2 | 8/2011 | Olsson et al. |
| 8,015,627 | B2 | 9/2011 | Baker et al. |
| 8,016,071 | B1 | 9/2011 | Martinus et al. |
| 8,028,460 | B2 | 10/2011 | Williams |
| 8,047,398 | B2 | 11/2011 | Dimartino et al. |
| 8,083,094 | B2 | 12/2011 | Caulfield et al. |

(56) References Cited

U.S. PATENT DOCUMENTS

| | | | |
|---|---|---|---|
| 8,128,608 B2 | 3/2012 | Thevenin | |
| 8,167,860 B1 | 5/2012 | Siegel | |
| 8,181,651 B2 | 5/2012 | Pinel | |
| 8,181,819 B2 | 5/2012 | Burney et al. | |
| 8,211,063 B2 | 7/2012 | Bierman et al. | |
| 8,221,369 B2 | 7/2012 | Parks et al. | |
| 8,241,262 B2 | 8/2012 | Mahnensmith | |
| 8,277,426 B2 | 10/2012 | Wilcox et al. | |
| 8,287,508 B1 * | 10/2012 | Sanchez | A61F 5/4404 |
| | | | 604/326 |
| 8,303,554 B2 * | 11/2012 | Tsai | A61B 5/445 |
| | | | 604/347 |
| 8,322,565 B2 | 12/2012 | Caulfield et al. | |
| 8,337,477 B2 | 12/2012 | Parks et al. | |
| D674,241 S | 1/2013 | Bickert et al. | |
| 8,343,122 B2 | 1/2013 | Gorres | |
| 8,343,125 B2 | 1/2013 | Kawazoe et al. | |
| 8,353,074 B2 | 1/2013 | Krebs | |
| 8,353,886 B2 | 1/2013 | Bester et al. | |
| D676,241 S | 2/2013 | Merrill | |
| 8,388,587 B1 | 3/2013 | Gmuer et al. | |
| 8,388,588 B2 | 3/2013 | Wada et al. | |
| D679,807 S | 4/2013 | Burgess et al. | |
| 8,425,482 B2 | 4/2013 | Khoubnazar | |
| 8,434,586 B2 | 5/2013 | Pawelski et al. | |
| 8,449,510 B2 | 5/2013 | Martini et al. | |
| D684,260 S | 6/2013 | Lund et al. | |
| 8,470,230 B2 | 6/2013 | Caulfield et al. | |
| 8,479,941 B2 | 7/2013 | Matsumoto et al. | |
| 8,479,949 B2 | 7/2013 | Henkel | |
| 8,500,719 B1 | 8/2013 | Simpson et al. | |
| 8,512,301 B2 | 8/2013 | Ma | |
| 8,529,530 B2 | 9/2013 | Koch et al. | |
| 8,535,284 B2 | 9/2013 | Joder et al. | |
| 8,546,639 B2 | 10/2013 | Wada et al. | |
| 8,551,062 B2 | 10/2013 | Kay | |
| 8,551,075 B2 | 10/2013 | Bengtson | |
| 8,568,376 B2 | 10/2013 | Delattre et al. | |
| D694,404 S | 11/2013 | Burgess et al. | |
| 8,585,683 B2 | 11/2013 | Bengtson et al. | |
| 8,652,112 B2 | 2/2014 | Johannison et al. | |
| 8,669,412 B2 | 3/2014 | Fernkvist et al. | |
| D702,973 S | 4/2014 | Norland et al. | |
| 8,703,032 B2 | 4/2014 | Menon et al. | |
| D704,330 S | 5/2014 | Cicatelli | |
| D704,510 S | 5/2014 | Mason et al. | |
| D705,423 S | 5/2014 | Walsh Cutler | |
| D705,926 S | 5/2014 | Burgess et al. | |
| 8,714,394 B2 | 5/2014 | Wulf | |
| 8,715,267 B2 | 5/2014 | Bengtson et al. | |
| 8,757,425 B2 | 6/2014 | Copeland | |
| 8,777,032 B2 | 7/2014 | Biesecker et al. | |
| 8,808,260 B2 | 8/2014 | Koch et al. | |
| 8,864,730 B2 | 10/2014 | Conway et al. | |
| 8,881,923 B2 | 11/2014 | Higginson | |
| 8,882,731 B2 | 11/2014 | Suzuki et al. | |
| 8,936,585 B2 | 1/2015 | Carson et al. | |
| D729,581 S | 5/2015 | Boroski | |
| 9,028,460 B2 | 5/2015 | Medeiros | |
| 9,056,698 B2 | 6/2015 | Noer | |
| 9,078,792 B2 | 7/2015 | Ruiz | |
| 9,145,879 B2 | 9/2015 | Pirovano et al. | |
| 9,173,602 B2 | 11/2015 | Gilbert | |
| 9,173,799 B2 | 11/2015 | Tanimoto et al. | |
| 9,187,220 B2 | 11/2015 | Biesecker et al. | |
| 9,199,772 B2 | 12/2015 | Krippendorf | |
| 9,233,020 B2 | 1/2016 | Matsumiya | |
| 9,248,058 B2 | 2/2016 | Conway et al. | |
| 9,308,118 B1 | 4/2016 | Dupree et al. | |
| 9,309,029 B2 | 4/2016 | Incorvia et al. | |
| 9,333,281 B2 | 5/2016 | Giezendanner et al. | |
| 9,381,108 B2 | 7/2016 | Longoni et al. | |
| 9,382,047 B2 | 7/2016 | Schmidtner et al. | |
| 9,402,424 B2 | 8/2016 | Roy | |
| 9,456,937 B2 | 10/2016 | Ellis | |
| 9,480,595 B2 | 11/2016 | Baham et al. | |
| 9,517,865 B2 | 12/2016 | Albers et al. | |
| D777,941 S | 1/2017 | Piramoon | |
| 9,533,806 B2 | 1/2017 | Ding et al. | |
| 9,550,611 B2 | 1/2017 | Hodge | |
| 9,555,930 B2 | 1/2017 | Campbell et al. | |
| 9,623,159 B2 | 4/2017 | Locke | |
| D789,522 S | 6/2017 | Burgess et al. | |
| 9,687,849 B2 | 6/2017 | Bruno et al. | |
| 9,694,949 B2 | 7/2017 | Hendricks et al. | |
| 9,709,048 B2 | 7/2017 | Kinjo | |
| 9,713,547 B2 | 7/2017 | Lee et al. | |
| 9,732,754 B2 | 8/2017 | Huang et al. | |
| 9,737,433 B2 | 8/2017 | Joh | |
| 9,752,564 B2 | 9/2017 | Arceno et al. | |
| 9,788,992 B2 | 10/2017 | Harvie | |
| D804,907 S | 12/2017 | Sandoval | |
| 9,868,564 B2 | 1/2018 | Mcgirr et al. | |
| D814,239 S | 4/2018 | Arora | |
| D817,484 S | 5/2018 | Lafond | |
| 9,968,908 B2 | 5/2018 | Ladrech et al. | |
| 10,010,393 B1 | 7/2018 | Nguyen et al. | |
| 10,037,640 B2 | 7/2018 | Gordon | |
| 10,058,470 B2 | 8/2018 | Phillips | |
| 10,098,990 B2 | 10/2018 | Koch et al. | |
| D835,264 S | 12/2018 | Mozzicato et al. | |
| D835,779 S | 12/2018 | Mozzicato et al. | |
| D840,533 S | 2/2019 | Mozzicato et al. | |
| D840,534 S | 2/2019 | Mozzicato et al. | |
| 10,225,376 B2 | 3/2019 | Perez Martinez | |
| 10,226,376 B2 * | 3/2019 | Sanchez | A61F 5/455 |
| 10,258,517 B1 | 4/2019 | Maschino et al. | |
| D848,612 S | 5/2019 | Mozzicato et al. | |
| 10,307,305 B1 | 6/2019 | Hodges | |
| 10,335,121 B2 | 7/2019 | Desai | |
| D856,512 S | 8/2019 | Cowart et al. | |
| 10,376,406 B2 * | 8/2019 | Newton | A61F 5/4404 |
| 10,376,407 B2 * | 8/2019 | Newton | A01K 23/005 |
| 10,390,989 B2 * | 8/2019 | Sanchez | A61F 5/453 |
| D858,144 S | 9/2019 | Fu | |
| 10,406,039 B2 | 9/2019 | Villarreal | |
| 10,407,222 B2 | 9/2019 | Allen | |
| 10,478,356 B2 | 11/2019 | Griffin | |
| 10,500,108 B1 | 12/2019 | Maschino et al. | |
| 10,502,198 B2 | 12/2019 | Stumpf et al. | |
| 10,538,366 B2 | 1/2020 | Pentelovitch et al. | |
| 10,569,938 B2 | 2/2020 | Zhao et al. | |
| 10,577,156 B2 | 3/2020 | Dagnelie et al. | |
| RE47,930 E | 4/2020 | Cho | |
| 10,618,721 B2 | 4/2020 | Vazin | |
| D884,390 S | 5/2020 | Wang | |
| 10,669,079 B2 | 6/2020 | Freedman et al. | |
| D892,315 S | 8/2020 | Airy | |
| 10,730,672 B2 | 8/2020 | Bertram et al. | |
| 10,737,848 B2 | 8/2020 | Philip et al. | |
| 10,765,854 B2 | 9/2020 | Law et al. | |
| 10,766,670 B2 | 9/2020 | Kittmann | |
| 10,799,386 B1 | 10/2020 | Harrison | |
| 10,806,642 B2 | 10/2020 | Tagomori et al. | |
| D901,214 S | 11/2020 | Hu | |
| 10,849,799 B2 | 12/2020 | Nishikawa et al. | |
| 10,857,025 B2 | 12/2020 | Davis et al. | |
| 10,865,017 B1 | 12/2020 | Cowart et al. | |
| 10,889,412 B2 | 1/2021 | West et al. | |
| 10,913,581 B2 | 2/2021 | Stahlecker | |
| D912,244 S | 3/2021 | Rehm et al. | |
| 10,952,889 B2 | 3/2021 | Newton et al. | |
| 10,973,378 B2 | 4/2021 | Ryu et al. | |
| 10,973,678 B2 | 4/2021 | Newton et al. | |
| 10,974,874 B2 | 4/2021 | Ragias et al. | |
| 11,000,401 B2 | 5/2021 | Ecklund et al. | |
| 11,002,165 B2 | 5/2021 | Poulin | |
| D923,365 S | 6/2021 | Wang | |
| 11,026,829 B2 | 6/2021 | Harvie | |
| 11,027,900 B2 | 6/2021 | Liu | |
| 11,045,346 B2 | 6/2021 | Argent et al. | |
| D928,946 S | 8/2021 | Sanchez et al. | |
| 11,090,183 B2 | 8/2021 | Sanchez et al. | |
| 11,160,695 B2 | 11/2021 | Febo et al. | |

(56)                    References Cited

U.S. PATENT DOCUMENTS

| | | | |
|---|---|---|---|
| 11,160,697 B2 | 11/2021 | Maschino et al. | |
| 11,168,420 B2 | 11/2021 | Kinugasa et al. | |
| 11,179,506 B2 | 11/2021 | Barr et al. | |
| 11,199,116 B2 | 12/2021 | Ostromecki et al. | |
| 11,207,206 B2 | 12/2021 | Sharma et al. | |
| 11,226,376 B2 | 1/2022 | Yamauchi et al. | |
| 11,253,389 B2 | 2/2022 | Sharma et al. | |
| 11,253,407 B2 | 2/2022 | Miao et al. | |
| 11,326,586 B2 | 5/2022 | Milner et al. | |
| 11,369,508 B2 | 6/2022 | Ecklund et al. | |
| 11,369,524 B2 | 6/2022 | Hubbard et al. | |
| 11,376,152 B2 | 7/2022 | Sanchez et al. | |
| 11,382,786 B2 | 7/2022 | Sanchez et al. | |
| 11,382,788 B2 | 7/2022 | Hjorth et al. | |
| 11,389,318 B2 | 7/2022 | Radl et al. | |
| 11,395,871 B2 | 7/2022 | Radl et al. | |
| 11,399,990 B2 | 8/2022 | Suyama | |
| 11,426,303 B2 | 8/2022 | Davis et al. | |
| 11,504,265 B2 | 11/2022 | Godinez et al. | |
| 11,529,252 B2 | 12/2022 | Glithero et al. | |
| 11,547,788 B2 | 1/2023 | Radl et al. | |
| 11,806,266 B2 | 11/2023 | Sanchez et al. | |
| 11,839,567 B2 | 12/2023 | Davis et al. | |
| D1,010,109 S | 1/2024 | Ecklund et al. | |
| 11,857,716 B2 | 1/2024 | Lee et al. | |
| 11,865,030 B2 | 1/2024 | Davis et al. | |
| 11,890,221 B2 | 2/2024 | Ulreich et al. | |
| 11,911,160 B2 | 2/2024 | Woodard et al. | |
| 11,925,575 B2 | 3/2024 | Newton | |
| 11,938,053 B2 | 3/2024 | Austermann et al. | |
| 11,944,740 B2 | 4/2024 | Hughett et al. | |
| 11,994,122 B2 | 5/2024 | Bodain | |
| 11,998,475 B2 | 6/2024 | Becker et al. | |
| 12,023,457 B2 | 7/2024 | Mann et al. | |
| 12,042,422 B2 | 7/2024 | Davis et al. | |
| D1,038,385 S | 8/2024 | Ecklund et al. | |
| 12,064,372 B2 | 8/2024 | Godinez et al. | |
| 12,070,432 B2 | 8/2024 | Tourchak et al. | |
| 12,090,083 B2 | 9/2024 | Ecklund et al. | |
| 12,133,813 B2 | 11/2024 | Ulreich et al. | |
| 12,138,195 B2 | 11/2024 | Alder et al. | |
| 12,186,229 B2 | 1/2025 | Davis et al. | |
| 12,245,966 B2 | 3/2025 | Newton | |
| 2001/0037097 A1* | 11/2001 | Cheng | A61F 5/455 |
| | | | 4/144.1 |
| 2001/0037098 A1 | 11/2001 | Snyder | |
| 2001/0054426 A1 | 12/2001 | Knudson et al. | |
| 2002/0019614 A1 | 2/2002 | Woon | |
| 2002/0026161 A1 | 2/2002 | Grundke | |
| 2002/0026163 A1 | 2/2002 | Grundke | |
| 2002/0042945 A1 | 4/2002 | Sands | |
| 2002/0087131 A1* | 7/2002 | Wolff | A61B 5/20 |
| | | | 604/327 |
| 2002/0091364 A1 | 7/2002 | Prabhakar | |
| 2002/0189992 A1 | 12/2002 | Schmidt et al. | |
| 2002/0193760 A1 | 12/2002 | Thompson | |
| 2002/0193762 A1 | 12/2002 | Suydam | |
| 2003/0004436 A1 | 1/2003 | Schmidt et al. | |
| 2003/0032931 A1 | 2/2003 | Grundke et al. | |
| 2003/0032944 A1 | 2/2003 | Cawood | |
| 2003/0073964 A1 | 4/2003 | Palumbo et al. | |
| 2003/0074724 A1 | 4/2003 | Sands | |
| 2003/0120178 A1* | 6/2003 | Heki | A61F 5/455 |
| | | | 600/574 |
| 2003/0129178 A1 | 7/2003 | Wegman et al. | |
| 2003/0157859 A1 | 8/2003 | Ishikawa | |
| 2003/0181880 A1 | 9/2003 | Schwartz | |
| 2003/0195484 A1 | 10/2003 | Harvie | |
| 2003/0204173 A1 | 10/2003 | Burns et al. | |
| 2003/0233079 A1 | 12/2003 | Parks et al. | |
| 2004/0006321 A1 | 1/2004 | Cheng et al. | |
| 2004/0015141 A1* | 1/2004 | Cheng | A61F 5/455 |
| | | | 604/329 |
| 2004/0056122 A1 | 3/2004 | Male et al. | |
| 2004/0084465 A1 | 5/2004 | Luburic | |
| 2004/0127872 A1 | 7/2004 | Petryk et al. | |
| 2004/0128749 A1 | 7/2004 | Scott | |
| 2004/0143229 A1 | 7/2004 | Easter | |
| 2004/0147863 A1 | 7/2004 | Diaz et al. | |
| 2004/0147894 A1 | 7/2004 | Mizutani et al. | |
| 2004/0147895 A1 | 7/2004 | Mizutani et al. | |
| 2004/0158221 A1 | 8/2004 | Mizutani et al. | |
| 2004/0176731 A1* | 9/2004 | Cheng | A61F 5/455 |
| | | | 604/329 |
| 2004/0176746 A1 | 9/2004 | Forral | |
| 2004/0181201 A1 | 9/2004 | Mizutani et al. | |
| 2004/0191919 A1 | 9/2004 | Unger et al. | |
| 2004/0194792 A1 | 10/2004 | Zhuang et al. | |
| 2004/0200936 A1 | 10/2004 | Opperthauser | |
| 2004/0207530 A1 | 10/2004 | Nielsen | |
| 2004/0236292 A1 | 11/2004 | Tazoe et al. | |
| 2004/0243075 A1 | 12/2004 | Harvie | |
| 2004/0254547 A1* | 12/2004 | Okabe | A61F 5/455 |
| | | | 604/317 |
| 2005/0010182 A1 | 1/2005 | Parks et al. | |
| 2005/0010197 A1 | 1/2005 | Lau et al. | |
| 2005/0033248 A1* | 2/2005 | Machida | A61F 5/455 |
| | | | 604/327 |
| 2005/0065471 A1 | 3/2005 | Kuntz | |
| 2005/0070861 A1 | 3/2005 | Okabe et al. | |
| 2005/0070862 A1 | 3/2005 | Tazoe et al. | |
| 2005/0082300 A1 | 4/2005 | Modrell et al. | |
| 2005/0097662 A1 | 5/2005 | Leimkuhler et al. | |
| 2005/0101924 A1 | 5/2005 | Elson et al. | |
| 2005/0119630 A1 | 6/2005 | Harvie | |
| 2005/0131361 A1 | 6/2005 | Miskie | |
| 2005/0137557 A1* | 6/2005 | Swiecicki | A61F 5/455 |
| | | | 604/385.17 |
| 2005/0137560 A1 | 6/2005 | Mizutani et al. | |
| 2005/0137561 A1 | 6/2005 | Mizutani et al. | |
| 2005/0154360 A1 | 7/2005 | Harvie | |
| 2005/0177070 A1 | 8/2005 | Levinson et al. | |
| 2005/0197639 A1 | 9/2005 | Mombrinie | |
| 2005/0197645 A1 | 9/2005 | Karpowicz et al. | |
| 2005/0215969 A1 | 9/2005 | Mizutani et al. | |
| 2005/0273069 A1 | 12/2005 | Mizutani et al. | |
| 2005/0273920 A1 | 12/2005 | Marinas | |
| 2005/0277903 A1 | 12/2005 | Mizutani et al. | |
| 2005/0277904 A1 | 12/2005 | Chase et al. | |
| 2005/0279359 A1 | 12/2005 | LeBlanc et al. | |
| 2006/0004332 A1 | 1/2006 | Marx | |
| 2006/0015080 A1 | 1/2006 | Mahnensmith | |
| 2006/0015081 A1 | 1/2006 | Suzuki et al. | |
| 2006/0016778 A1 | 1/2006 | Park | |
| 2006/0069359 A1* | 3/2006 | DiPalma | A61F 5/455 |
| | | | 604/327 |
| 2006/0079854 A1 | 4/2006 | Kay et al. | |
| 2006/0111648 A1 | 5/2006 | Vermaak | |
| 2006/0113334 A1 | 6/2006 | Mikhail et al. | |
| 2006/0155214 A1 | 7/2006 | Wightman | |
| 2006/0171997 A1 | 8/2006 | Gruenbacher et al. | |
| 2006/0180566 A1 | 8/2006 | Mataya | |
| 2006/0200102 A1 | 9/2006 | Cooper | |
| 2006/0229575 A1 | 10/2006 | Boiarski | |
| 2006/0229576 A1 | 10/2006 | Conway et al. | |
| 2006/0231648 A1 | 10/2006 | Male et al. | |
| 2006/0235266 A1 | 10/2006 | Nan | |
| 2006/0235359 A1 | 10/2006 | Marland | |
| 2006/0241553 A1 | 10/2006 | Harvie | |
| 2006/0269439 A1 | 11/2006 | White | |
| 2006/0277670 A1 | 12/2006 | Baker et al. | |
| 2007/0006368 A1 | 1/2007 | Key et al. | |
| 2007/0010797 A1 | 1/2007 | Nishtala et al. | |
| 2007/0016152 A1 | 1/2007 | Karpowicz et al. | |
| 2007/0038194 A1 | 2/2007 | Wada et al. | |
| 2007/0055209 A1 | 3/2007 | Patel et al. | |
| 2007/0073252 A1 | 3/2007 | Forgrave | |
| 2007/0117880 A1 | 5/2007 | Elson et al. | |
| 2007/0118993 A1 | 5/2007 | Bates | |
| 2007/0135786 A1 | 6/2007 | Schmidt et al. | |
| 2007/0137718 A1 | 6/2007 | Rushlander et al. | |
| 2007/0149935 A1 | 6/2007 | Dirico | |
| 2007/0191804 A1 | 8/2007 | Coley | |
| 2007/0203464 A1 | 8/2007 | Green et al. | |

(56)             References Cited

U.S. PATENT DOCUMENTS

| | | |
|---|---|---|
| 2007/0214553 A1 | 9/2007 | Carromba et al. |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1* | 2/2008 | Okabe ................... A61F 5/4404 |
| | | 604/378 |
| 2008/0041869 A1 | 2/2008 | Backaert |
| 2008/0077099 A1 | 3/2008 | House |
| 2008/0091153 A1 | 4/2008 | Harvie |
| 2008/0091158 A1 | 4/2008 | Yang |
| 2008/0114327 A1 | 5/2008 | Barge |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1* | 11/2008 | Van Den Heuvel .... A61F 5/455 |
| | | 604/327 |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0120179 A1 | 5/2009 | Nylander et al. |
| 2009/0192482 A1 | 7/2009 | Dodge et al. |
| 2009/0226541 A1 | 9/2009 | Scholz et al. |
| 2009/0234312 A1 | 9/2009 | Otoole et al. |
| 2009/0251510 A1 | 10/2009 | Noro et al. |
| 2009/0259206 A1 | 10/2009 | Kai et al. |
| 2009/0264840 A1 | 10/2009 | Virginio |
| 2009/0270822 A1 | 10/2009 | Medeiros |
| 2009/0281510 A1 | 11/2009 | Fisher |
| 2009/0283982 A1 | 11/2009 | Thomas |
| 2009/0306610 A1 | 12/2009 | Van Den Heuvel et al. |
| 2010/0004612 A1 | 1/2010 | Thevenin |
| 2010/0031429 A1 | 2/2010 | Kim et al. |
| 2010/0032789 A1 | 2/2010 | Schoen et al. |
| 2010/0058660 A1 | 3/2010 | Williams |
| 2010/0121289 A1 | 5/2010 | Parks et al. |
| 2010/0160882 A1 | 6/2010 | Lowe |
| 2010/0174250 A1 | 7/2010 | Hu et al. |
| 2010/0179493 A1 | 7/2010 | Heagle et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1* | 2/2011 | Wada ................... A61F 5/4401 |
| | | 604/318 |
| 2011/0040271 A1 | 2/2011 | Rogers et al. |
| 2011/0054426 A1 | 3/2011 | Stewart et al. |
| 2011/0060299 A1* | 3/2011 | Wada ................... A61F 5/455 |
| | | 604/318 |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1* | 7/2011 | Wada ................... A61F 13/42 |
| | | 604/385.01 |
| 2011/0198904 A1 | 8/2011 | Thomas et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0029452 A1 | 2/2012 | Roedsten |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1* | 5/2012 | Wheaton ................ A61F 5/453 |
| | | 128/885 |
| 2012/0116336 A1 | 5/2012 | Sharma et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0209216 A1 | 8/2012 | Jensen et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1* | 10/2012 | Suzuki ................... A61F 13/42 |
| | | 374/45 |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0019374 A1 | 1/2013 | Schwartz |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0110059 A1 | 5/2013 | Kossow et al. |
| 2013/0138064 A1 | 5/2013 | Stroebech et al. |
| 2013/0150813 A1 | 6/2013 | Gordon et al. |
| 2013/0165880 A1 | 6/2013 | Amos et al. |
| 2013/0218112 A1 | 8/2013 | Thompson |
| 2013/0245496 A1 | 9/2013 | Wells et al. |
| 2013/0245586 A1 | 9/2013 | Jha |
| 2013/0274711 A1 | 10/2013 | O'Day |
| 2013/0292537 A1 | 11/2013 | Dirico |
| 2013/0330501 A1 | 12/2013 | Aizenberg et al. |
| 2014/0005647 A1 | 1/2014 | Shuffler et al. |
| 2014/0031774 A1 | 1/2014 | Bengtson |
| 2014/0039432 A1 | 2/2014 | Dunbar et al. |
| 2014/0039440 A1 | 2/2014 | Doescher |
| 2014/0058347 A1 | 2/2014 | Marquette |
| 2014/0107599 A1 | 4/2014 | Fink et al. |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209188 A1 | 7/2015 | Scheremet et al. |
| 2015/0209194 A1 | 7/2015 | Heyman |
| 2015/0267862 A1 | 9/2015 | Mishler |
| 2015/0290421 A1 | 10/2015 | Glickman et al. |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1 | 12/2015 | Harvie |
| 2015/0359996 A1 | 12/2015 | Arora et al. |
| 2015/0366699 A1 | 12/2015 | Nelson |

(56)     References Cited

U.S. PATENT DOCUMENTS

| | | |
|---|---|---|
| 2016/0029998 A1 | 2/2016 | Brister et al. |
| 2016/0030228 A1 | 2/2016 | Jones |
| 2016/0038356 A1 | 2/2016 | Yao et al. |
| 2016/0051395 A1 | 2/2016 | Ugarte |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0136338 A1 | 5/2016 | Lee et al. |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0374848 A1* | 12/2016 | Sanchez ................ A61F 5/453 |
| | | 604/319 |
| 2017/0007438 A1 | 1/2017 | Harvie |
| 2017/0014560 A1 | 1/2017 | Minskoff et al. |
| 2017/0042724 A1 | 2/2017 | Ugarte |
| 2017/0042748 A1 | 2/2017 | Griffin |
| 2017/0100276 A1 | 4/2017 | Joh |
| 2017/0107312 A1* | 4/2017 | Hinayama ............... A61F 13/53 |
| 2017/0128638 A1 | 5/2017 | Giezendanner et al. |
| 2017/0136209 A1 | 5/2017 | Burnett et al. |
| 2017/0143534 A1 | 5/2017 | Sanchez |
| 2017/0165100 A1 | 6/2017 | Jackson et al. |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0238911 A1 | 8/2017 | Duval |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1* | 9/2017 | Sanchez ............... A61F 5/4404 |
| 2017/0266658 A1 | 9/2017 | Bruno et al. |
| 2017/0281399 A1* | 10/2017 | VanMiddendorp ..... A61F 5/455 |
| 2017/0281419 A1 | 10/2017 | Pintado |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0348139 A1* | 12/2017 | Newton ............... A61F 5/4404 |
| 2017/0354532 A1 | 12/2017 | Holt |
| 2017/0354551 A1 | 12/2017 | Gawley et al. |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1* | 2/2018 | Newton .................. A61M 1/71 |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1* | 8/2018 | Davis ..................... A61F 5/451 |
| 2018/0256384 A1 | 9/2018 | Kasirye |
| 2018/0271694 A1 | 9/2018 | Fernandez et al. |
| 2018/0317892 A1 | 11/2018 | Catlin |
| 2018/0325748 A1 | 11/2018 | Sharma et al. |
| 2019/0001030 A1 | 1/2019 | Braga et al. |
| 2019/0021899 A1 | 1/2019 | Met |
| 2019/0038451 A1 | 2/2019 | Harvie |
| 2019/0046102 A1 | 2/2019 | Kushnir et al. |
| 2019/0059938 A1 | 2/2019 | Holsten |
| 2019/0091059 A1 | 3/2019 | Gabriel |
| 2019/0100362 A1 | 4/2019 | Meyers et al. |
| 2019/0133126 A1 | 5/2019 | Modak et al. |
| 2019/0133814 A1 | 5/2019 | Tammen et al. |
| 2019/0142624 A1* | 5/2019 | Sanchez ................ A61F 5/453 |
| | | 604/319 |
| 2019/0224036 A1 | 7/2019 | Sanchez et al. |
| 2019/0226189 A1 | 7/2019 | Braxton |
| 2019/0240079 A1 | 8/2019 | Tuli |
| 2019/0247222 A1 | 8/2019 | Ecklund et al. |
| 2019/0247223 A1 | 8/2019 | Brun et al. |
| 2019/0247623 A1 | 8/2019 | Helm et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365303 A1 | 12/2019 | Bullington et al. |
| 2019/0365307 A1 | 12/2019 | Laing et al. |
| 2019/0365561 A1 | 12/2019 | Newton et al. |
| 2019/0374373 A1 | 12/2019 | Joh |
| 2020/0008985 A1 | 1/2020 | Nguyen et al. |
| 2020/0016012 A1 | 1/2020 | Dutkiewicz |
| 2020/0030595 A1 | 1/2020 | Boukidjian et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-schärli et al. |
| 2020/0107518 A1 | 4/2020 | Hiroshima et al. |
| 2020/0129322 A1 | 4/2020 | Leuckel |
| 2020/0171217 A9 | 6/2020 | Braga et al. |
| 2020/0179177 A1 | 6/2020 | Erdem et al. |
| 2020/0187918 A1 | 6/2020 | Wiygul |
| 2020/0206015 A1 | 7/2020 | Langer |
| 2020/0206039 A1 | 7/2020 | Mclain |
| 2020/0214910 A1 | 7/2020 | Varona et al. |
| 2020/0216898 A1 | 7/2020 | Hubbell |
| 2020/0216989 A1 | 7/2020 | Kinugasa et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0246203 A1 | 8/2020 | Tulk et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1 | 10/2020 | Eckert |
| 2020/0315872 A1 | 10/2020 | Viens et al. |
| 2020/0315874 A1 | 10/2020 | Viens et al. |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0375810 A1 | 12/2020 | Carlin et al. |
| 2020/0384242 A1 | 12/2020 | Havard et al. |
| 2020/0385179 A1 | 12/2020 | Mccourt |
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0023279 A1 | 1/2021 | Radl et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0069009 A1 | 3/2021 | Im |
| 2021/0069030 A1 | 3/2021 | Nishikawa et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0178390 A1 | 6/2021 | Oueslati et al. |

(56) References Cited

U.S. PATENT DOCUMENTS

| 2021/0186742 A1 | 6/2021 | Newton et al. |
| 2021/0211568 A1 | 7/2021 | Zhou et al. |
| 2021/0212865 A1 | 7/2021 | Wallajapet et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0236324 A1 | 8/2021 | Sweeney |
| 2021/0251814 A1 | 8/2021 | Jönegren et al. |
| 2021/0267787 A1 | 9/2021 | Nazemi |
| 2021/0275343 A1 | 9/2021 | Sanchez et al. |
| 2021/0275344 A1 | 9/2021 | Wing |
| 2021/0290454 A1 | 9/2021 | Yamada |
| 2021/0315726 A1 | 10/2021 | Lin |
| 2021/0315727 A1 | 10/2021 | Jiang |
| 2021/0353449 A1 | 11/2021 | Sharma et al. |
| 2021/0353450 A1 | 11/2021 | Sharma et al. |
| 2021/0361469 A1 | 11/2021 | Liu et al. |
| 2021/0369495 A1 | 12/2021 | Cheng et al. |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0031290 A1 | 2/2022 | Weed |
| 2022/0031523 A1 | 2/2022 | Pierpoint |
| 2022/0039995 A1 | 2/2022 | Johannes et al. |
| 2022/0047410 A1 | 2/2022 | Walthall |
| 2022/0062027 A1 | 3/2022 | Mitchell et al. |
| 2022/0062028 A1 | 3/2022 | Mitchell et al. |
| 2022/0062029 A1 | 3/2022 | Johannes et al. |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104976 A1 | 4/2022 | Hoeger et al. |
| 2022/0104981 A1 | 4/2022 | Jones |
| 2022/0117773 A1 | 4/2022 | Davis et al. |
| 2022/0117774 A1 | 4/2022 | Meyer et al. |
| 2022/0117775 A1 | 4/2022 | Jones et al. |
| 2022/0118165 A1 | 4/2022 | Knapp et al. |
| 2022/0133524 A1 | 5/2022 | Davis |
| 2022/0151817 A1 | 5/2022 | Mann |
| 2022/0160949 A1 | 5/2022 | Simiele et al. |
| 2022/0168159 A1 | 6/2022 | Triado et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0247407 A1 | 8/2022 | Yamamoto et al. |
| 2022/0248836 A1 | 8/2022 | Cagle et al. |
| 2022/0257407 A1 | 8/2022 | Johannes et al. |
| 2022/0265460 A1 | 8/2022 | Coker |
| 2022/0265462 A1 | 8/2022 | Alder et al. |
| 2022/0270711 A1 | 8/2022 | Feala et al. |
| 2022/0273482 A1 | 9/2022 | Johannes et al. |
| 2022/0280357 A1 | 9/2022 | Jagannathan et al. |
| 2022/0280710 A1 | 9/2022 | Agrawal et al. |
| 2022/0287689 A1 | 9/2022 | Johannes |
| 2022/0287867 A1 | 9/2022 | Jones et al. |
| 2022/0287868 A1 | 9/2022 | Garvey et al. |
| 2022/0296408 A1 | 9/2022 | Evans et al. |
| 2022/0305191 A1 | 9/2022 | Joseph et al. |
| 2022/0313222 A1 | 10/2022 | Austermann et al. |
| 2022/0313474 A1 | 10/2022 | Kriscovich et al. |
| 2022/0331170 A1 | 10/2022 | Erdem et al. |
| 2022/0339023 A1 | 10/2022 | Davis et al. |
| 2022/0339024 A1 | 10/2022 | Johannes et al. |
| 2022/0354685 A1 | 11/2022 | Davis et al. |
| 2022/0362049 A1 | 11/2022 | Austermann et al. |
| 2022/0370231 A1 | 11/2022 | Wang et al. |
| 2022/0370234 A1 | 11/2022 | Hughett et al. |
| 2022/0370235 A1 | 11/2022 | Johannes et al. |
| 2022/0370237 A1 | 11/2022 | Parmar et al. |
| 2022/0387001 A1 | 12/2022 | Askenazi et al. |
| 2022/0387693 A1 | 12/2022 | Bannwart et al. |
| 2022/0395390 A1 | 12/2022 | Brooks |
| 2022/0395391 A1 | 12/2022 | Saunders et al. |
| 2022/0401252 A1 | 12/2022 | Warren |
| 2022/0409419 A1 | 12/2022 | Garvey et al. |
| 2022/0409422 A1 | 12/2022 | Schneider et al. |
| 2023/0018845 A1 | 1/2023 | Lee |
| 2023/0020563 A1 | 1/2023 | Sharma et al. |
| 2023/0031640 A1 | 2/2023 | Hughett et al. |
| 2023/0037159 A1 | 2/2023 | Brennan et al. |
| 2023/0049924 A1 | 2/2023 | Johannes et al. |
| 2023/0052238 A1 | 2/2023 | Oluwasogo |
| 2023/0062994 A1 | 3/2023 | Ecklund et al. |
| 2023/0070347 A1 | 3/2023 | Watson et al. |
| 2023/0073708 A1 | 3/2023 | Xu et al. |
| 2023/0089032 A1 | 3/2023 | Hughett et al. |
| 2023/0091118 A1 | 3/2023 | Watson |
| 2023/0099821 A1 | 3/2023 | Radl et al. |
| 2023/0099991 A1 | 3/2023 | Bianchi et al. |
| 2023/0105001 A1 | 4/2023 | Whittome et al. |
| 2023/0110577 A1 | 4/2023 | Choi |
| 2023/0138269 A1 | 5/2023 | Abdelal et al. |
| 2023/0145365 A1 | 5/2023 | Martin et al. |
| 2023/0155253 A1 | 5/2023 | Mn et al. |
| 2023/0210504 A1 | 7/2023 | Kuroda et al. |
| 2023/0210685 A1 | 7/2023 | Fallows et al. |
| 2023/0218426 A1 | 7/2023 | Hughett |
| 2023/0240884 A1 | 8/2023 | Davis et al. |
| 2023/0248562 A1 | 8/2023 | Sanchez et al. |
| 2023/0248564 A1 | 8/2023 | Mann et al. |
| 2023/0255812 A1 | 8/2023 | Sanchez et al. |
| 2023/0255813 A1 | 8/2023 | Sanchez et al. |
| 2023/0255815 A1 | 8/2023 | Newton |
| 2023/0263650 A1 | 8/2023 | Sanchez et al. |
| 2023/0263655 A1 | 8/2023 | Johannes et al. |
| 2023/0277360 A1 | 9/2023 | Lambert et al. |
| 2023/0277362 A1 | 9/2023 | Davis et al. |
| 2023/0285178 A1 | 9/2023 | Sanchez et al. |
| 2023/0293339 A1 | 9/2023 | James |
| 2023/0301846 A1 | 9/2023 | Greenwood |
| 2023/0355423 A1 | 11/2023 | Stevenson et al. |
| 2023/0404791 A1 | 12/2023 | Ecklund et al. |
| 2024/0008444 A1 | 1/2024 | Su et al. |
| 2024/0009023 A1 | 1/2024 | Johannes et al. |
| 2024/0024170 A1 | 1/2024 | Scott |
| 2024/0033148 A1 | 2/2024 | Gordon et al. |
| 2024/0041638 A1 | 2/2024 | Johannes et al. |
| 2024/0058160 A1 | 2/2024 | Young Joyner et al. |
| 2024/0058161 A1 | 2/2024 | Ulreich et al. |
| 2024/0058520 A1 | 2/2024 | Mn et al. |
| 2024/0065881 A1 | 2/2024 | Kuroda et al. |
| 2024/0082044 A1 | 3/2024 | Nguyen et al. |
| 2024/0099874 A1 | 3/2024 | Sanchez et al. |
| 2024/0108268 A1 | 4/2024 | Woodard et al. |
| 2024/0110318 A1 | 4/2024 | Bendt et al. |
| 2024/0122773 A1 | 4/2024 | Nguyen et al. |
| 2024/0123134 A1 | 4/2024 | Kharkar et al. |
| 2024/0148539 A1 | 5/2024 | Austermann et al. |
| 2024/0156633 A1 | 5/2024 | Fallows et al. |
| 2024/0252343 A1 | 8/2024 | Voda |
| 2024/0261131 A1 | 8/2024 | Garvey et al. |
| 2024/0268986 A1 | 8/2024 | Barnes et al. |
| 2024/0268989 A1 | 8/2024 | Martin et al. |
| 2024/0269027 A1 | 8/2024 | Tourchak et al. |
| 2024/0285425 A1 | 8/2024 | Donohoe et al. |
| 2024/0325190 A1 | 10/2024 | Minchew et al. |
| 2024/0358539 A1 | 10/2024 | Gallup |
| 2024/0358542 A1 | 10/2024 | Richardson et al. |
| 2024/0374414 A1 | 11/2024 | Richardson et al. |
| 2025/0009552 A1 | 1/2025 | Blabas et al. |
| 2025/0073055 A1 | 3/2025 | Ecklund et al. |

(56) References Cited

U.S. PATENT DOCUMENTS

2025/0107920 A1    4/2025   Fallows et al.
2025/0107921 A1    4/2025   Sanchez et al.

FOREIGN PATENT DOCUMENTS

| | | | |
|---|---|---|---|
| AU | 2022349367 A1 | 4/2024 | |
| CA | 2165286 C | 9/1999 | |
| CA | 2354132 A1 * | 6/2000 | |
| CA | 2359091 C | 9/2003 | |
| CA | 1602825 A | 4/2005 | |
| CA | 1720888 A | 1/2006 | |
| CA | 2488867 C | 8/2007 | |
| CA | 103717180 A | 4/2014 | |
| CA | 3050918 A1 | 8/2018 | |
| CA | 3098571 A1 | 11/2019 | |
| CA | 3188651 A1 | 7/2023 | |
| CN | 2269203 Y | 12/1997 | |
| CN | 1332620 A | 1/2002 | |
| CN | 1434693 A | 8/2003 | |
| CN | 1533755 A | 10/2004 | |
| CN | 2936204 Y | 8/2007 | |
| CN | 101262836 A | 9/2008 | |
| CN | 101522148 A | 9/2009 | |
| CN | 102159159 A | 8/2011 | |
| CN | 202184840 U | 4/2012 | |
| CN | 102481441 A | 5/2012 | |
| CN | 202463712 U | 10/2012 | |
| CN | 202950810 U | 5/2013 | |
| CN | 103533968 A | 1/2014 | |
| CN | 204562697 U | 8/2015 | |
| CN | 105411783 A * | 3/2016 | A61F 5/4404 |
| CN | 105451693 A | 3/2016 | |
| CN | 105534632 A | 5/2016 | |
| CN | 106132360 A | 11/2016 | |
| CN | 205849719 U | 1/2017 | |
| CN | 205924282 U | 2/2017 | |
| CN | 106726089 A | 5/2017 | |
| CN | 107847384 A | 3/2018 | |
| CN | 107920912 A | 4/2018 | |
| CN | 108420590 A | 8/2018 | |
| CN | 209285902 U | 8/2019 | |
| CN | 110381883 A | 10/2019 | |
| CN | 211198839 U | 8/2020 | |
| CN | 111991136 A | 11/2020 | |
| CN | 112022488 A | 12/2020 | |
| CN | 212234893 U | 12/2020 | |
| CN | 212466312 U | 2/2021 | |
| CN | 112566550 A | 3/2021 | |
| CN | 112603184 A | 4/2021 | |
| CN | 213490035 U | 6/2021 | |
| CN | 114007493 A | 2/2022 | |
| CN | 114375187 A | 4/2022 | |
| CN | 116096332 A | 5/2023 | |
| DE | 1516466 A1 | 6/1969 | |
| DE | 2721330 A1 | 11/1977 | |
| DE | 2742298 A1 | 3/1978 | |
| DE | 9407554.9 U1 | 5/1995 | |
| DE | 4443710 A1 | 6/1995 | |
| DE | 4416094 A1 | 11/1995 | |
| DE | 4236097 C2 | 10/1996 | |
| DE | 19619597 A1 * | 11/1997 | A61F 5/451 |
| DE | 102005037762 B3 | 9/2006 | |
| DE | 102011103783 A1 | 12/2012 | |
| DE | 102012112818 A1 | 6/2014 | |
| DE | 202015104597 U1 | 7/2016 | |
| DE | 102020121462 B3 | 1/2022 | |
| DK | 9600118 | 11/1996 | |
| EP | 0032138 A2 | 7/1981 | |
| EP | 0066070 B1 | 12/1982 | |
| EP | 0068712 A1 | 1/1983 | |
| EP | 0140470 A1 | 5/1985 | |
| EP | 0220962 A1 | 5/1987 | |
| EP | 0140471 B1 | 5/1988 | |
| EP | 0274753 A2 | 7/1988 | |
| EP | 0119143 B1 | 11/1988 | |
| EP | 0483592 A1 * | 5/1992 | |
| EP | 0483730 A1 | 5/1992 | |
| EP | 0610638 A1 | 8/1994 | |
| EP | 0613355 A1 | 9/1994 | |
| EP | 0613355 B1 * | 1/1997 | |
| EP | 0787472 A1 | 8/1997 | |
| EP | 0966936 A1 | 12/1999 | |
| EP | 0987293 A1 | 3/2000 | |
| EP | 1063953 A1 | 1/2001 | |
| EP | 0653928 B1 | 10/2002 | |
| EP | 1332738 A1 | 8/2003 | |
| EP | 1382318 A1 | 1/2004 | |
| EP | 1089684 B1 | 10/2004 | |
| EP | 1616542 A1 | 1/2006 | |
| EP | 1382318 B1 | 5/2006 | |
| EP | 1063953 B1 * | 1/2007 | A61F 13/47209 |
| EP | 1658831 B1 | 1/2008 | |
| EP | 1872752 A1 | 1/2008 | |
| EP | 2180907 A1 | 5/2010 | |
| EP | 2380532 A1 | 10/2011 | |
| EP | 2389908 A1 | 11/2011 | |
| EP | 2601916 A1 | 6/2013 | |
| EP | 2676643 A1 | 12/2013 | |
| EP | 2997950 A2 | 3/2016 | |
| EP | 2879534 B1 | 3/2017 | |
| EP | 3424471 A1 | 1/2019 | |
| EP | 3169292 B1 | 11/2019 | |
| EP | 3753492 A1 | 12/2020 | |
| EP | 3788992 A1 | 3/2021 | |
| EP | 3576689 B1 | 3/2022 | |
| EP | 3752110 B1 | 3/2022 | |
| EP | 3787570 B1 | 3/2022 | |
| EP | 4025163 A1 | 7/2022 | |
| EP | 3463180 B1 | 3/2023 | |
| EP | 3569205 B1 | 6/2023 | |
| EP | 4382082 A2 | 6/2024 | |
| EP | 4445881 A2 | 10/2024 | |
| EP | 4464288 A2 | 11/2024 | |
| EP | 4527361 A2 | 3/2025 | |
| FR | 2826704 A1 | 1/2003 | |
| GB | 871820 A | 7/1961 | |
| GB | 873045 A | 7/1961 | |
| GB | 1011517 A | 12/1965 | |
| GB | 1467144 A | 3/1977 | |
| GB | 2106395 A | 4/1983 | |
| GB | 2106784 A | 4/1983 | |
| GB | 2148126 A * | 5/1985 | A61F 13/15268 |
| GB | 2171315 A | 8/1986 | |
| GB | 2181953 A | 5/1987 | |
| GB | 2148126 B | 7/1987 | |
| GB | 2191095 A | 12/1987 | |
| GB | 2199750 A | 7/1988 | |
| GB | 2260907 A | 5/1993 | |
| GB | 2462267 A | 2/2010 | |
| GB | 2469496 A | 10/2010 | |
| GB | 2490327 A | 10/2012 | |
| GB | 2507318 A | 4/2014 | |
| GB | 2612752 A * | 5/2023 | A61F 5/451 |
| IT | 201800009129 A1 | 4/2020 | |
| JP | S498638 U | 1/1974 | |
| JP | S5410596 A | 1/1979 | |
| JP | S5410596 Y2 | 5/1979 | |
| JP | S54155729 U | 10/1979 | |
| JP | S55155618 A | 12/1980 | |
| JP | S57142534 U | 9/1982 | |
| JP | S5888596 U | 6/1983 | |
| JP | S58188016 U | 12/1983 | |
| JP | S63107780 U | 7/1988 | |
| JP | H0267530 A | 3/1990 | |
| JP | H02103871 A | 4/1990 | |
| JP | H02131422 A | 5/1990 | |
| JP | H02131422 U | 11/1990 | |
| JP | H0460220 A | 2/1992 | |
| JP | H05123349 A | 5/1993 | |
| JP | H05123350 A | 5/1993 | |
| JP | H0626264 U | 4/1994 | |
| JP | H085630 A | 1/1996 | |
| JP | H1040141 A | 2/1998 | |
| JP | H10225430 A | 8/1998 | |

(56) References Cited

FOREIGN PATENT DOCUMENTS

| | | | |
|---|---|---|---|
| JP | H11113946 A | 4/1999 |
| JP | H11290365 A | 10/1999 |
| JP | 2000116690 A | 4/2000 |
| JP | 2000185068 A | 7/2000 |
| JP | 2000225139 A | 8/2000 |
| JP | 3087938 B2 | 9/2000 |
| JP | 2001054531 | 2/2001 |
| JP | 2001054531 A | 2/2001 |
| JP | 2001070331 A | 3/2001 |
| JP | 2001224616 A | 8/2001 |
| JP | 2001276107 A | 10/2001 |
| JP | 2001276108 A | 10/2001 |
| JP | 2002028173 A | 1/2002 |
| JP | 2003038563 A | 2/2003 |
| JP | 2003505152 A | 2/2003 |
| JP | 2003126242 A | 5/2003 |
| JP | 2003180722 A | 7/2003 |
| JP | 2003528691 A | 9/2003 |
| JP | 2004057578 A | 2/2004 |
| JP | 2004130056 A | 4/2004 |
| JP | 2004267530 A | 9/2004 |
| JP | 2005052219 A | 3/2005 |
| JP | 2005066011 A | 3/2005 |
| JP | 2005066325 A | 3/2005 |
| JP | 2005102978 A | 4/2005 |
| JP | 2005518237 A | 6/2005 |
| JP | 2005518901 A | 6/2005 |
| JP | 3749097 B2 | 12/2005 |
| JP | 2006026108 A | 2/2006 |
| JP | 3123547 B2 | 6/2006 |
| JP | 2006136492 A | 6/2006 |
| JP | 2006204868 A | 8/2006 |
| JP | 2007044494 A | 2/2007 |
| JP | 3132659 B2 | 5/2007 |
| JP | 2007209687 A | 8/2007 |
| JP | 2007259898 A | 10/2007 |
| JP | 4039641 B2 | 11/2007 |
| JP | 2008005975 A | 1/2008 |
| JP | 2009509570 A | 3/2009 |
| JP | 2009165887 A | 7/2009 |
| JP | 2009525776 A | 7/2009 |
| JP | 2010504150 A | 2/2010 |
| JP | 2010058795 A | 3/2010 |
| JP | 2010081981 A | 4/2010 |
| JP | 2010166954 A | 8/2010 |
| JP | 4640772 B2 | 12/2010 |
| JP | 2010536439 A | 12/2010 |
| JP | 2011500225 A | 1/2011 |
| JP | 2011030962 A | 2/2011 |
| JP | 4747166 B2 | 5/2011 |
| JP | 2011087823 A | 5/2011 |
| JP | 4801218 B1 | 8/2011 |
| JP | 2011218130 A | 11/2011 |
| JP | 2011224070 A | 11/2011 |
| JP | 3175719 U | 4/2012 |
| JP | 2012523869 A | 10/2012 |
| JP | 2013238608 A | 11/2013 |
| JP | 2014521960 A | 8/2014 |
| JP | 2015092945 A | 5/2015 |
| JP | 2015513678 A | 5/2015 |
| JP | 3198994 B2 | 7/2015 |
| JP | 2015221390 A | 12/2015 |
| JP | 2016521191 A | 7/2016 |
| JP | 2017014698 A | 1/2017 |
| JP | 2017070400 A | 4/2017 |
| JP | 2017512603 A | 5/2017 |
| JP | 2017201272 A | 11/2017 |
| JP | 2019010375 A | 1/2019 |
| JP | 2019076342 A | 5/2019 |
| JP | 2019525811 A | 9/2019 |
| JP | 2019170942 A | 10/2019 |
| JP | 2019533492 A | 11/2019 |
| JP | 2020520775 A | 7/2020 |
| JP | 2021007472 A | 1/2021 |
| JP | 2021120686 A | 8/2021 |
| JP | 2021522009 A | 8/2021 |
| JP | 2021522013 A | 8/2021 |
| JP | 7129493 B2 | 8/2022 |
| JP | 2023532132 A | 7/2023 |
| KR | 200290061 Y1 | 9/2002 |
| KR | 20030047451 A | 6/2003 |
| KR | 20080005516 A | 1/2008 |
| KR | 20090072069 A | 7/2009 |
| KR | 20090104426 A | 10/2009 |
| KR | 20090110359 A | 10/2009 |
| KR | 20120005922 A | 1/2012 |
| KR | 20140039485 A | 4/2014 |
| KR | 101432639 B1 | 8/2014 |
| KR | 20180106659 A | 10/2018 |
| KR | 20180108774 A | 10/2018 |
| KR | 20230034343 A | 3/2023 |
| PT | 2068717 E | 6/2013 |
| SE | 505542 C2 | 9/1997 |
| WO | 8101957 A1 | 7/1981 |
| WO | WO-8804558 A1 * | 12/1986 |
| WO | WO-9104714 A2 * | 8/1990 |
| WO | 9104714 A3 | 6/1991 |
| WO | 9220299 A3 | 2/1993 |
| WO | 9303690 A1 | 3/1993 |
| WO | 9307839 A1 | 4/1993 |
| WO | WO-9309736 A2 * | 5/1993 ........... A61F 5/4401 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |
| WO | 0069377 A1 | 11/2000 |
| WO | 0079497 A1 | 12/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | 03055423 A1 | 7/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2004026195 A1 | 4/2004 |
| WO | WO-2005051252 A1 * | 6/2005 ........... A61F 5/4408 |
| WO | 2005060558 A2 | 7/2005 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | 2006037140 A2 | 4/2006 |
| WO | 2007005851 A2 | 1/2007 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009052502 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |

(56)                    References Cited

FOREIGN PATENT DOCUMENTS

| | | | |
|---|---|---|---|
| WO | 2011024864 A1 | 3/2011 | |
| WO | 2011054118 A1 | 5/2011 | |
| WO | 2011079132 A1 | 6/2011 | |
| WO | 2011107972 A1 | 9/2011 | |
| WO | 2011108972 A1 | 9/2011 | |
| WO | 2011117292 A1 | 9/2011 | |
| WO | 2011123219 A1 | 10/2011 | |
| WO | 2011132043 A1 | 10/2011 | |
| WO | 2012012908 A1 | 2/2012 | |
| WO | 2012020506 A1 | 2/2012 | |
| WO | 2012065274 A1 | 5/2012 | |
| WO | 2012097462 A1 | 7/2012 | |
| WO | 2012098796 A1 | 7/2012 | |
| WO | 2012101288 A1 | 8/2012 | |
| WO | 2012175916 A1 | 12/2012 | |
| WO | 2013018435 A1 | 2/2013 | |
| WO | 2013033429 A1 | 3/2013 | |
| WO | 2013055434 A1 | 4/2013 | |
| WO | 2013082397 A1 | 6/2013 | |
| WO | 2013103291 A2 | 7/2013 | |
| WO | 2013131109 A1 | 9/2013 | |
| WO | 2013167478 A1 | 11/2013 | |
| WO | 2013177716 A1 | 12/2013 | |
| WO | 2014041534 A1 | 3/2014 | |
| WO | 2014046420 A1 | 3/2014 | |
| WO | 2014118518 A1 | 8/2014 | |
| WO | 2014160852 A1 | 10/2014 | |
| WO | 2015023599 A1 | 2/2015 | |
| WO | 2015052348 A1 | 4/2015 | |
| WO | 2015068384 A1 | 5/2015 | |
| WO | 2015169403 A1 | 11/2015 | |
| WO | 2015170307 A1 | 11/2015 | |
| WO | 2015197462 A1 | 12/2015 | |
| WO | 2016055989 A1 | 4/2016 | |
| WO | WO-2016051385 A1 * | 4/2016 | |
| WO | 2016071894 A1 | 5/2016 | |
| WO | 2016103242 A1 | 6/2016 | |
| WO | 2016116915 A1 | 7/2016 | |
| WO | 2016124203 A1 | 8/2016 | |
| WO | 2016139448 A1 | 9/2016 | |
| WO | 2016166562 A1 | 10/2016 | |
| WO | 2016167535 A1 | 10/2016 | |
| WO | 2016191574 A1 | 12/2016 | |
| WO | 2016200088 A1 | 12/2016 | |
| WO | 2016200361 A1 | 12/2016 | |
| WO | 2016204731 A1 | 12/2016 | |
| WO | 2017001532 A2 | 1/2017 | |
| WO | 2017075226 A1 | 5/2017 | |
| WO | 2017152198 A1 | 9/2017 | |
| WO | 2017153357 A1 | 9/2017 | |
| WO | 2017162559 A1 | 9/2017 | |
| WO | 2017205446 A1 | 11/2017 | |
| WO | WO-2017209779 A1 * | 12/2017 | A61F 5/4404 |
| WO | WO-2017210524 A1 * | 12/2017 | A61D 1/00 |
| WO | WO-2018022414 A1 * | 2/2018 | A61F 5/453 |
| WO | 2018044781 A1 | 3/2018 | |
| WO | 2018056953 A1 | 3/2018 | |
| WO | 2018090550 A1 | 5/2018 | |
| WO | 2018138513 A1 | 8/2018 | |
| WO | 2018144318 A1 | 8/2018 | |
| WO | 2018144463 A1 | 8/2018 | |
| WO | 2018150263 A1 | 8/2018 | |
| WO | 2018150268 A1 | 8/2018 | |
| WO | 2018152156 A1 | 8/2018 | |
| WO | 2018183791 A1 | 10/2018 | |
| WO | 2018150267 A3 | 11/2018 | |
| WO | 2018235026 A1 | 12/2018 | |
| WO | 2018235065 A1 | 12/2018 | |
| WO | 2019004404 A1 | 1/2019 | |
| WO | 2019041005 A1 | 3/2019 | |
| WO | 2019044217 A1 | 3/2019 | |
| WO | 2019044218 A1 | 3/2019 | |
| WO | 2019044219 A1 | 3/2019 | |
| WO | 2019050959 A1 | 3/2019 | |
| WO | 2019065541 A1 | 4/2019 | |
| WO | 2019096845 A1 | 5/2019 | |
| WO | 2019150385 A1 | 8/2019 | |
| WO | 2019161094 A1 | 8/2019 | |
| WO | 2019188566 A1 | 10/2019 | |
| WO | 2019190593 A1 | 10/2019 | |
| WO | 2019212949 A1 | 11/2019 | |
| WO | 2019212950 A1 | 11/2019 | |
| WO | 2019212952 A1 | 11/2019 | |
| WO | 2019212954 A1 | 11/2019 | |
| WO | 2019212956 A1 | 11/2019 | |
| WO | 2019214787 A1 | 11/2019 | |
| WO | 2019214788 A1 | 11/2019 | |
| WO | 2019226826 A1 | 11/2019 | |
| WO | WO-2019212951 A1 * | 11/2019 | A61F 5/4401 |
| WO | WO-2019212955 A1 * | 11/2019 | A61F 5/44 |
| WO | 2019239433 A1 | 12/2019 | |
| WO | 2020000994 A1 | 1/2020 | |
| WO | 2020020618 A1 | 1/2020 | |
| WO | 2020033752 A1 | 2/2020 | |
| WO | 2020038822 A1 | 2/2020 | |
| WO | 2020088409 A1 | 5/2020 | |
| WO | 2020049394 A3 | 6/2020 | |
| WO | 2020120657 A1 | 6/2020 | |
| WO | 2020152575 A1 | 7/2020 | |
| WO | 2020182923 A1 | 9/2020 | |
| WO | 2020204967 A1 | 10/2020 | |
| WO | 2020205939 A1 | 10/2020 | |
| WO | 2020209898 A1 | 10/2020 | |
| WO | 2020242790 A1 | 12/2020 | |
| WO | 2020251893 A1 | 12/2020 | |
| WO | 2020256865 A1 | 12/2020 | |
| WO | 2021007144 A1 | 1/2021 | |
| WO | 2021007345 A1 | 1/2021 | |
| WO | 2021010844 A1 | 1/2021 | |
| WO | 2021016026 A1 | 1/2021 | |
| WO | 2021016056 A1 | 1/2021 | |
| WO | 2021016300 A1 | 1/2021 | |
| WO | 2021025919 A1 | 2/2021 | |
| WO | 2021034886 A1 | 2/2021 | |
| WO | 2021041123 A1 | 3/2021 | |
| WO | 2021046501 A1 | 3/2021 | |
| WO | 2021086868 A1 | 5/2021 | |
| WO | 2021094352 A1 | 5/2021 | |
| WO | 2021094639 A1 | 5/2021 | |
| WO | 2021097067 A1 | 5/2021 | |
| WO | 2021102296 A1 | 5/2021 | |
| WO | 2021107025 A1 | 6/2021 | |
| WO | 2021138411 A1 | 7/2021 | |
| WO | 2021138414 A1 | 7/2021 | |
| WO | 2021154686 A1 | 8/2021 | |
| WO | 2021155206 A1 | 8/2021 | |
| WO | 2021170075 A1 | 9/2021 | |
| WO | 2021173436 A1 | 9/2021 | |
| WO | 2021188817 A1 | 9/2021 | |
| WO | 2021195384 A1 | 9/2021 | |
| WO | 2021205995 A1 | 10/2021 | |
| WO | 2021207621 A1 | 10/2021 | |
| WO | 2021211568 A1 | 10/2021 | |
| WO | 2021211801 A1 | 10/2021 | |
| WO | 2021211914 A1 | 10/2021 | |
| WO | 2021216419 A1 | 10/2021 | |
| WO | 2021216422 A1 | 10/2021 | |
| WO | 2021231532 A1 | 11/2021 | |
| WO | 2021247523 A1 | 12/2021 | |
| WO | 2021257202 A1 | 12/2021 | |
| WO | 2022006256 A1 | 1/2022 | |
| WO | 2022029662 A1 | 2/2022 | |
| WO | 2022031943 A1 | 2/2022 | |
| WO | 2022035745 A1 | 2/2022 | |
| WO | 2022051220 A1 | 3/2022 | |
| WO | 2022051360 A1 | 3/2022 | |
| WO | 2022054613 A1 | 3/2022 | |
| WO | 2022066704 A1 | 3/2022 | |
| WO | 2022067392 A1 | 4/2022 | |
| WO | 2022069950 A1 | 4/2022 | |
| WO | 2022071429 A1 | 4/2022 | |
| WO | 2022076322 A1 | 4/2022 | |
| WO | 2022076427 A2 | 4/2022 | |
| WO | 2022086898 A1 | 4/2022 | |

(56) References Cited

FOREIGN PATENT DOCUMENTS

| | | |
|---|---|---|
| WO | 2022090199 A1 | 5/2022 |
| WO | 2022098536 A1 | 5/2022 |
| WO | 2022099087 A1 | 5/2022 |
| WO | 2022101999 A1 | 5/2022 |
| WO | 2022115692 A1 | 6/2022 |
| WO | 2022125685 A1 | 6/2022 |
| WO | 2022140545 A1 | 6/2022 |
| WO | 2022145231 A1 | 7/2022 |
| WO | 2022150290 A1 | 7/2022 |
| WO | 2022150360 A1 | 7/2022 |
| WO | 2022150463 A1 | 7/2022 |
| WO | 2022159392 A1 | 7/2022 |
| WO | 2022170182 A1 | 8/2022 |
| WO | 2022173803 A1 | 8/2022 |
| WO | 2022182385 A1 | 9/2022 |
| WO | 2022187152 A1 | 9/2022 |
| WO | 2022192188 A1 | 9/2022 |
| WO | 2022192347 A1 | 9/2022 |
| WO | 2022204000 A1 | 9/2022 |
| WO | 2022216507 A1 | 10/2022 |
| WO | 2022216776 A1 | 10/2022 |
| WO | 2022222030 A1 | 10/2022 |
| WO | 2022251184 A1 | 12/2022 |
| WO | 2022251425 A1 | 12/2022 |
| WO | 2022271783 A1 | 12/2022 |
| WO | 2023286058 A1 | 1/2023 |
| WO | 2023014639 A1 | 2/2023 |
| WO | 2023014641 A1 | 2/2023 |
| WO | 2023018475 A2 | 2/2023 |
| WO | 2023018656 A1 | 2/2023 |
| WO | 2023018657 A1 | 2/2023 |
| WO | 2023023777 A1 | 3/2023 |
| WO | 2023034139 A1 | 3/2023 |
| WO | 2023034453 A1 | 3/2023 |
| WO | 2023038945 A1 | 3/2023 |
| WO | 2023038950 A1 | 3/2023 |
| WO | 2023049109 A1 | 3/2023 |
| WO | 2023049156 A1 | 3/2023 |
| WO | 2023049175 A1 | 3/2023 |
| WO | 2023086394 A1 | 5/2023 |
| WO | 2023149884 A1 | 8/2023 |
| WO | 2023149902 A1 | 8/2023 |
| WO | 2023149903 A1 | 8/2023 |
| WO | 2023154390 A1 | 8/2023 |
| WO | 2023163725 A1 | 8/2023 |
| WO | 2023191764 A1 | 10/2023 |
| WO | 2023244238 A1 | 12/2023 |
| WO | 2024043871 A1 | 2/2024 |
| WO | 2024058788 A1 | 3/2024 |
| WO | 2024253655 A1 | 12/2024 |
| WO | 2025034959 A1 | 2/2025 |
| WO | 2025038087 A1 | 2/2025 |
| WO | 2025038088 A1 | 2/2025 |
| WO | 2025071622 A1 | 4/2025 |

OTHER PUBLICATIONS

Britannica, T. Editors of Encyclopaedia (Jul. 26, 2012). polyolefin. Encyclopedia Britannica. https://www.britannica.com/science/polyolefin (Year: 2012).*
Timmins, Peter, Samuel R Pygall, and Colin D Melia. "Chapter 5 Applications of Polyethylene Oxide (POLYOX) in Hydrophilic Matrices." Hydrophilic Matrix Tablets for Oral Controlled Release. vol. 16. United States: Springer, 2014. 123-141. Web. (Year: 2014).*
Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.

(56)                    References Cited

OTHER PUBLICATIONS

Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/899,956 mailed Oct. 16, 2020.
Non-Final Office Action for U.S. Appl. No. 16/904,868 mailed Nov. 25, 2020.
Non-Final Office Action for U.S. Appl. No. 16/905,400 mailed Dec. 2, 2020.
Non-Final Office Action for U.S. Appl. No. 17/088,272 mailed Jan. 25, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Jan. 29, 2021.
Notice of Allowance for U.S. Appl. No. 29/694,002 mailed Oct. 16, 2020.
Notice to File Missing Parts for U.S. Appl. No. 17/179,116 mailed Mar. 3, 2021.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/611,587, filed Jun. 1, 2017.
U.S. Appl. No. 15/612,325, filed Jun. 2, 2017.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/088,272, filed Nov. 3, 2020.
U.S. Appl. No. 17/179,116, filed Feb. 18, 2021.
U.S. Appl. No. 29/741,751, filed Jul. 15, 2020.
U.S. Appl. No. 62/452,437, filed Jan. 31, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,889, filed May 29, 2019.
U.S. Appl. No. 62/873,045, filed Jul. 11, 2019.
U.S. Appl. No. 62/873,048, filed Jul. 11, 2019.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/071,438, filed Aug. 28, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/094,464, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
Defendant and Counterclaim Plaintiff Sage Products, LLC's Answer, Defenses, and Counterclaims to Plaintiff's Amended Complaint, Nov. 1, 2019.
Memorandum Order, Feb. 2021, 14 pgs.
Sage's Initial Invalidity Contentions Regarding U.S. Pat. Nos. 8,287,508; 10,226,375; and 10,390,989, May 29, 2020, 193 pages.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Sage's Second Supplemental Invalidity Contentions Regarding U.S. Pat. Nos. 8,287,508, 10,226,375, 10,390,989, and 10,376,407, 292 pages.
Excerpts from the 508 (U.S. Pat. No. 8,278,508) Patent's Prosecution History, 2020, 99 pages.
Plaintiff's Opening Claim Construction Brief, Case No. 19-1508-MN, Oct. 16, 2020, 26 pages.
Plaintiff's Identification of Claim Terms and Proposed Constructions, Case No. 19-1508-MN, 3 pages.
PureWick's Response to Interrogatory No. 9 in *PureWick, LLC* v. *Sage Products, LLC*, Case No. 19-1508-MN, Mar. 23, 2020, 6 pages.
Sage's Preliminary Identification of Claim Elements and Proposed Constructions for U.S. Pat. Nos. 8,287,508, 10,226,376, 10,390,989 and 10,376,407, Case No. 19-1508-MN, 7 pages.
Decision Granting Institution of Inter Partes Review for U.S. Pat. No. 8,287,508, Case No. 2020-01426, Feb. 17, 2021, 39 pages.
Corrected Certificate of Service, Case No. IPR2020-01426, Patent No. 8,287,508, 2020, 2 pages.

(56) References Cited

OTHER PUBLICATIONS

Declaration of Diane K. Newman Curriculum Vitae, Petition for Interparties Review, 2020, pp. 1-199.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, Omni Medical, 8 pages.
"AMXDmax In-Flight Bladder Relief", Omni Medical; Omni Medical Systems, Inc., 2015.
"AMXDX—Advanced Mission Extender Device Brochure", Omni Medical, Omni Brochure - http://www.omnimedicalsys.com/uploads/AMXDFixedWing.pdf, 2 pages.
"How Period Panties Work", www.shethinx.com/pages/thinx-itworks, 2020, 10 pages.
"In Flight Bladder Relief", Omni Medical, Omni Presentation https://www.omnimedicalsys.com/uploads/AMXDmax_HSD.pdf, 14 pages.
"Research and Development Work Relating to Assistive Technology Jun. 2005", British Department of Health, Nov. 2006, 40 pages.
"Step by Step How Ur24 WorksHome", http://medicalpatentur24.com, last accessed Dec. 6, 2017, Aug. 30, 2017, 4 pages.
"Underwear that absorbs your period", Thinx!, https://www.shethinx.com/pages/thinx-it-works last accessed Jun. 24, 2020, 7 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, MD&DI, 2014, 4 pages.
Hollister, Female Urinary and Pouch and Male Urinary Pouch Brochure, 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device, last accessed Feb. 8, 2018.
Hollister, "Retracted Penis Pouch by Hollister", Vitality Medical.com, https://www.vitalitymedical.com/hollister-retracted-penis-pouch.html last accessed Jun. 24, 2020, 6 pages.
Macaulay, et al., "A Noninvasive Continence Management System: Development and Evaluation of a Novel Toileting Device for Women", The Wound, Ostomy and Continence Nurses Society, vol. 34 No. 6, 2007, pp. 641-648.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", Jan. 8, 2016, 11 pages.
Parmar, "10 Finalists Chosen for Dare-to-Dream Medtech Design Challenge (PureWick)", Design Services, Nov. 10, 2014, 3 pages.
Purewick, "Incontinence Relief for Women", Presentation, Sep. 23, 2015, 7 pages.
Pytlik, "Super Absorbent Polymers", University of Buffalo, http://www.courses.sens.buffalo.edu/ce435/Diapers/Diapers.html, accessed on Feb. 17, 2017.
Sachtman, "New Relief for Pilots? It Depends", Wired, https://www.wired.com/2008/05/pilot-relief/, 2008, 2 pages.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
Issue Notification for U.S. Appl. No. 15/612,325 mailed Mar. 24, 2021.
Non-Final Office Action for U.S. Appl. No. 14/592,591 mailed Mar. 20, 2020.
U.S. Appl. No. 62/853,279 filed at 28, 2019.
U.S. Appl. No. 62/864,656, filed Jun. 21, 2019.
U.S. Appl. No. 62/876,500, filed Jul. 19, 2019.
U.S. Appl. No. 62/883,172, filed Aug. 6, 2019.
U.S. Appl. No. 62/877,558, filed Jul. 23, 2019.
U.S. Appl. No. 62/889,149, filed Aug. 20, 2019.
U.S. Appl. No. 63/094,498, filed Oct. 21, 2020.
U.S. Appl. No. 63/109,066, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/146,946, filed Feb. 8, 2021.
U.S. Appl. No. 63/147,299, filed Feb. 9, 2021.
U.S. Appl. No. 63/165,273, filed Mar. 24, 2021.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Feb. 15, 2023.
Advisory Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/478,180 mailed Sep. 7, 2023.
Advisory Action for U.S. Appl. No. 16/899,956 mailed Jul. 9, 2021.
Advisory Action for U.S. Appl. No. 16/904,868 mailed Jul. 2, 2021 ,.
Advisory Action for U.S. Appl. No. 16/904,868 mailed Jun. 15, 2022 m.
Advisory Action for U.S. Appl. No. 16/905,400 mailed Feb. 16, 2022.
Advisory Action for U.S. Appl. No. 16/905,400 mailed Jun. 9, 2021.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/444,792 mailed Aug. 25, 2023.
Advisory Action for U.S. Appl. No. 17/451,345 mailed Oct. 20, 2023.
Advisory Action for U.S. Appl. No. 17/662,700 mailed Jan. 30, 2023.
Corrected Notice of Allowability for U.S. Appl. No. 17/330,657 mailed Dec. 9, 2021.
Final Office Action for U.S. Appl. No. 16/245,726 mailed Nov. 25, 2022.

(56)     References Cited

OTHER PUBLICATIONS

Final Office Action for U.S. Appl. No. 16/369,676 mailed Aug. 31, 2023.
Final Office Action for U.S. Appl. No. 16/369,676 mailed Dec. 5, 2022.
Final Office Action for U.S. Appl. No. 16/433,773 mailed Oct. 10, 2023.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/452,145 mailed Mar. 25, 2022.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/478,180 mailed May 31, 2023.
Final Office Action for U.S. Appl. No. 16/899,956 mailed Apr. 19, 2021.
Final Office Action for U.S. Appl. No. 16/904,868 mailed Mar. 10, 2022.
Final Office Action for U.S. Appl. No. 16/904,868 mailed Mar. 26, 2021.
Final Office Action for U.S. Appl. No. 16/904,868 mailed Nov. 2, 2023.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/088,272 mailed May 25, 2021.
Final Office Action for U.S. Appl. No. 17/179,116 mailed Oct. 31, 2023.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/448,811 mailed Aug. 3, 2023.
Final Office Action for U.S. Appl. No. 17/451,345 mailed May 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/662,700 mailed Sep. 30, 2022.
International Search Report and Written Opinion from International Application No. PCT/IB2021/057173 mailed Nov. 5, 2021.
International Search Report and Written Opinion from International Application No. PCT/US2020/057562 mailed Jan. 27, 2021.
International Search Report and Written Opinion from International Application No. PCT/US2020/061563 mailed Feb. 19, 2021.
International Search Report and Written Opinion from International Application No. PCT/US2020/065234 mailed Apr. 12, 2021.

International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/039866 mailed Oct. 7, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.

(56)  References Cited

OTHER PUBLICATIONS

International Search Report and Written Opinion from International Application No. PCT/US2022/015026 mailed Oct. 31, 2022.

International Search Report and Written Opinion from International Application No. PCT/US2022/015045 mailed Sep. 9, 2022.

International Search Report and Written Opinion from International Application No. PCT/US2022/015073 mailed Sep. 8, 2022.

International Search Report and Written Opinion from International Application No. PCT/US2022/015418 mailed Nov. 11, 2022.

International Search Report and Written Opinion from International Application No. PCT/US2022/015420 mailed Nov. 18, 2022.

International Search Report and Written Opinion from International Application No. PCT/US2022/015471 mailed May 16, 2022.

International Search Report and Written Opinion from International Application No. PCT/US2022/015492 mailed Apr. 26, 2022.

International Search Report and Written Opinion from International Application No. PCT/US2022/015781 mailed May 6, 2022.

International Search Report and Written Opinion from International Application No. PCT/US2022/016942 mailed Jun. 8, 2022.

International Search Report and Written Opinion from International Application No. PCT/US2022/018159 mailed Dec. 12, 2022.

International Search Report and Written Opinion from International Application No. PCT/US2022/018170 mailed May 31, 2022.

International Search Report and Written Opinion from International Application No. PCT/US2022/019254 mailed Jun. 7, 2022.

International Search Report and Written Opinion from International Application No. PCT/US2022/019480 mailed Jun. 13, 2022.

International Search Report and Written Opinion from International Application No. PCT/US2022/021103 mailed Jun. 23, 2022.

International Search Report and Written Opinion from International Application No. PCT/US2022/022111 mailed Oct. 26, 2022.

International Search Report and Written Opinion from International Application No. PCT/US2022/023594 mailed Jul. 12, 2022.

International Search Report and Written Opinion from International Application No. PCT/US2022/026667 mailed Aug. 22, 2022.

International Search Report and Written Opinion from International Application No. PCT/US2022/030685 mailed Oct. 31, 2022.

International Search Report and Written Opinion from International Application No. PCT/US2022/031032 mailed Sep. 9, 2022.

International Search Report and Written Opinion from International Application No. PCT/US2022/032424 mailed Oct. 11, 2022.

International Search Report and Written Opinion from International Application No. PCT/US2022/034457 mailed Oct. 12, 2022.

International Search Report and Written Opinion from International Application No. PCT/US2022/034744 mailed Dec. 9, 2022.

International Search Report and Written Opinion from International Application No. PCT/US2022/039018 mailed Jan. 10, 2023.

International Search Report and Written Opinion from International Application No. PCT/US2022/039022 mailed Jan. 10, 2023.

International Search Report and Written Opinion from International Application No. PCT/US2022/039711 mailed Jan. 12, 2023.

International Search Report and Written Opinion from International Application No. PCT/US2022/039714 mailed Nov. 22, 2022.

International Search Report and Written Opinion from International Application No. PCT/US2022/041085 mailed Mar. 16, 2023.

International Search Report and Written Opinion from International Application No. PCT/US2022/041688 mailed Nov. 21, 2022.

International Search Report and Written Opinion from International Application No. PCT/US2022/042719 mailed Dec. 5, 2022.

International Search Report and Written Opinion from International Application No. PCT/US2022/042725 mailed Dec. 19, 2022.

International Search Report and Written Opinion from International Application No. PCT/US2022/043818 mailed Mar. 24, 2023.

International Search Report and Written Opinion from International Application No. PCT/US2022/044107 mailed Dec. 23, 2022.

International Search Report and Written Opinion from International Application No. PCT/US2022/044208 mailed May 8, 2023.

International Search Report and Written Opinion from International Application No. PCT/US2022/044212 mailed Jan. 20, 2023.

International Search Report and Written Opinion from International Application No. PCT/US2022/044243 mailed Feb. 24, 2023.

International Search Report and Written Opinion from International Application No. PCT/US2022/049300 mailed Jun. 6, 2023.

International Search Report and Written Opinion from International Application No. PCT/US2022/050909 mailed Jul. 24, 2023.

International Search Report and Written Opinion from International Application No. PCT/US2023/012696 mailed Jul. 6, 2023.

International Search Report and Written Opinion from International Application No. PCT/US2023/018474 mailed Sep. 11, 2023.

Issue Notification for U.S. Appl. No. 14/952,591 mailed Jul. 28, 2021.

Issue Notification for U.S. Appl. No. 16/245,726 mailed Oct. 18, 2023.

Issue Notification for U.S. Appl. No. 16/899,956 mailed Mar. 29, 2023.

Issue Notification for U.S. Appl. No. 16/905,400 mailed Nov. 30, 2022.

Issue Notification for U.S. Appl. No. 17/088,272 mailed Jun. 15, 2022.

Issue Notification for U.S. Appl. No. 17/330,657 mailed Jun. 22, 2022.

Issue Notification for U.S. Appl. No. 17/461,036 mailed Oct. 11, 2023.

Issue Notification for U.S. Appl. No. 29/624,661 mailed Aug. 4, 2021.

Non-Final Office Action for U.S. Appl. No. 16/245,726 mailed Jan. 21, 2022.

Non-Final Office Action for U.S. Appl. No. 16/369,676 mailed Mar. 31, 2022.

Non-Final Office Action for U.S. Appl. No. 16/433,773 mailed Apr. 11, 2023.

Non-Final Office Action for U.S. Appl. No. 16/433,773 mailed Apr. 21, 2022.

Non-Final Office Action for U.S. Appl. No. 16/449,039 mailed Apr. 27, 2023.

Non-Final Office Action for U.S. Appl. No. 16/449,039 mailed Dec. 8, 2021.

Non-Final Office Action for U.S. Appl. No. 16/452,145 mailed Mar. 28, 2023.

Non-Final Office Action for U.S. Appl. No. 16/452,145 mailed Nov. 2, 2023.

Non-Final Office Action for U.S. Appl. No. 16/452,145 mailed Sep. 28, 2021.

Non-Final Office Action for U.S. Appl. No. 16/452,258 mailed Apr. 26, 2023.

Non-Final Office Action for U.S. Appl. No. 16/452,258 mailed Sep. 28, 2021.

Non-Final Office Action for U.S. Appl. No. 16/478,180 mailed Dec. 20, 2022.

Non-Final Office Action for U.S. Appl. No. 16/478,180 mailed Nov. 7, 2023.

Non-Final Office Action for U.S. Appl. No. 16/478,180 mailed Oct. 22, 2021.

Non-Final Office Action for U.S. Appl. No. 16/899,956 mailed Sep. 2, 2021.

Non-Final Office Action for U.S. Appl. No. 16/904,868 mailed Mar. 15, 2023.

Non-Final Office Action for U.S. Appl. No. 16/904,868 mailed Oct. 5, 2021.

Non-Final Office Action for U.S. Appl. No. 16/905,400 mailed Apr. 27, 2022.

Non-Final Office Action for U.S. Appl. No. 16/905,400 mailed Jul. 22, 2021.

Non-Final Office Action for U.S. Appl. No. 17/051,399 mailed Aug. 18, 2023.

Non-Final Office Action for U.S. Appl. No. 17/051,550 mailed Dec. 15, 2022.

Non-Final Office Action for U.S. Appl. No. 17/051,550 mailed Oct. 24, 2023.

Non-Final Office Action for U.S. Appl. No. 17/051,585 mailed Mar. 29, 2023.

(56) References Cited

OTHER PUBLICATIONS

Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/330,657 mailed Aug. 11, 2021.
Non-Final Office Action for U.S. Appl. No. 17/444,792 mailed Feb. 10, 2023.
Non-Final Office Action for U.S. Appl. No. 17/446,256 mailed Apr. 13, 2023.
Non-Final Office Action for U.S. Appl. No. 17/446,654 mailed Sep. 8, 2023.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/451,345 mailed Dec. 7, 2022.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/453,560 mailed Oct. 16, 2023.
Non-Final Office Action for U.S. Appl. No. 17/501,591 mailed Apr. 25, 2023.
Non-Final Office Action for U.S. Appl. No. 17/645,821 mailed Oct. 25, 2023.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/655,464 mailed Mar. 14, 2023.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/662,700 mailed Jul. 22, 2022.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 18/139,523 mailed Aug. 17, 2023.
Non-Final Office Action for U.S. Appl. No. 18/140,163 mailed Nov. 9, 2023.
Non-Final Office Action for U.S. Appl. No. 18/140,751 mailed Sep. 14, 2023.
Non-Final Office Action for U.S. Appl. No. 29/741,751 mailed Jan. 18, 2022.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 16/245,726 mailed Jul. 6, 2023.
Notice of Allowance for U.S. Appl. No. 16/369,676 mailed Nov. 14, 2023.
Notice of Allowance for U.S. Appl. No. 16/449,039 mailed Dec. 15, 2022.
Notice of Allowance for U.S. Appl. No. 16/899,956 mailed Apr. 19, 2022.
Notice of Allowance for U.S. Appl. No. 16/899,956 mailed Aug. 10, 2022.
Notice of Allowance for U.S. Appl. No. 16/899,956 mailed Dec. 1, 2022.

Notice of Allowance for U.S. Appl. No. 16/899,956 mailed Dec. 29, 2021.
Notice of Allowance for U.S. Appl. No. 16/905,400 mailed Aug. 17, 2022.
Notice of Allowance for U.S. Appl. No. 17/051,554 mailed Jul. 6, 2023.
Notice of Allowance for U.S. Appl. No. 17/051,554 mailed Oct. 18, 2023.
Notice of Allowance for U.S. Appl. No. 17/088,272 mailed Aug. 5, 2021.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/461,036 mailed Oct. 6, 2022.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 17/663,046 mailed Jan. 30, 2023.
Notice of Allowance for U.S. Appl. No. 18/299,788 mailed Jul. 24, 2023.
Notice of Allowance for U.S. Appl. No. 18/299,788 mailed Nov. 6, 2023.
Notice of Allowance for U.S. Appl. No. 29/624,661 mailed Apr. 28, 2021.
Notice of Allowance for U.S. Appl. No. 29/694,002 mailed Apr. 29, 2021.
Notice of Allowance for U.S. Appl. No. 29/741,751 mailed Jun. 9, 2022.
Restriction Requirement for U.S. Appl. No. 16/433,773 mailed Dec. 7, 2021.
Restriction Requirement for U.S. Appl. No. 16/478,180 mailed May 25, 2021.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Restriction Requirement for U.S. Appl. No. 18/134,857 mailed Oct. 23, 2023.
Text Messages to Lorena Eckert Re Prototype PureWick Holder dated Apr. 16, 2022.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/384,196, filed Dec. 19, 2016.
U.S. Appl. No. 16/245,726, filed Jan. 11, 2019.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.

(56) References Cited

OTHER PUBLICATIONS

U.S. Appl. No. 17/451,345, filed Oct. 19, 2021.
U.S. Appl. No. 17/451,354, filed Oct. 19, 2021.
U.S. Appl. No. 17/451,719, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,487, filed May 23, 2022.
U.S. Appl. No. 17/664,914, filed May 25, 2022.
U.S. Appl. No. 17/749,340, filed May 20, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/485,578, filed Apr. 14, 2017.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. App. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,158, filed Jan. 26, 2020.
U.S. Appl. No. 62/967,977, filed Jan. 30, 2020.
U.S. Appl. No. 62/991,754, filed Mar. 19, 2020.
U.S. Appl. No. 63/008,112, filed Apr. 10, 2020.
U.S. Appl. No. 63/030,685, filed May 27, 2020.
U.S. Appl. No. 63/047,374, filed Jul. 2, 2020.
U.S. Appl. No. 63/067,542, filed Aug. 19, 2020.
U.S. Appl. No. 63/073,545, filed Sep. 2, 2020.
U.S. Appl. No. 63/073,553, filed Sep. 2, 2020.
U.S. Appl. No. 63/094,646, filed Oct. 21, 2020.
U.S. Appl. No. 63/109,084, filed Nov. 3, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/147,013, filed Feb. 8, 2021.
U.S. Appl. No. 63/148,723, filed Feb. 12, 2021.
U.S. Appl. No. 63/150,640, filed Feb. 18, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/191,558, filed May 21, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,328, filed Sep. 7, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.

(56)　　　　　References Cited

OTHER PUBLICATIONS

U.S. Appl. No. 63/299,208, filed Jan. 13, 2022.
U.S. Appl. No. 63/308,190, filed Feb. 9, 2022.
U.S. Appl. No. 63/596,012, filed Nov. 3, 2023.
*PureWick Corporation* v. *Sage Products, LLC* Transcripts vol. 2 , Mar. 29, 2022.
*PureWick Corporation* v. *Sage Products, LLC* Transcripts vol. 3 , Mar. 30, 2022.
*PureWick Corporation* v. *Sage Products, LLC* Transcripts vol. 4 , Mar. 31, 2022.
Boehringer CareDry System—Second Generation for Non-Invasive Urinary Management for Females , Mar. 2021.
*PureWick Corporation* v. *Sage Products, LLC* Transcripts vol. 5 , Apr. 1, 2022.
*PureWick Corporation* v. *Sage Products, LLC* Transcripts vol. 1 , Mar. 28, 2022.
"AMXD Control Starter Kit" , Omni Medical Systems, Inc. , 1 page.
"AMXDmax Advanced Mission Extender Device User & Maintenance Guide" , Omni Medical , Jan. 11, 2010 , 10 pages.
"AMXDmax Development History 2002-2014" , Omni Medical Systems, Inc. , 2 pages.
"Combat Force Multiplier in Flight Bladder Relief Cockpit Essential Equipment Brochure" , Omni Medical , 20 pages.
"GSA Price List" , Omni Medical , Apr. 2011 , 2 pages.
"How is Polypropylene Fiber Made" , https:www.yarnsandfibers.com/textile-resources/synthetic-fibers/polypropylene-fiber/polypropylene-fiber-production-raw-materials/how-is-polypropylene-fiber-made/ last accessed 2020 , Oct. 7, 2020 , 3 pages.
"Letter to Mark Harvie of Omni Measurement Systems" , Department of Veterans Affairs , Nov. 1, 2007 , 11 pages.
"Revised AMXDmax Advanced Mission Extender Device User & Maintenance Guide" , Omni Medical Systems , Oct. 8, 2019 , 52 pages.
"Rising Warrior Insulated Gallon Jug Cover" , https://www.amazon.com/Rising-Warrior-Insulated-Sleeve , 2021 , 2 pages.
"Urine Bag Cover-Catheter Bag Cover 2000 ml Volume-Medline Style-Multiple Sclerosis-Spine Injury-Suprapublic Catheter-Bladder Incontinence" , https://www.etsy.com/listing/1142934658/urine-bag-cover-caatheter-bag-cover-2000 , 2022 , 1 page.
"Vinyl Dust Cover, Janome #741811000, Janome, Sewing Parts Online" , https://www.sewingpartsonline.com/vinyl-dust-cover-janome-74181000 , 2020 , 2 pages.
Ali , "Sustainability Assessment: Seventh Generation Diapers versus gDiapers" , The University of Vermont , Dec. 6, 2011 , pp. 1-31.
Autumn , et al. , "Frictional adhesion: a new angle on gecko attachment" , The Journal of Experimental Biology , 2006 , pp. 3569-3579.
Cañas , et al. , "Effect of nano- and micro-roughness on adhesion of bioinspired micropatterned surfaces" , Acta Biomaterialia 8 , 2012 , pp. 282-288.
Chaudhary , et al. , "Bioinspired dry adhesive: Poly(dimethylsiloxane) grafted with poly(2-ethylhexyl acrylate) brushes" , European Polymer Journal , 2015 , pp. 432-440.
Dai , et al. , "Non-sticky and Non-slippery Biomimetic Patterned Surfaces" , Journal of Bionic Engineering , Mar. 2020 , pp. 326-334.
Espinoza-Ramirez , "Nanobiodiversity and Biomimetic Adhesives Development: From Nature to Production and Application" , Journal of Biomaterials and Nanobiotechnology , pp. 78-101 , 2019.
Hwang , et al. , "Multifunctional Smart Skin Adhesive Patches for Advanced Health Care" , Adv. Healthcare Mater , 2018 , pp. 1-20.
Jagota , et al. , "Adhesion, friction, and compliance of bio-mimetic and bio-inspired structured interfaces" , Materials Science and Engineering , 2011 , pp. 253-292.
Jeong , et al. , "A nontransferring dry adhesive with hierarchical polymer nanohairs" , PNAS , Apr. 7, 2009 , pp. 5639-5644.
Jeong , et al. , "Nanohairs and nanotubes: Efficient structural elements for gecko-inspired artificial dry adhesives" , Science Direct , 2009 , pp. 335-346.
Karp , et al. , "Dry solution to a sticky problem" , Nature. , 2011 , pp. 42-43.

Lee , et al. , "Continuous Fabrication of Wide-Tip Microstructures for Bio-Inspired Dry Adhesives via Tip Inking Process" , Journal of Chemistry , Jan. 2, 2019 , pp. 1-5.
Merriam-Webster Dictionary, , "Embed Definition & Meaning" , https://www.merriam-webster.com/dictionary/embed last accessed Aug. 3, 2023 , 2003.
Parness , et al. , "A microfabricated wedge-shaped adhesive array displaying gecko-like dynamic adhesion, directionality" , J.R. Soc. Interface , 2009 , pp. 1223-1232.
Pieper , et al. , "An external urine-collection device for women: A clinical trial" , Journal of ER Nursing, vol. 20, No. 2 , Mar./Apr. 1993 , pp. 51-55.
Tsipenyuk , et al. , "Use of biomimetic hexagonal surface texture in friction against lubricated skin", Journal of The Royal Society—Interface , 2014 , pp. 1-6.
Vinas , "A Solution for an Awkward—But Serious—Subject" , http://www.aero-news.net/index.cfm?do=main.textpost&id=69ae2bb1-838b-4098-a7b5-7flbb2505688 last accessed Feb. 8, 2021.
Advisory Action for U.S. Appl. No. 16/433,773 mailed Dec. 29, 2023.
Advisory Action for U.S. Appl. No. 16/449,039 mailed Jan. 25, 2024.
Advisory Action for U.S. Appl. No. 16/452,258 mailed Apr. 8, 2024.
Advisory Action for U.S. Appl. No. 16/904,868 mailed Jan. 2, 2024.
Advisory Action for U.S. Appl. No. 17/179,116 mailed Jan. 8, 2024.
Advisory Action for U.S. Appl. No. 17/446,256 mailed Dec. 8, 2023.
Advisory Action for U.S. Appl. No. 17/446,654 mailed Apr. 15, 2024.
Advisory Action for U.S. Appl. No. 17/450,864 mailed Mar. 21, 2024.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/646,771 mailed Feb. 29, 2024.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 18/139,523 mailed Apr. 24, 2024.
Advisory Action for U.S. Appl. No. 18/140,751 mailed Apr. 24, 2024.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Corrected Notice of Allowability for U.S. Appl. No. 17/657,474 mailed Mar. 13, 2024.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/478,180 mailed Feb. 28, 2024.
Final Office Action for U.S. Appl. No. 17/051,399 mailed Jan. 8, 2024.
Final Office Action for U.S. Appl. No. 17/444,792 mailed Apr. 3, 2024.

(56) References Cited

OTHER PUBLICATIONS

Final Office Action for U.S. Appl. No. 17/446,654 mailed Jan. 31, 2024.

Final Office Action for U.S. Appl. No. 17/450,864 mailed Dec. 28, 2023.

Final Office Action for U.S. Appl. No. 17/451,345 mailed Apr. 18, 2024.

Final Office Action for U.S. Appl. No. 17/645,821 mailed Apr. 3, 2024.

Final Office Action for U.S. Appl. No. 17/646,771 mailed Dec. 21, 2023.

Final Office Action for U.S. Appl. No. 17/661,090 mailed Dec. 11, 2023.

Final Office Action for U.S. Appl. No. 17/663,330 mailed Dec. 12, 2023.

Final Office Action for U.S. Appl. No. 17/664,487 mailed Jan. 4, 2024.

Final Office Action for U.S. Appl. No. 17/808,354 mailed Apr. 10, 2024.

Final Office Action for U.S. Appl. No. 18/139,523 mailed Dec. 22, 2023.

Final Office Action for U.S. Appl. No. 18/140,163 mailed Mar. 27, 2024.

Final Office Action for U.S. Appl. No. 18/140,751 mailed Jan. 17, 2024.

Final Office Action for U.S. Appl. No. 18/164,800 mailed Dec. 6, 2023.

International Search Report and Written Opinion from International Application No. PCT/US2023/024805 mailed Dec. 14, 2023.

International Search Report and Written Opinion from International Application No. PCT/US2023/025192 mailed Feb. 7, 2024.

International Search Report and Written Opinion from International Application No. PCT/US2023/025939 mailed Feb. 7, 2024.

International Search Report and Written Opinion from International Application No. PCT/US2023/030365 mailed Mar. 13, 2024.

International Search Report and Written Opinion from International Application No. PCT/US2023/030373 mailed Mar. 13, 2024.

International Search Report and Written Opinion from International Application No. PCT/US2023/031433 mailed Mar. 4, 2024.

International Search Report and Written Opinion from International Application No. PCT/US2023/031740 mailed Mar. 4, 2024.

Issue Notification for U.S. Appl. No. 17/051,550 mailed Mar. 13, 2024.

Issue Notification for U.S. Appl. No. 17/051,554 mailed Mar. 6, 2024.

Issue Notification for U.S. Appl. No. 17/663,046 mailed Dec. 20, 2023.

Issue Notification for U.S. Appl. No. 18/299,788 mailed Feb. 21, 2024.

Non-Final Office Action for U.S. Appl. No. 16/369,676 mailed Feb. 29, 2024.

Non-Final Office Action for U.S. Appl. No. 16/433,773 mailed Feb. 26, 2024.

Non-Final Office Action for U.S. Appl. No. 16/904,868 mailed Mar. 12, 2024.

Non-Final Office Action for U.S. Appl. No. 17/051,585 mailed Jan. 8, 2024.

Non-Final Office Action for U.S. Appl. No. 17/179,116 mailed Feb. 26, 2024.

Non-Final Office Action for U.S. Appl. No. 17/444,792 mailed Nov. 17, 2023.

Non-Final Office Action for U.S. Appl. No. 17/446,256 mailed Feb. 13, 2024.

Non-Final Office Action for U.S. Appl. No. 17/447,123 mailed Jan. 24, 2024.

Non-Final Office Action for U.S. Appl. No. 17/448,811 mailed Jan. 17, 2024.

Non-Final Office Action for U.S. Appl. No. 17/451,345 mailed Jan. 17, 2024.

Non-Final Office Action for U.S. Appl. No. 17/451,354 mailed Apr. 4, 2024.

Non-Final Office Action for U.S. Appl. No. 17/597,673 mailed Mar. 20, 2024.

Non-Final Office Action for U.S. Appl. No. 17/646,771 mailed Apr. 24, 2024.

Non-Final Office Action for U.S. Appl. No. 17/653,137 mailed Jan. 18, 2024.

Non-Final Office Action for U.S. Appl. No. 17/653,920 mailed Mar. 15, 2024.

Non-Final Office Action for U.S. Appl. No. 17/655,464 mailed Mar. 26, 2024.

Non-Final Office Action for U.S. Appl. No. 17/664,914 mailed Jan. 31, 2024.

Non-Final Office Action for U.S. Appl. No. 17/808,354 mailed Nov. 28, 2023.

Non-Final Office Action for U.S. Appl. No. 18/003,029 mailed Mar. 26, 2024.

Non-Final Office Action for U.S. Appl. No. 18/134,857 mailed Jan. 25, 2024.

Non-Final Office Action for U.S. Appl. No. 18/164,800 mailed Mar. 22, 2024.

Non-Final Office Action for U.S. Appl. No. 18/198,464 mailed Dec. 7, 2023.

Notice of Allowance for U.S. Appl. No. 16/449,039 mailed Mar. 28, 2024.

Notice of Allowance for U.S. Appl. No. 17/051,550 mailed Feb. 7, 2024.

Notice of Allowance for U.S. Appl. No. 17/326,980 mailed Apr. 5, 2024.

Notice of Allowance for U.S. Appl. No. 17/326,980 mailed Jan. 29, 2024.

Notice of Allowance for U.S. Appl. No. 17/453,260 mailed Apr. 8, 2024.

Notice of Allowance for U.S. Appl. No. 17/453,560 mailed Jan. 31, 2024.

Notice of Allowance for U.S. Appl. No. 17/657,474 mailed Mar. 5, 2024.

Notice of Allowance for U.S. Appl. No. 17/657,474 mailed May 2, 2024.

Notice of Allowance for U.S. Appl. No. 17/662,700 mailed Mar. 6, 2024.

Notice of Allowance for U.S. Appl. No. 18/198,464 mailed Apr. 17, 2024.

Restriction Requirement for U.S. Appl. No. 17/667,097 mailed Mar. 20, 2024.

Submission in Opposition Proceedings for European Application No. 17807547.9 filed Jan. 10, 2024.

Supplemental Notice of Allowance for U.S. Appl. No. 17/051,550 mailed Feb. 21, 2024.

Supplemental Notice of Allowance for U.S. Appl. No. 17/051,554 mailed Feb. 14, 2024.

U.S. Appl. No. 17/444,792, filed Aug. 10, 2021.

U.S. Appl. No. 18/249,577, filed Oct. 19, 2021.

U.S. Appl. No. 18/294,370, filed Feb. 1, 2024.

U.S. Appl. No. 18/294,403, filed Feb. 1, 2024.

U.S. Appl. No. 18/415,080, filed Jan. 17, 2024.

U.S. Appl. No. 18/426,795, filed Jan. 30, 2024.

U.S. Appl. No. 18/562,626, filed Nov. 20, 2023.

U.S. Appl. No. 18/563,672, filed Nov. 22, 2023.

U.S. Appl. No. 18/569,711, filed Dec. 13, 2023.

U.S. Appl. No. 18/569,778, filed Dec. 13, 2023.

U.S. Appl. No. 18/584,002, filed Feb. 22, 2024.

U.S. Appl. No. 18/610,523, filed Mar. 20, 2024.

U.S. Appl. No. 18/662,216, filed May 13, 2024.

U.S. Appl. No. 18/681,987, filed Feb. 7, 2024.

U.S. Appl. No. 18/682,006, filed Feb. 7, 2024.

U.S. Appl. No. 18/687,117, filed Feb. 27, 2024.

U.S. Appl. No. 18/688,023, filed Feb. 29, 2024.

U.S. Appl. No. 18/693,638, filed Mar. 20, 2024.

U.S. Appl. No. 18/694,090, filed Mar. 21, 2024.

U.S. Appl. No. 63/561,893, filed Dec. 11, 2023.

U.S. Appl. No. 63/608,553, filed Dec. 11, 2023.

(56) References Cited

OTHER PUBLICATIONS

Wikipedia Article, "Decibel", https://web.archive.org/web/2020041521917/https://en.wikipedia/org/wiki/Decibel last accessed Mar. 11, 2024, 21 pages.
Wikipedia Article, "Fiberglass", https://web.archive.org.web/20200309194847/https://en.wikipedia.org/wiki/Fiberglass last accessed Mar. 11, 2024.
Wikipedia Article, "Zylinder (Geometrie)", https://de.wikipedia.org/w/index.php?title=Zylinder (Geometrie)&oldid=154862081, version of Jun. 1, 2016, 7 pages.
Advisory Action for U.S. Appl. No. 16/452,258 mailed May 5, 2025.
Advisory Action for U.S. Appl. No. 16/478,180 mailed Jun. 7, 2024.
Advisory Action for U.S. Appl. No. 17/051,585 mailed Oct. 8, 2024.
Advisory Action for U.S. Appl. No. 17/444,792 mailed Jul. 8, 2024.
Advisory Action for U.S. Appl. No. 17/446,256 mailed Nov. 19, 2024.
Advisory Action for U.S. Appl. No. 17/446,654 mailed Feb. 28, 2025.
Advisory Action for U.S. Appl. No. 17/451,345 mailed Jul. 3, 2024.
Advisory Action for U.S. Appl. No. 17/451,345 mailed May 13, 2025.
Advisory Action for U.S. Appl. No. 17/595,747 mailed Mar. 17, 2025.
Advisory Action for U.S. Appl. No. 17/597,673 mailed Jan. 7, 2025.
Advisory Action for U.S. Appl. No. 17/645,821 mailed Jul. 2, 2024.
Advisory Action for U.S. Appl. No. 17/653,137 mailed Nov. 20, 2024.
Advisory Action for U.S. Appl. No. 17/653,314 mailed Apr. 8, 2025.
Advisory Action for U.S. Appl. No. 17/653,920 mailed Oct. 28, 2024.
Advisory Action for U.S. Appl. No. 17/655,464 mailed Feb. 25, 2025.
Advisory Action for U.S. Appl. No. 17/664,487 mailed Apr. 24, 2025.
Advisory Action for U.S. Appl. No. 17/808,354 mailed Jun. 12, 2024.
Advisory Action for U.S. Appl. No. 18/003,029 mailed Jan. 8, 2025.
Advisory Action for U.S. Appl. No. 18/134,857 mailed Oct. 23, 2024.
Advisory Action for U.S. Appl. No. 18/140,163 mailed Jun. 3, 2024.
Advisory Action for U.S. Appl. No. 18/164,800 mailed Jan. 8, 2025.
Corrected Notice of Allowability for U.S. Appl. No. 17/450,864 mailed Oct. 24, 2024.
Corrected Notice of Allowability for U.S. Appl. No. 17/501,591 mailed Aug. 9, 2024.
Corrected Notice of Allowability for U.S. Appl. No. 17/646,771 mailed Jan. 17, 2025.
Corrected Notice of Allowability for U.S. Appl. No. 17/657,474 mailed May 14, 2024.
Corrected Notice of Allowability for U.S. Appl. No. 17/664,914 mailed Aug. 9, 2024.
Corrected Notice of Allowability for U.S. Appl. No. 17/996,253 mailed Apr. 28, 2025.
Corrected Notice of Allowability for U.S. Appl. No. 18/134,857 mailed Mar. 14, 2025.
Corrected Notice of Allowability for U.S. Appl. No. 18/426,795 mailed Dec. 4, 2024.
Corrected Notice of Allowance for U.S. Appl. No. 17/444,792 mailed Jun. 24, 2025.
Final Office Action for U.S. Appl. No. 16/433,773 mailed Sep. 9, 2024.
Final Office Action for U.S. Appl. No. 16/452,258 mailed Jan. 6, 2025.
Final Office Action for U.S. Appl. No. 17/051,585 mailed Jul. 5, 2024.
Final Office Action for U.S. Appl. No. 17/378,015 mailed Jun. 18, 2025.
Final Office Action for U.S. Appl. No. 17/446,256 mailed Aug. 7, 2024.

Final Office Action for U.S. Appl. No. 17/446,256 mailed Jun. 11, 2025.
Final Office Action for U.S. Appl. No. 17/446,654 mailed Dec. 18, 2024.
Final Office Action for U.S. Appl. No. 17/447,123 mailed May 14, 2024.
Final Office Action for U.S. Appl. No. 17/451,345 mailed Feb. 6, 2025.
Final Office Action for U.S. Appl. No. 17/451,354 mailed Oct. 28, 2024.
Final Office Action for U.S. Appl. No. 17/595,747 mailed Dec. 12, 2024.
Final Office Action for U.S. Appl. No. 17/597,408 mailed Mar. 24, 2025.
Final Office Action for U.S. Appl. No. 17/597,673 mailed Oct. 22, 2024.
Final Office Action for U.S. Appl. No. 17/614,173 mailed May 20, 2025.
Final Office Action for U.S. Appl. No. 17/625,941 mailed Feb. 18, 2025.
Final Office Action for U.S. Appl. No. 17/628,411 mailed Apr. 30, 2025.
Final Office Action for U.S. Appl. No. 17/653,137 mailed Aug. 7, 2024.
Final Office Action for U.S. Appl. No. 17/653,137 mailed Jun. 25, 2025.
Final Office Action for U.S. Appl. No. 17/653,314 mailed Jan. 30, 2025.
Final Office Action for U.S. Appl. No. 17/653,920 mailed Apr. 24, 2025.
Final Office Action for U.S. Appl. No. 17/653,920 mailed Aug. 14, 2024.
Final Office Action for U.S. Appl. No. 17/655,464 mailed Nov. 29, 2024.
Final Office Action for U.S. Appl. No. 17/664,487 mailed Jan. 13, 2025.
Final Office Action for U.S. Appl. No. 17/757,311 mailed Mar. 31, 2025.
Final Office Action for U.S. Appl. No. 17/759,697 mailed Jun. 4, 2025.
Final Office Action for U.S. Appl. No. 17/808,354 mailed Jun. 13, 2025.
Final Office Action for U.S. Appl. No. 17/907,125 mailed Apr. 30, 2025.
Final Office Action for U.S. Appl. No. 18/003,029 mailed Oct. 22, 2024.
Final Office Action for U.S. Appl. No. 18/134,857 mailed Jul. 25, 2024.
Final Office Action for U.S. Appl. No. 18/139,523 mailed May 8, 2025.
Final Office Action for U.S. Appl. No. 18/164,800 mailed Oct. 22, 2024.
International Search Report and Written Opinion from International Application No. PCT/US2023/031432 mailed Feb. 29, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/036875 mailed May 31, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/077205 mailed Jul. 19, 2024.
International Search Report and Written Opinion from International Application No. PCT/US2023/077208 mailed May 10, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.

(56) References Cited

OTHER PUBLICATIONS

International Search Report and Written Opinion from International Application No. PCT/US2024/053681 mailed Jan. 27, 2025.
International Search Report and Written Opinion from International Application No. PCT/US2024/058598 mailed Mar. 28, 2025.
International Search Report and Written Opinion from International Application No. PCT/US2025/018907 mailed May 16, 2025.
International Search Report and Written Opinion from International Application No. PCT/US2025/018909 mailed May 20, 2025.
Issue Notification for U.S. Appl. No. 16/369,676 mailed Oct. 2, 2024.
Issue Notification for U.S. Appl. No. 16/449,039 mailed Jun. 19, 2024.
Issue Notification for U.S. Appl. No. 16/452,145 mailed Oct. 23, 2024.
Issue Notification for U.S. Appl. No. 16/478,180 mailed Mar. 5, 2025.
Issue Notification for U.S. Appl. No. 16/904,868 mailed Apr. 30, 2025.
Issue Notification for U.S. Appl. No. 17/051,585 mailed Mar. 26, 2025.
Issue Notification for U.S. Appl. No. 17/179,116 mailed Dec. 25, 2024.
Issue Notification for U.S. Appl. No. 17/326,980 mailed Jul. 10, 2024.
Issue Notification for U.S. Appl. No. 17/447,123 mailed Nov. 13, 2024.
Issue Notification for U.S. Appl. No. 17/448,811 mailed Jul. 3, 2024.
Issue Notification for U.S. Appl. No. 17/450,864 mailed Jan. 8, 2025.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/501,591 mailed Mar. 5, 2025.
Issue Notification for U.S. Appl. No. 17/529,769 mailed Feb. 19, 2025.
Issue Notification for U.S. Appl. No. 17/597,673 mailed Jun. 4, 2025.
Issue Notification for U.S. Appl. No. 17/646,771 mailed Mar. 19, 2025.
Issue Notification for U.S. Appl. No. 17/657,474 mailed Jun. 19, 2024.
Issue Notification for U.S. Appl. No. 17/661,090 mailed Feb. 5, 2025.
Issue Notification for U.S. Appl. No. 17/662,700 mailed Oct. 23, 2024.
Issue Notification for U.S. Appl. No. 17/663,330 mailed Feb. 26, 2025.
Issue Notification for U.S. Appl. No. 17/664,914 mailed Nov. 6, 2024.
Issue Notification for U.S. Appl. No. 17/667,097 mailed Dec. 11, 2024.
Issue Notification for U.S. Appl. No. 17/749,340 mailed May 28, 2025.
Issue Notification for U.S. Appl. No. 18/134,857 mailed May 28, 2025.
Issue Notification for U.S. Appl. No. 18/140,163 mailed Dec. 4, 2024.
Issue Notification for U.S. Appl. No. 18/140,751 mailed Feb. 12, 2025.
Issue Notification for U.S. Appl. No. 18/198,464 mailed Nov. 20, 2024.
Issue Notification for U.S. Appl. No. 18/389,009 mailed Dec. 18, 2024.
Issue Notification for U.S. Appl. No. 18/415,080 mailed Apr. 9, 2025.
Issue Notification for U.S. Appl. No. 18/426,795 mailed Feb. 19, 2025.
Issue Notification for U.S. Appl. No. 18/584,002 mailed Apr. 16, 2025.
Non-Final Office Action for U.S. Appl. No. 16/433,773 mailed Feb. 28, 2025.
Non-Final Office Action for U.S. Appl. No. 16/452,258 mailed Jun. 20, 2024.
Non-Final Office Action for U.S. Appl. No. 16/478,180 mailed Aug. 7, 2024.
Non-Final Office Action for U.S. Appl. No. 17/378,015 mailed Jul. 5, 2024.
Non-Final Office Action for U.S. Appl. No. 17/394,055 mailed Mar. 13, 2025.
Non-Final Office Action for U.S. Appl. No. 17/394,055 mailed Mar. 19, 2025.
Non-Final Office Action for U.S. Appl. No. 17/444,792 mailed Oct. 30, 2024.
Non-Final Office Action for U.S. Appl. No. 17/446,256 mailed Dec. 13, 2024.
Non-Final Office Action for U.S. Appl. No. 17/446,654 mailed Jun. 25, 2024.
Non-Final Office Action for U.S. Appl. No. 17/446,654 mailed May 1, 2025.
Non-Final Office Action for U.S. Appl. No. 17/450,864 mailed May 29, 2024.
Non-Final Office Action for U.S. Appl. No. 17/451,345 mailed Jul. 25, 2024.
Non-Final Office Action for U.S. Appl. No. 17/451,354 mailed Mar. 19, 2025.
Non-Final Office Action for U.S. Appl. No. 17/595,747 mailed Jun. 12, 2025.
Non-Final Office Action for U.S. Appl. No. 17/595,747 mailed Jun. 7, 2024.
Non-Final Office Action for U.S. Appl. No. 17/597,408 mailed Aug. 15, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/631,619 mailed Mar. 19, 2025.
Non-Final Office Action for U.S. Appl. No. 17/645,821 mailed Mar. 31, 2025.
Non-Final Office Action for U.S. Appl. No. 17/645,821 mailed Sep. 6, 2024.
Non-Final Office Action for U.S. Appl. No. 17/653,137 mailed Jan. 28, 2025.
Non-Final Office Action for U.S. Appl. No. 17/653,314 mailed Aug. 29, 2024.
Non-Final Office Action for U.S. Appl. No. 17/653,314 mailed May 8, 2025.
Non-Final Office Action for U.S. Appl. No. 17/653,920 mailed Nov. 27, 2024.
Non-Final Office Action for U.S. Appl. No. 17/655,464 mailed Mar. 20, 2025.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/664,487 mailed May 19, 2025.
Non-Final Office Action for U.S. Appl. No. 17/749,340 mailed Aug. 14, 2024.
Non-Final Office Action for U.S. Appl. No. 17/754,736 mailed Mar. 31, 2025.
Non-Final Office Action for U.S. Appl. No. 17/756,201 mailed Apr. 24, 2025.

(56)     References Cited

OTHER PUBLICATIONS

Non-Final Office Action for U.S. Appl. No. 17/757,311 mailed Oct. 22, 2024.

Non-Final Office Action for U.S. Appl. No. 17/758,152 mailed Apr. 8, 2025.

Non-Final Office Action for U.S. Appl. No. 17/758,316 mailed Aug. 28, 2024.

Non-Final Office Action for U.S. Appl. No. 17/759,697 mailed Dec. 4, 2024.

Non-Final Office Action for U.S. Appl. No. 17/808,354 mailed Dec. 13, 2024.

Non-Final Office Action for U.S. Appl. No. 17/809,083 mailed Apr. 2, 2025.

Non-Final Office Action for U.S. Appl. No. 17/809,083 mailed Mar. 7, 2025.

Non-Final Office Action for U.S. Appl. No. 17/878,268 mailed Mar. 17, 2025.

Non-Final Office Action for U.S. Appl. No. 17/907,125 mailed Dec. 13, 2024.

Non-Final Office Action for U.S. Appl. No. 17/912,147 mailed May 29, 2025.

Non-Final Office Action for U.S. Appl. No. 17/929,887 mailed Jun. 25, 2025.

Non-Final Office Action for U.S. Appl. No. 17/996,064 mailed Mar. 6, 2025.

Non-Final Office Action for U.S. Appl. No. 18/003,029 mailed Apr. 18, 2025.

Non-Final Office Action for U.S. Appl. No. 18/006,807 mailed May 29, 2025.

Non-Final Office Action for U.S. Appl. No. 18/042,842 mailed May 22, 2025.

Non-Final Office Action for U.S. Appl. No. 18/043,618 mailed May 19, 2025.

Non-Final Office Action for U.S. Appl. No. 18/139,523 mailed Aug. 26, 2024.

Non-Final Office Action for U.S. Appl. No. 18/140,751 mailed Jun. 21, 2024.

Non-Final Office Action for U.S. Appl. No. 18/164,800 mailed Apr. 25, 2025.

Non-Final Office Action for U.S. Appl. No. 18/247,986 mailed Jun. 4, 2025.

Non-Final Office Action for U.S. Appl. No. 18/264,004 mailed May 15, 2025.

Non-Final Office Action for U.S. Appl. No. 18/389,009 mailed May 24, 2024.

Non-Final Office Action for U.S. Appl. No. 18/426,795 mailed Aug. 9, 2024.

Non-Final Office Action for U.S. Appl. No. 18/451,080 mailed Jul. 30, 2024.

Non-Final Office Action for U.S. Appl. No. 18/584,002 mailed Sep. 19, 2024.

Notice of Allowance for U.S. Appl. No. 16/369,676 mailed Jun. 17, 2024.

Notice of Allowance for U.S. Appl. No. 16/452,145 mailed Jul. 11, 2024.

Notice of Allowance for U.S. Appl. No. 16/478,180 mailed Dec. 16, 2024.

Notice of Allowance for U.S. Appl. No. 16/904,868 mailed Jan. 21, 2025.

Notice of Allowance for U.S. Appl. No. 16/904,868 mailed Sep. 29, 2024.

Notice of Allowance for U.S. Appl. No. 17/051,585 mailed Dec. 26, 2024.

Notice of Allowance for U.S. Appl. No. 17/179,116 mailed Sep. 13, 2024.

Notice of Allowance for U.S. Appl. No. 17/444,792 mailed Mar. 28, 2025.

Notice of Allowance for U.S. Appl. No. 17/447,123 mailed Jul. 26, 2024.

Notice of Allowance for U.S. Appl. No. 17/448,811 mailed Jun. 14, 2024.

Notice of Allowance for U.S. Appl. No. 17/450,864 mailed Sep. 18, 2024.

Notice of Allowance for U.S. Appl. No. 17/451,345 mailed Jun. 24, 2025.

Notice of Allowance for U.S. Appl. No. 17/501,591 mailed Jul. 31, 2024.

Notice of Allowance for U.S. Appl. No. 17/501,591 mailed Nov. 20, 2024.

Notice of Allowance for U.S. Appl. No. 17/527,769 mailed Nov. 20, 2024.

Notice of Allowance for U.S. Appl. No. 17/596,629 mailed Jan. 29, 2025.

Notice of Allowance for U.S. Appl. No. 17/596,629 mailed May 27, 2025.

Notice of Allowance for U.S. Appl. No. 17/597,673 mailed Feb. 26, 2025.

Notice of Allowance for U.S. Appl. No. 17/646,771 mailed Dec. 17, 2024.

Notice of Allowance for U.S. Appl. No. 17/661,090 mailed Oct. 30, 2024.

Notice of Allowance for U.S. Appl. No. 17/662,700 mailed Jun. 12, 2024.

Notice of Allowance for U.S. Appl. No. 17/663,330 mailed Nov. 20, 2024.

Notice of Allowance for U.S. Appl. No. 17/664,914 mailed Jul. 26, 2024.

Notice of Allowance for U.S. Appl. No. 17/667,097 mailed Aug. 28, 2024.

Notice of Allowance for U.S. Appl. No. 17/749,340 mailed Feb. 14, 2025.

Notice of Allowance for U.S. Appl. No. 17/758,316 mailed Mar. 24, 2025.

Notice of Allowance for U.S. Appl. No. 17/996,155 mailed Jun. 24, 2025.

Notice of Allowance for U.S. Appl. No. 17/996,155 mailed Mar. 11, 2025.

Notice of Allowance for U.S. Appl. No. 17/996,253 mailed Apr. 11, 2025.

Notice of Allowance for U.S. Appl. No. 17/996,468 mailed Apr. 14, 2025.

Notice of Allowance for U.S. Appl. No. 18/007,105 mailed Jun. 17, 2025.

Notice of Allowance for U.S. Appl. No. 18/134,857 mailed Feb. 20, 2025.

Notice of Allowance for U.S. Appl. No. 18/140,163 mailed Aug. 21, 2024.

Notice of Allowance for U.S. Appl. No. 18/140,751 mailed Nov. 1, 2024.

Notice of Allowance for U.S. Appl. No. 18/198,464 mailed Jul. 30, 2024.

Notice of Allowance for U.S. Appl. No. 18/389,009 mailed Aug. 28, 2024.

Notice of Allowance for U.S. Appl. No. 18/415,080 mailed Dec. 30, 2024.

Notice of Allowance for U.S. Appl. No. 18/426,795 mailed Nov. 20, 2024.

Notice of Allowance for U.S. Appl. No. 18/584,002 mailed Jan. 8, 2025.

Restriction Requirement for U.S. Appl. No. 17/527,769 mailed Jun. 17, 2024.

Restriction Requirement for U.S. Appl. No. 17/596,629 mailed Sep. 19, 2024.

Restriction Requirement for U.S. Appl. No. 17/625,941 mailed Aug. 7, 2024.

Restriction Requirement for U.S. Appl. No. 17/754,736 mailed Nov. 20, 2024.

Restriction Requirement for U.S. Appl. No. 17/755,236 mailed Apr. 24, 2025.

Restriction Requirement for U.S. Appl. No. 17/756,201 mailed Oct. 4, 2024.

(56)          References Cited

OTHER PUBLICATIONS

Restriction Requirement for U.S. Appl. No. 17/758,152 mailed Nov. 5, 2024.
Restriction Requirement for U.S. Appl. No. 17/809,083 mailed Dec. 31, 2024.
Restriction Requirement for U.S. Appl. No. 17/878,268 mailed Sep. 20, 2024.
Restriction Requirement for U.S. Appl. No. 17/929,887 mailed Mar. 10, 2025.
Restriction Requirement for U.S. Appl. No. 17/930,238 mailed Apr. 17, 2025.
Restriction Requirement for U.S. Appl. No. 18/041,109 mailed Jun. 4, 2025.
Restriction Requirement for U.S. Appl. No. 18/150,360 mailed May 19, 2025.
Supplemental Notice of Allowance for U.S. Appl. No. 17/597,673 mailed Apr. 10, 2025.
U.S. Appl. No. 17/013,822, filed Sep. 7, 2020.
U.S. Appl. No. 17/596,629, filed Dec. 15, 2021.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.

U.S. Appl. No. 18/982,930, filed Dec. 16, 2024.
U.S. Appl. No. 19/038,774, filed Jan. 28, 2025.
U.S. Appl. No. 19/039,165, filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.
U.S. Appl. No. 19/049,501, filed Feb. 10, 2025.
U.S. Appl. No. 19/049,783, filed Feb. 10, 2025.
U.S. Appl. No. 19/058,726, filed Feb. 20, 2025.
U.S. Appl. No. 19/069,480, filed Mar. 4, 2025.
U.S. Appl. No. 19/078,602, filed Mar. 13, 2025.
U.S. Appl. No. 19/092,262, filed Mar. 27, 2025.
U.S. Appl. No. 19/103,165, filed Feb. 11, 2025.
U.S. Appl. No. 19/110,938, filed Mar. 12, 2025.
U.S. Appl. No. 19/111,921, filed Mar. 14, 2025.
U.S. Appl. No. 19/127,234, filed May 5, 2025.
U.S. Appl. No. 19/171,983, filed Apr. 7, 2025.
U.S. Appl. No. 19/179,540, filed Apr. 15, 2025.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 19/240,380, filed Jun. 17, 2025.
U.S. Appl. No. 63/181,709, filed Apr. 29, 2021.
U.S. Appl. No. 63/564,696, filed Mar. 13, 2024.
U.S. Appl. No. 63/568,615, filed Mar. 22, 2024.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
"Dictionary.com, Abut Definition and Meaning", Dictionary.com, https://www.dictionary.com/browse/abut, 2024, 1 page.
"Oblong", Cambridge Dictionary, https://dictionary.cambridge.org/dictionary/english/oblong, 2024, 1 page.
"Surface Energy Data for Cellulose acetate, CAS # 9004-35-7", Diviersified Enterprises, 2009, 1 page.
Foamtech, "Foam Packaging Isnert: Best Selection Guide", https://web/archive.org/web/20170922162235/http://www.foamtechchina/com:80/foam-packaging-insert/, Sep. 22, 2017, 25 pages.

\* cited by examiner

FLUID COLLECTION DEVICES, SYSTEMS, AND METHODS

CROSS-REFERENCE TO RELATED APPLICATIONS

This application is a National Stage of International Application No. PCT/US2019/029616 filed on Apr. 29, 2019, which claims priority from U.S. Provisional Application No. 62/665,711 filed on May 2, 2018, the disclosure of which is incorporated herein, in its entirety, by this reference.

BACKGROUND

An individual may have limited or impaired mobility such that typical urination processes are challenging or impossible. For example, the individual may have surgery or a disability that impairs mobility. In another example, the individual may have restricted travel conditions such as those experienced by pilots, drivers, and workers in hazardous areas. Additionally, fluid collection from the individual may be needed for monitoring purposes or clinical testing.

Bed pans and urinary catheters, such as a Foley catheter, can be used to address some of these circumstances. However, bed pans and urinary catheters have several problems associated therewith. For example, bed pans can be prone to discomfort, pressure ulcers spills, and other hygiene issues. Urinary catheters be can be uncomfortable, painful, and can cause urinary tract infections.

Thus, users and manufacturers of fluid collection devices continue to seek new and improved devices, systems, and methods to collect urine.

SUMMARY

Embodiments disclosed herein are fluid collection devices and methods of assembling fluid collection devices. In an embodiment, a fluid collection device includes a fluid impermeable barrier, a fluid permeable body, and a reservoir. The fluid impermeable barrier at least partially defines a chamber. The fluid impermeable barrier includes an opening extending therethrough. The opening is configured to be positioned adjacent to or receive therein a urethra of a subject. The fluid permeable body is a singular porous material in a substantially cylindrical shape and positioned at least partially within the chamber. The reservoir is at least partially defined by the fluid permeable body. The fluid permeable body is configured to wick fluid away from the opening to the reservoir.

In an embodiment, a method of assembling a fluid collection device is disclosed. The method includes providing a fluid impermeable barrier. The fluid impermeable barrier at least partially defines a chamber and has an opening extending therethrough. The opening is configured to be positioned adjacent to or receive therein a urethra of a subject. The method also includes inserting a substantially cylindrical and fluid permeable body into the chamber of the fluid impermeable barrier thereby forming a fluid collection device. The fluid permeable body at least partially defines a reservoir when the fluid permeable body is inserted into the chamber. The fluid permeable body includes a singular porous material that is substantially cylindrical in shape and configured to wick fluid away from the opening to the reservoir.

In an embodiment, a fluid collection device includes a fluid impermeable barrier, an opening, a fluid permeable layer, a reservoir, and a conduit. The fluid impermeable barrier at least partially defines a chamber. The opening extends into the chamber and is configured to be positioned adjacent to or receive therein a urethra of a subject. The fluid permeable layer is positioned within the chamber and includes a singular porous material configured to wick any fluid away from the opening. The reservoir is formed within the chamber and partially defined by a portion of the fluid permeable layer and an impermeable border. At least a portion of the singular porous material of the fluid permeable layer extends continuously between the opening and the reservoir to wick any fluid from the opening to the reservoir. The conduit includes an inlet and an outlet. The inlet extends to the reservoir and provides fluid communication between the reservoir and the outlet.

In an embodiment, a method to collect fluid includes positioning a fluid permeable body of a fluid collection device adjacent to a urethra of a subject. The fluid permeable body is disposed within a chamber of a fluid impermeable barrier of the fluid collection device and exposed to the urethra of the subject through an opening in the fluid collection device. The method also includes securing the fluid collection device to the user. The method also includes receiving fluids from the female urethra into the chamber of the fluid collection device.

In an embodiment, a fluid collection device includes a body having an opening and a closed distal end. The body includes a fluid impermeable side wall at least partially defining a chamber within the body. The body also includes a fluid permeable layer positioned with the chamber to partially define a reservoir at the distal end, the fluid permeable layer including a singular porous material. The body is configured to be disposed with a urethra of a subject disposed within the opening or adjacent to the opening. The body also is configured to receive urine discharged from the urethra in the opening, the fluid permeable layer is configured to wick urine discharged from the urethra away from the subject to the reservoir to have the urine withdrawn from the reservoir via a conduit.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1A:
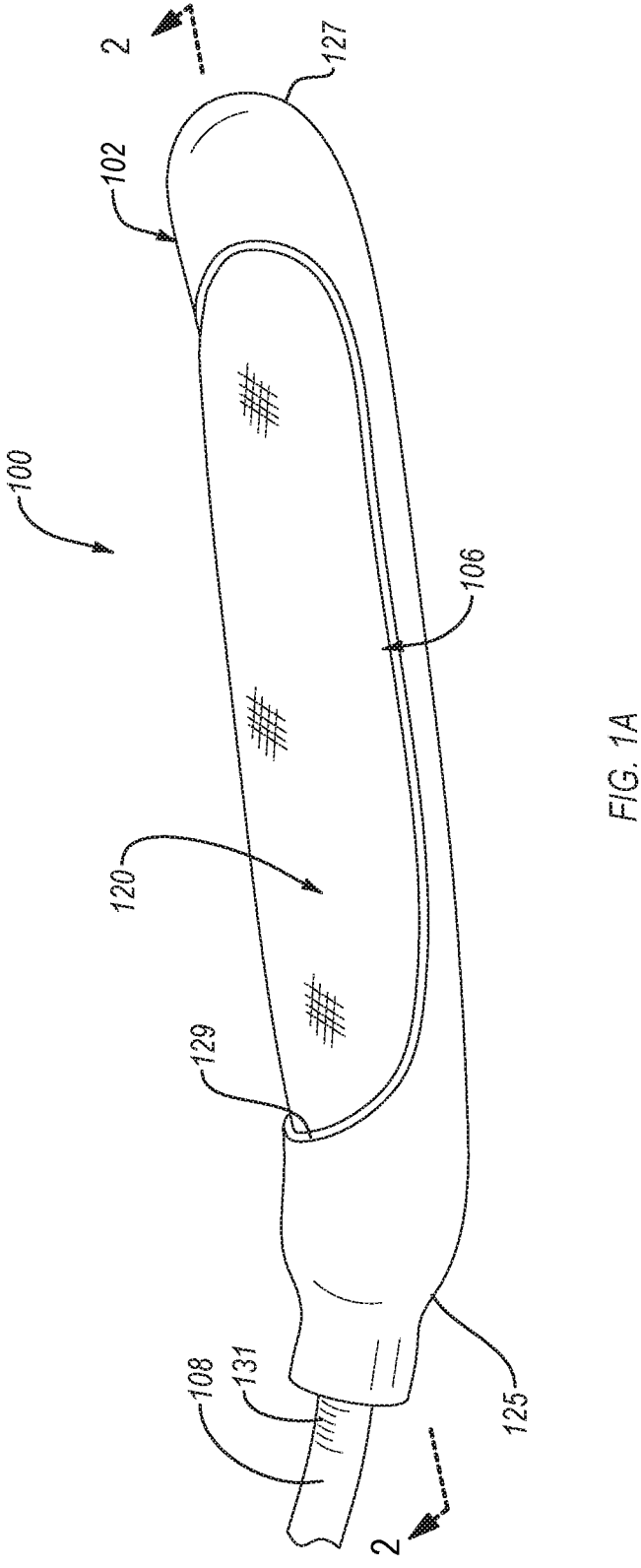
FIG. 1A is an isometric view of a female fluid collection device, according to an embodiment.

Embodiments disclosed herein are fluid collection devices and methods of assembling fluid collection devices. In an embodiment, a fluid collection device includes a fluid impermeable barrier, a fluid permeable body, and a reservoir. The fluid impermeable barrier at least partially defines a chamber. The fluid impermeable barrier includes an opening extending therethrough. The opening is configured to be positioned adjacent to or receive therein a urethra of a subject. The fluid permeable body is a singular porous material in a substantially cylindrical shape and positioned at least partially within the chamber. The reservoir is at least partially defined by the fluid permeable body. The fluid permeable body is configured to wick fluid away from the opening to the reservoir.

As noted above, in many embodiments disclosed herein, the fluid permeable body includes a singular and porous body. That is, during use, the fluid permeable body extends from a conduit or elongated opening to interface the fluid impermeable barrier and the opening. A singular fluid permeable body can reduce the number of components in the fluid collection device, reduces the assembly time of the fluid collection device, requires shelf-life data for only a single component, and/or provides a latex-free single component.

The fluid collection devices disclosed herein are configured to collect fluids from an individual. The fluids collected by the fluid collection devices can include urine. The fluids collected by the fluid collection devices can also include at least one of vaginal discharge, penile discharge, reproductive fluids, blood, sweat, or other bodily fluids.

Fluid collection devices described herein may be used in fluid collection systems. The fluid collection systems can include a fluid collection device, a fluid storage container, and a portable vacuum source. Fluid (e.g., urine or other bodily fluids) collected in the fluid collection device may be removed from the fluid collection device via a conduit which protrudes into an interior region of the fluid collection device. For example, a first open end of the conduit may extend into the fluid collection device to a reservoir therein. The second open end of the conduit may extend into the fluid collection device or the portable vacuum source. The suction force may be introduced into the interior region of the fluid collection device via the first open end of the conduit responsive to a suction (e.g., vacuum) force applied at the second end of the conduit. The suction force may be applied to the second open end of the conduit by the portable vacuum source either directly or indirectly.

Fluid collection devices describe herein may be shaped and sized to be positioned adjacent to a female urethra or have a male urethra positioned therethrough (e.g., receive a penis therein). For example, the fluid collection device may include a fluid impermeable barrier at least partially defining a chamber (e.g., interior region of the fluid collection device) of the fluid collection device. The fluid impermeable barrier also defines an opening extending therethrough from the external environment. The opening may be positioned adjacent to a female urethra or have a male urethra positioned therethrough. The fluid collection device may include a fluid permeable body disposed within the fluid impermeable barrier. The conduit may extend into the fluid collection device at a first end region, through one or more of the fluid impermeable barrier, fluid permeable body to a second end region of the fluid collection device. Exemplary fluid collection devices for use with the systems and methods herein are described in more detail below.

In some embodiments, the portable vacuum source may be disposed in or on the fluid collection device. In such embodiments, the conduit may extend from the fluid collection device and attach to the portable vacuum source at a first point therein. An additional conduit may attach to the portable vacuum source at a second point thereon and may extend out of the fluid collection device, and may attach to the fluid storage container. Accordingly, a vacuum (e.g., suction) may be drawn through fluid collection device via the fluid storage container. Fluid, such as urine, may be drained from the fluid collection device using the portable vacuum source.

FIG. 1A is a perspective view of a fluid collection device 100, according to an embodiment. The fluid collection device 100 is an example of a female fluid collection device 100 that is configured to receive fluids from a female. The fluid collection device 100 includes a fluid impermeable barrier 102 having a first end region 125 and a second end region 127. The fluid impermeable barrier 102 at least partially defines a chamber 104 (e.g., interior region, shown in FIG. 1C) and includes an inward border or edge 129 defining an opening 106. The fluid impermeable barrier 102 is substantially cylindrical in shape between the first end region 125 and the second end region 127. The opening 106 is formed in and extends through the fluid impermeable barrier 102, thereby enabling fluids to enter the chamber 104 from outside of the fluid collection device 100. The opening 106 can be configured to be positioned adjacent to a female urethra.

The fluid collection device 100 may be positioned proximate to the female urethra and urine may enter the interior region of the fluid collection device 100 via the opening 106. The fluid collection device 100 is configured to receive the fluids into the chamber 104 via the opening 106. For example, the opening 106 can exhibit an elongated shape that is configured to extend from a first location below the urethral opening (e.g., at or near the anus or the vaginal opening) to a second location above the urethral opening (e.g., at or near the clitoris or the pubic hair). The opening 106 can exhibit an elongated shape since the space between the legs of a female is relatively small when the legs of the female are closed, thereby only permitting the flow of the fluids along a path that corresponds to the elongated shape of the opening 106. The opening 106 in the fluid impermeable barrier 102 can exhibit a width that is measured transverse to the longitudinal direction and may be at least about 10% of the circumference of the fluid collection device 100, such as about 25% to about 50%, about 40% to about 60%, about 50% to about 75%, about 65% to about 85%, or about 75% to about 100% of the circumference of the fluid collection device 100. The opening 106 can exhibit a width that is greater than 50% of the circumference of the fluid collection device 100 since the vacuum (e.g., suction) through the conduit 108 pulls the fluid into the conduit 108. In some embodiments, the opening 106 may be vertically oriented (e.g., having a major axis parallel to the longitudinal axis of the device 100). In some embodiments, (not shown), the opening 106 may be horizontally oriented (e.g., having a major axis perpendicular to the longitudinal axis of the device 100). In some embodiments, the inward border or edge 129 of the fluid impermeable barrier 102 defines the opening 106. The edge 129 can include two opposing arced portions, the arcs following the outer circumference or periphery of the substantially cylindrical fluid impermeable barrier 102. In an embodiment, the fluid impermeable barrier 102 can be configured to be attached to the individual, such as adhesively attached (e.g., with a hydrogel adhesive) to the individual. According to an embodiment, a suitable adhesive is a hydrogel layer, such as those disclosed in U.S. Patent Application Publication No. 2017/0189225, the disclosure of which is incorporated herein by reference in its entirety.

The fluid impermeable barrier 102 may also temporarily store the fluids in the chamber 104. For example, the fluid impermeable barrier 102 can be formed of any suitable fluid impermeable materials, such as a fluid impermeable polymer (e.g., silicone, polypropylene, polyethylene, polyethylene terephthalate, a polycarbonate, etc.), a metal film, another suitable material, or combinations thereof. As such, the fluid impermeable barrier 102 substantially prevents the fluids from exiting the portions of the chamber 104 that are spaced from the opening 106. The fluid impermeable barrier 102 is flexible, allowing the fluid collection device 100 to bend or curve when positioned against the body of a wearer.

The fluid collection device 100 can include a fluid permeable body 120 or layer disposed in the chamber 104. The fluid permeable body 120 can cover at least a portion (e.g., all) of the opening 106. The fluid permeable body 120 can be configured to wick any fluid away from the opening 106, thereby preventing the fluid from escaping the chamber 104. The fluid permeable body 120 also can wick the fluid generally towards an interior of the chamber 104, as discussed in more detail below. A portion of the fluid permeable body 120 can define a portion of an outer surface of the fluid collection device 100. Specifically, the portion of the fluid permeable body 120 defining the portion of the outer surface of the fluid collection device 100 can be the portion of the fluid permeable body 120 exposed by the opening 106 defined by the fluid impermeable barrier 102 that contacts the user. Moreover, the portion of the fluid permeable device defining the portion of the outer surface of the fluid collection device 100 may free from coverage by gauze or other wicking material at the opening.

Figure 2A:
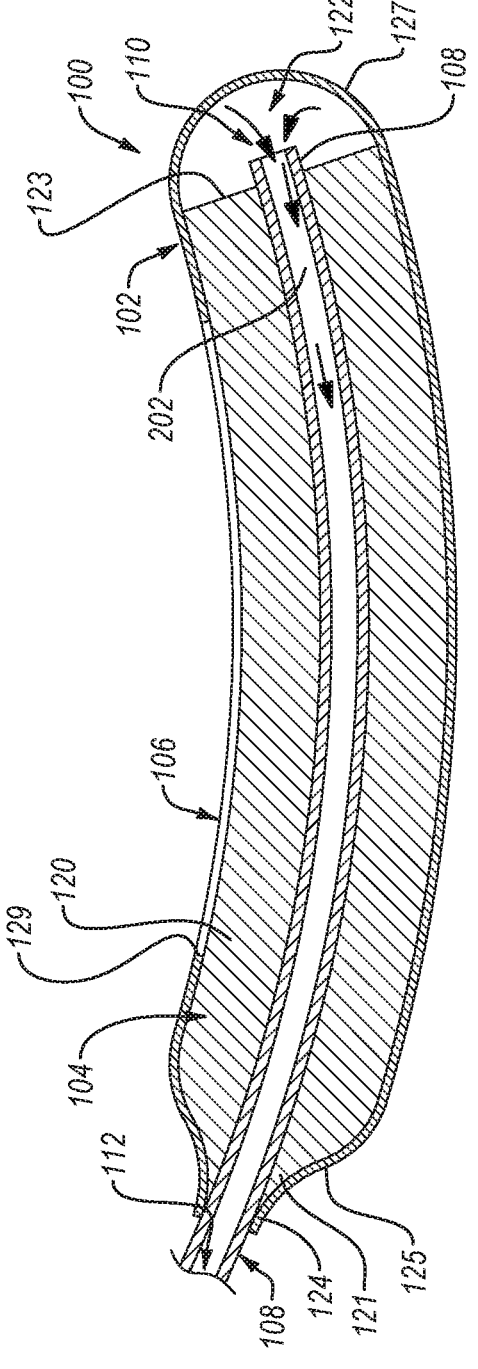
FIGS. 2A and 2B are cross-sectional views of the female fluid collection device of FIG. 1 taken along line 2-2 thereof, according to embodiments.
Figure 2B:
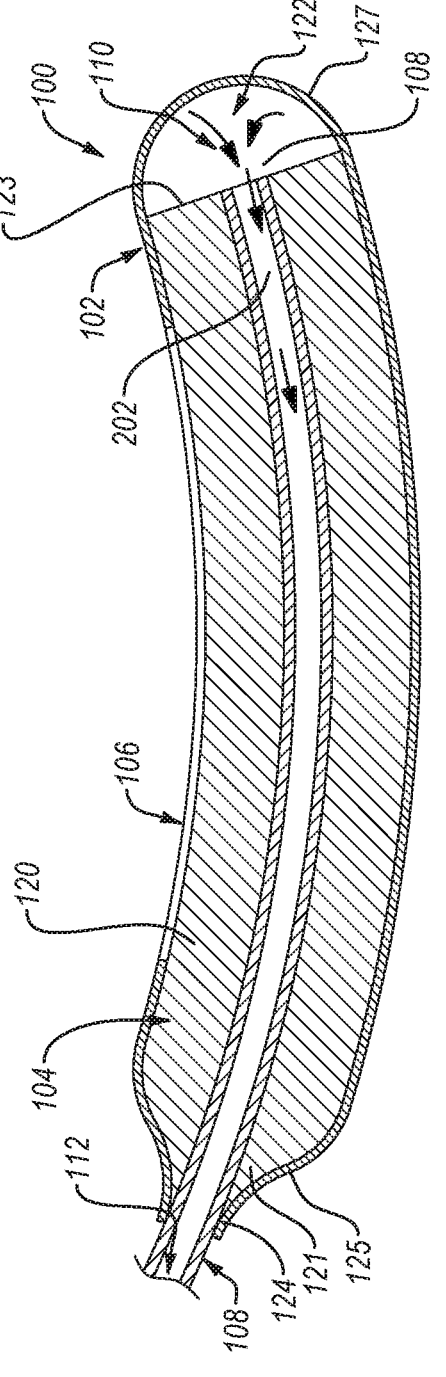
Figure 3:
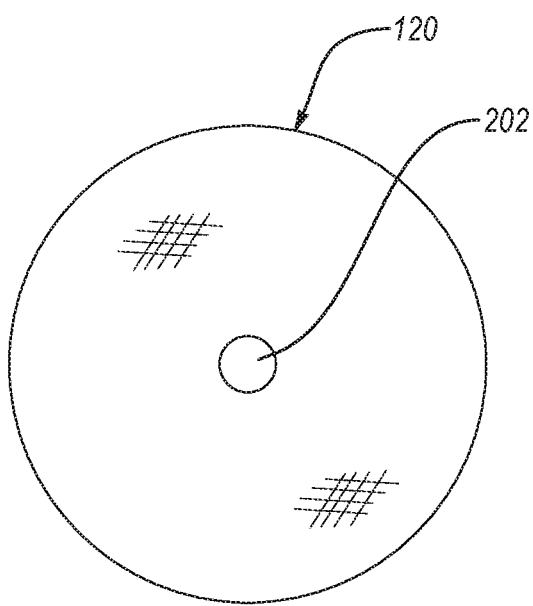
FIG. 3 is a top view of a fluid permeable body, according to an embodiment.

The fluid permeable body 120 can include any material that can wick the fluid. The permeable properties referred to herein can be wicking, capillary action, diffusion, or other similar properties or processes, and are referred to herein as "permeable" and/or "wicking." Such "wicking" may exclude absorption into the wicking material. The fluid permeable body 120 can include a one-way fluid movement fabric. As such, the fluid permeable body 120 can remove fluid from the area around the female urethra, thereby leaving the urethra dry. The fluid permeable body 120 can enable the fluid to flow generally towards a reservoir 122 (shown in FIGS. 2A and 2B) of void space formed within the chamber 104. For example, the fluid permeable body 120 can include a porous or fibrous material, such as hydrophilic polyolefin. In some embodiments, the fluid permeable body 120 consists of or consists essentially of a porous or fibrous material, such as hydrophilic polyolefin. Examples of polyolefin that can be used in the fluid permeable body 120 include, but are not limited to, polyethylene, polypropylene, polyisobutylene, ethylene propylene rubber, ethylene propylene diene monomer, or combinations thereof. The porous or fibrous material can be extruded into a substantially cylindrically shape to fit within the chamber 104 of the fluid impermeable barrier 102. The fluid permeable body 120 can include varying densities or dimensions. Moreover, the fluid permeable body 120 can be manufactured according to various manufacturing methods, such as molding, extrusion, or sintering.

In some embodiments, the fluid permeable body 120 includes a singular and porous body. That is, during use, the fluid permeable body 120 extends from the conduit 108 to interface the fluid impermeable barrier 102 and the opening 106. In some embodiments, a majority of the outer surface 109 (shown in FIG. 1C) of the fluid permeable body 120 interfaces with an inner surface 103 (shown in FIG. 1C) of the fluid impermeable barrier 106. A singular fluid permeable body 120 is advantageous to conventional systems, which typically require an air-laid nonwoven pad covered by a ribbed fabric compression bandage, because a singular fluid permeable body 120 reduced the number of components in the fluid collection device 100, reduces the assembly time of the fluid collection device 100, requires shelf-life data for only a single component, and provides a latex-free single component. In some embodiments, at least a portion of the singular porous material of the fluid permeable body 120 extends continuously between the opening 106 and the reservoir 122 to wick any fluid from the opening 106 directly to the reservoir 122. Moreover, as the fluid impermeable barrier is flexible and the fluid permeable body 120 is configured to wick fluid from the body rather than absorb fluid from the body and hold the fluid against the body, the fluid collection device 100, in some embodiments, is free from a seal or cushioning ring on the inward edge 129 defining the opening 106.

Figure 1B:
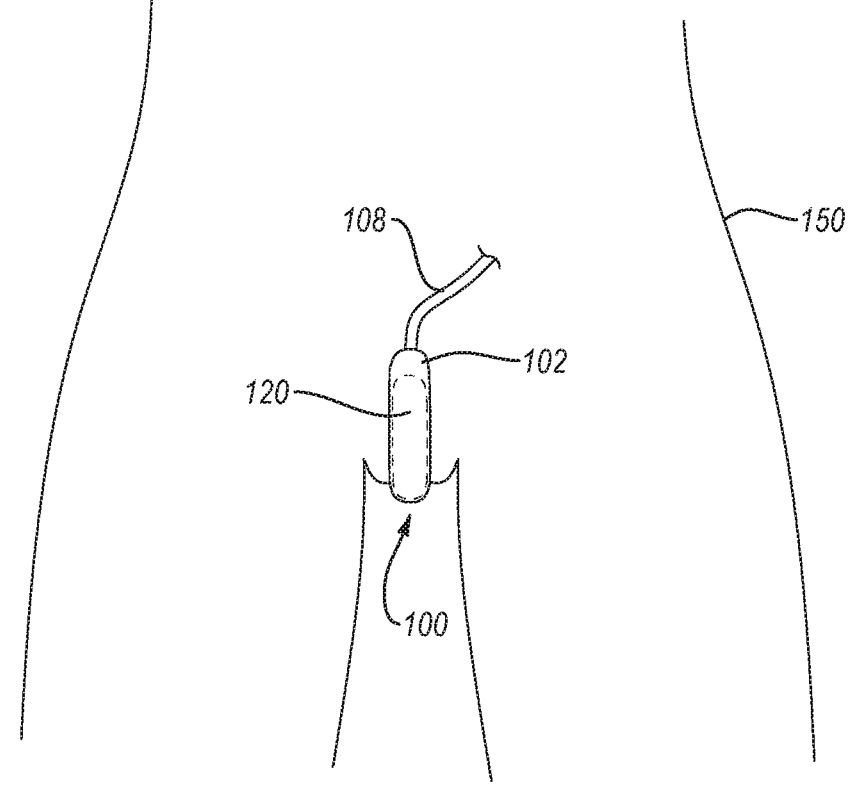
FIG. 1B is a front view of a female fluid collection device worn on a female user, according to an embodiment.
Figure 1C:
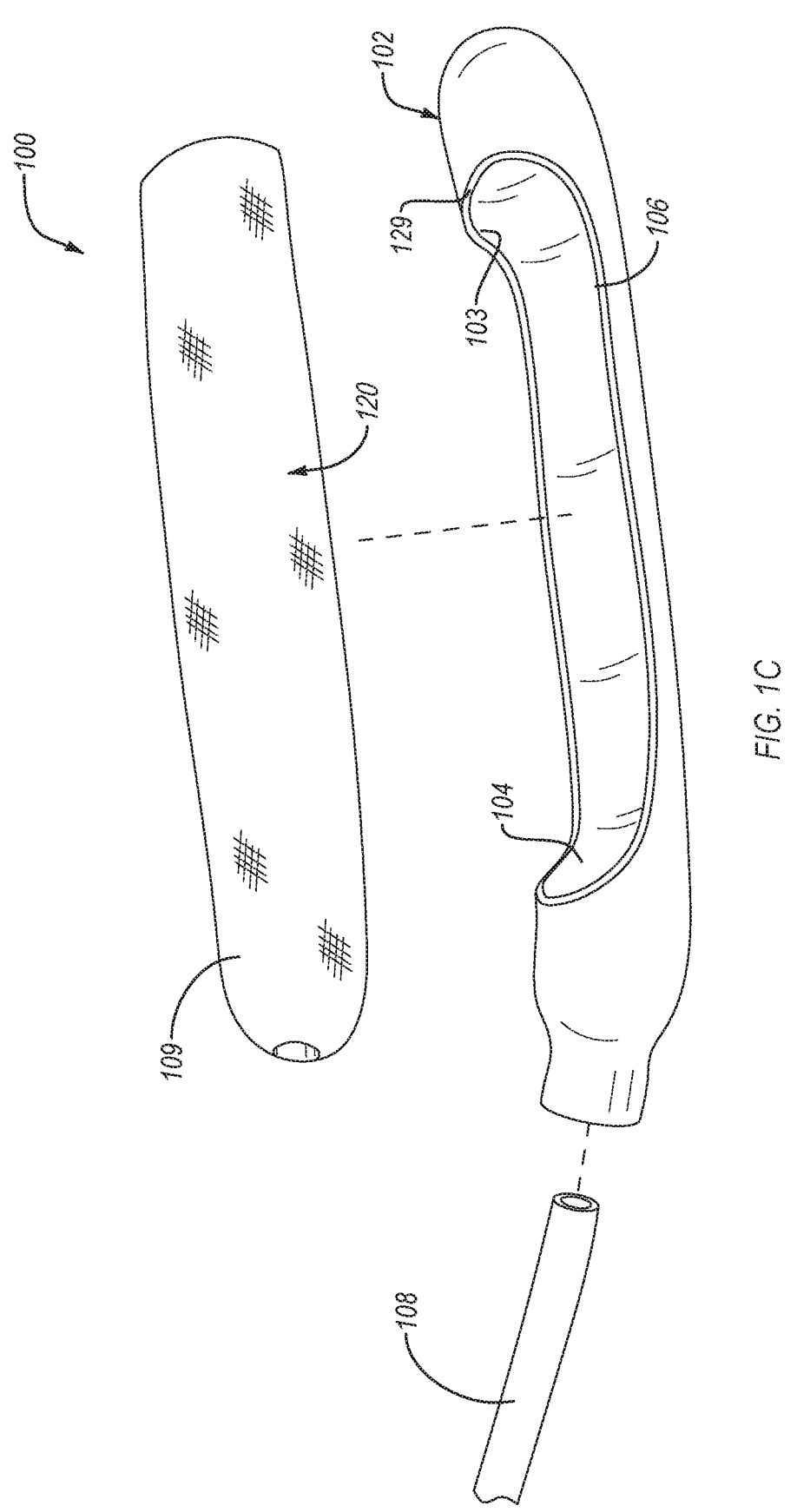
FIG. 1C is an exploded view of the female fluid collection device of FIG. 1A, according to an embodiment.

FIG. 1B is a front view of a fluid collection device 100 in use on a female user 150. In use, the fluid permeable body 120 of the fluid collection device is positioned adjacent to a urethra of the user 150. The fluid permeable body 120 is disposed within a chamber 104 (shown in FIGS. 2A and 2B) of the fluid impermeable barrier 102 of the fluid collection device 100 and is exposed to the urethra of the user 150 through the opening 106 in the fluid collection device 100. The fluid collection device 100 can be secured to the user with any of a number of securing devices. Fluids received in the chamber 104 of the fluid collection device 100 from the urethra can be removed through the conduit 108.

FIG. 2 is a cross-sectional view of the fluid collection device 100 taken along line 2-2 of FIG. 1. The fluid collection device 100 also includes conduit 108 that is at least partially disposed in the chamber 104. The conduit 108 (e.g., a tube) includes an inlet 110 at a second end region 127 of the fluid impermeable barrier 102 and an outlet 112 at a first end region 125 of the fluid impermeable barrier 102 positioned downstream from the inlet 110. The conduit 108 provides fluid communication between an interior region of the chamber 104 and a fluid storage container (not shown) or a portable vacuum source (not shown). For example, the conduit 108 may directly or indirectly fluidly couple the interior region of the chamber 104 and/or the reservoir 122 with the fluid storage container or the portable vacuum source.

In the illustrated embodiment, the fluid permeable body 120 defines a bore 202 extending through the fluid permeable body 120 from a first body end 121 of the fluid permeable body 120 to a second body end 123 of the fluid permeable body 120 distal to the first body end 120. In other embodiments, the bore 202 extends only partially into the fluid permeable body from the first body end 121 of the fluid permeable body 120.

In the illustrated embodiment, the conduit 108 is at least partially disposed in the chamber 104 and interfaces at least a portion of the bore 202 of the fluid permeable body 120.

For example, the conduit 108 may extend into the fluid impermeable barrier 102 from the first end region 125 (e.g., proximate to the outlet 112) and may extend through the bore 202 to the second end region 127 (e.g., opposite the first end region 125) to a point proximate to a reservoir 122 such that the inlet 110 is in fluid communication with the reservoir 122. For example, in the illustrated embodiment, the inlet 110 is positioned in the reservoir 122. However, in other embodiments, the inlet 110 may be positioned flush with or behind an end of the fluid permeable body 120 that partially defines the reservoir 122. The fluid collected in the fluid collection device 100 may be removed from the interior region of the chamber 104 via the conduit 108. The conduit 108 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In some embodiments, the conduit 108 may include silicone or latex.

The fluid impermeable barrier 102 can store fluids in a reservoir 122 therein. The reservoir 122 is an unoccupied portion of the chamber 104 and is void of other material. In some embodiments, the reservoir 122 is defined at least partially by the fluid permeable body 120 and the fluid impermeable barrier 102. The reservoir 122 may be disposed in any portion of the interior region of the chamber 104. For example, the fluid reservoir 122 may be positioned in the second end region 127 of the chamber 104. In the illustrated embodiment, the reservoir 122 is defined by the second body end 123 of the fluid permeable body 120 and the second end region 127 of the fluid impermeable barrier 122.

In an embodiment, the fluid impermeable barrier 102 can be air permeable and fluid impermeable. In such an embodiment, the fluid impermeable barrier 102 can be formed of a hydrophobic material that defines a plurality of pores. In an embodiment, one or more portions of at least the outer surface of the fluid impermeable barrier 102 can be formed from a soft and/or smooth material, thereby reducing chaffing. The fluid impermeable barrier 102 may include markings thereon, such as one or more markings to aid a user in aligning the device 100 on the wearer. For example, a line on the fluid impermeable barrier 102 (e.g., opposite the opening 106) may allow a healthcare professional to align the opening 106 over the urethra of the wearer. In examples, the markings may include one or more of alignment guide or an orientation indicator, such as a stripe or hashes. Such markings may be positioned to align the device 100 to one or more anatomical features such as a pubic bone, etc.

In an embodiment, the fluid permeable body 120 and at least a portion of the conduit 108 can at least substantially completely fill the chamber 104. In another example, the fluid permeable body 120 and at least a portion of the conduit may not substantially completely fill the chamber 104. In such an example, the fluid collection device 100 includes the reservoir 122 disposed in the chamber 104. The reservoir 122 is a substantially unoccupied portion of the chamber 104. The fluids that are in the chamber 104 can flow through the fluid permeable body 120 to the reservoir 122. The reservoir 122 can store at least some of the fluids therein. In these and other embodiments, the fluid permeable body 120, at least a portion of the conduit 108, and the reservoir 122 can at least substantially completely fill the chamber 104.

In an embodiment, the reservoir 122 can be located at the portion of the chamber 104 that is closest to the inlet 110 (e.g., the second end region). However, the reservoir 122 can be located at different locations in the chamber 104. For example, the reservoir 122 can be located at the end of the chamber 104 that is closest to the outlet 112. In these and other embodiments, the conduit 108 may extend through the fluid impermeable barrier to the reservoir 122 without extending through the fluid permeable body 120. Accordingly, in these and other embodiments, the fluid permeable body 120 may be free from the bore. In another embodiment, the fluid collection device 100 can include multiple reservoirs, such as a first reservoir that is located at the portion of the chamber of the chamber 104 that is closest to the inlet 110 (e.g., second end region) and a second reservoir that is located at the portion of the of the chamber 104 that is closest to the outlet 112 (e.g., first end region). In another example, the fluid permeable body 120 is spaced from at least a portion of the conduit 108 and the reservoir 122 can be the space between the fluid permeable body 120 and the conduit 108.

Other embodiments of fluid impermeable barriers, fluid permeable membranes, fluid permeable bodies, chambers, and their shapes and configurations are disclosed in U.S. patent application Ser. No. 15/612,325 filed on Jun. 2, 2017; U.S. patent application Ser. No. 15/260,103 filed on Sep. 8, 2016; and U.S. patent application Ser. No. 15/611,587 filed on Jun. 1, 2017, the disclosure of each of which is incorporated herein, in its entirety, by this reference.

The fluid impermeable barrier 102, the fluid permeable body 120 can be configured to have the conduit 108 at least partially disposed in the chamber 104. For example, the fluid permeable body 120 can be configured to form a space that accommodates the conduit 108, such as the bore 202. In another example, the fluid impermeable barrier 102 can define an aperture 124 sized to receive the conduit 108 (e.g., at least one tube). The at least one conduit 108 can be disposed in the chamber 104 via the aperture 124. The apertures 124 can be configured to form an at least substantially fluid tight seal against the conduit 108 or the at least one tube thereby substantially preventing the fluids from escaping the chamber 104.

When secured to the fluid collection device 100, the conduit 108 is configured to provide fluid communication with and at least partially extend between one or more of a fluid storage containers (not shown) and a portable vacuum source (not shown). For example, the conduit 108 may be configured to be fluidly coupled to and at least partially extend between one or more of the fluid storage containers and the portable vacuum source. In an embodiment, the conduit 108 is configured to be directly connected to the portable vacuum source (not shown). In such an example, the conduit 108 can extend from the fluid impermeable barrier 102 by at least one foot, at least two feet, at least three feet, or at least six feet. In another example, the conduit 108 is configured to be indirectly connected to at least one of the fluid storage container (not shown) or the portable vacuum source (not shown). In some examples, the conduit may be frosted or opaque (e.g., black) to obscure visibility of the fluids therein. In some embodiments, the conduit is secured to a wearer's skin with a catheter securement device, such as a STATLOCK® catheter securement device available from C. R. Bard, Inc., including but not limited to those disclosed in U.S. U.S. Pat. Nos. 6,117,163; 6,123,398; and 8,211,063, the disclosures of which are all incorporated herein by reference in their entirety.

The inlet 110 and the outlet 112 are configured to provide fluid communication (e.g., directly or indirectly) between the portable vacuum source (not shown) and the chamber 104 (e.g., the reservoir 122). For example, the inlet 110 and the outlet 112 of the conduit 108 may be configured to directly or indirectly fluidly couple the portable vacuum source to the reservoir 122. In an embodiment, the inlet 110 and/or the outlet 112 can form a male connector. In another example, the inlet 110 and/or the outlet 112 can form a female connector. In an embodiment, the inlet 110 and/or the outlet 112 can include ribs that are configured to facilitate secure couplings. In an embodiment, the inlet 110 and/or the outlet 112 can form a tapered shape. In an embodiment, the inlet 110 and/or the outlet 112 can include a rigid or flexible material.

Locating the inlet 110 at or near a gravimetrically low point of the chamber 104 enables the conduit to receive more of the fluids than if inlet 110 was located elsewhere and reduce the likelihood of pooling (e.g., pooling of the fluids can cause microbe growth and foul odors). For instance, the fluids in the fluid permeable body 120 can flow in any direction due to capillary forces. However, the fluids may exhibit a preference to flow in the direction of gravity, especially when at least a portion of the fluid permeable body 120 is saturated with the fluids.

As the portable vacuum source applies a vacuum/suction in the conduit 108, the fluid(s) in the chamber 104 (e.g., such as in the reservoir 122 positioned at the first end region 125, the second end region 127, or other intermediary positions within the chamber 104) may be drawn into the inlet 110 and out of the fluid collection device 100 via the conduit 108.

In an embodiment, the conduit 108 is configured to be at least insertable into the chamber 104. In such an embodiment, the conduit 108 can include one or more markers 131 (shown in FIG. 1) on an exterior thereof that are configured to facilitate insertion of the conduit 108 into the chamber 104. For example, the conduit 108 can include one or more markings thereon that are configured to prevent over or under insertion of the conduit 108, such as when the conduit 108 defines an inlet 110 that is configured to be disposed in or adjacent to the reservoir 122. In another embodiment, the conduit 108 can include one or more markings thereon that are configured to facilitate correct rotation of the conduit 108 relative to the chamber 104. In an embodiment, the one or more markings can include a line, a dot, a sticker, or any other suitable marking. In examples, the conduit 108 may extend into the fluid impermeable barrier 102 from the first end region (e.g., proximate to the outlet 112) and may extend to the second end region (e.g., opposite the first end region) to a point proximate to the reservoir 122 such that the inlet 110 is in fluid communication with the reservoir 122. In some embodiments (not shown), the conduit 108 may enter the second end region and the inlet 110 may be disposed in the second end region (e.g., in the reservoir 122). The fluid collected in the fluid collection device 100 may be removed from the interior region of the chamber 104 via the conduit 108. The conduit 108 may include a flexible material such as plastic tubing (e.g., medical tubing) as disclosed herein. In some examples, the conduit 108 may include one or more portions that are resilient, such as to by having one or more of a diameter or wall thickness that allows the conduit to be flexible.

In an embodiment, one or more components of the fluid collection device 100 can include an antimicrobial material, such as an antibacterial material where the fluid collection device may contact the wearer or the bodily fluid of the wearer. The antimicrobial material can include an antimicrobial coating, such as a nitrofurazone or silver coating. The antimicrobial material can inhibit microbial growth, such as microbial growth due to pooling or stagnation of the fluids. In an embodiment, one or more components of the fluid collection device 100 (e.g., impermeable barrier 102, conduit 108, etc.) can include an odor blocking or absorbing material such as a cyclodextrine containing material or a thermoplastic elastomer (TPE) polymer.

In any of the embodiments disclosed herein the conduits 108 may include or be operably coupled to a flow meter (not shown) to measure the flow of fluids therein, one or more securement devices (e.g., a StatLock securement device, not shown) or fittings to secure the conduit 108 to one or more components of the systems or devices disclosed herein (e.g., portable vacuum source or fluid storage container), or one or more valves to control the flow of fluids in the systems and devices herein.

In an embodiment, at least one of portion of the conduit 108 of the fluid collection devices or systems herein can be formed of an at least partially opaque material which can obscure the fluids that are present therein. For example, the B section of the conduits 108 disclosed herein may be formed of an opaque material or translucent material while the A section may be formed of a transparent material or translucent material. In some embodiments, the B section may include transparent or translucent material. Unlike the opaque or nearly opaque material, the translucent material allows a user of the devices and systems herein to visually identify fluids or issues that are inhibiting the flow of fluids within the conduit 108.

In any of the examples, systems or devices disclosed herein, the system of fluid collection device may include moisture sensors (not shown) disposed inside of the chamber of the fluid collection device. In such examples, the moisture sensor may be operably coupled to a controller or directly to the portable vacuum source, and may provide electrical signals indicating that moisture is or is not detected in one or more portions of the chamber. The moisture sensor(s) may provide an indication that moisture is present, and responsive thereto, the controller or portable vacuum device may direct the initiation of suction to the chamber to remove the fluid therefrom. Suitable moisture sensors may include capacitance sensors, volumetric sensors, potential sensors, resistance sensors, frequency domain reflectometry sensors, time domain reflectometry sensors, or any other suitable moisture sensor. In practice, the moisture sensors may detect moisture in the chamber and may provide a signal to the controller or portable vacuum source to activate the portable suction device.

Figure 4:
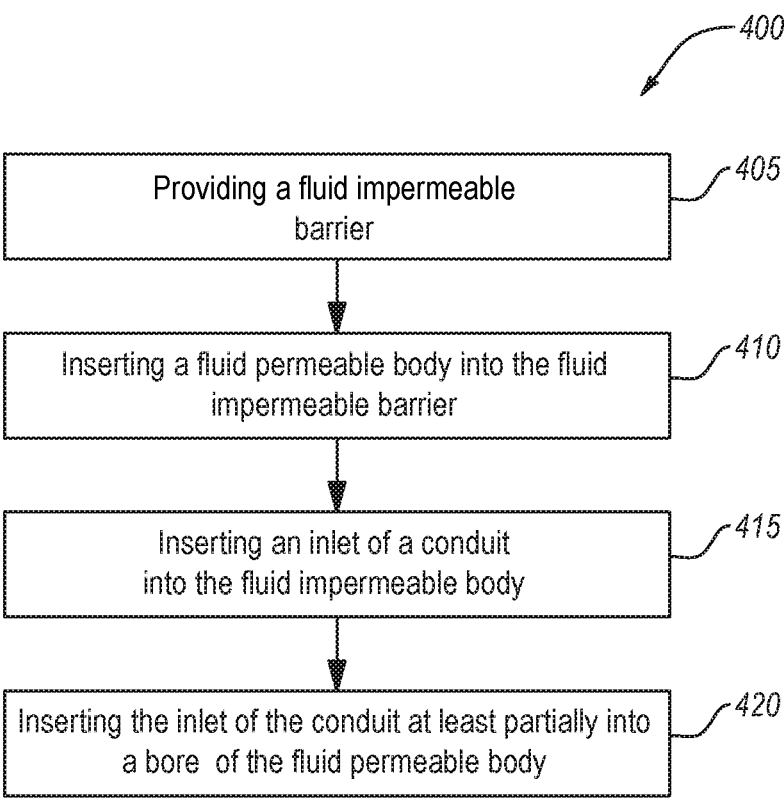
FIG. 4 is a flow diagram of a method of assembling a fluid collection device, according to an embodiment.

FIG. 4 is a flow diagram of a method 400 of assembling the fluid collection devices and/or fluid collection systems disclosed herein, according to an embodiment. The method 400 can include act 405, which recites providing a fluid impermeable barrier. The fluid impermeable barrier at least partially defines a chamber and also an opening extending therethrough. The opening is configured to be positioned adjacent to a female urethra or have a male urethra positioned therethrough. The fluid permeable body can include a singular porous hydrophilic polyolefin material extruded, molded, or sintered to a substantially cylindrical shape The method can include act 410, which recites inserting a substantially cylindrical and fluid permeable body into the chamber of the fluid impermeable barrier. When the fluid permeable body is inserted into the chamber of the fluid impermeable barrier, the fluid permeable body interfaces at least a portion of the fluid impermeable barrier and covers at least a portion of the opening. The fluid permeable body includes a singular porous material that is substantially cylindrical in shape and configured to wick any fluid away from the opening. In some embodiments, act 410 can include inserting the fluid permeable body into the chamber of the fluid impermeable barrier such that a reservoir is defined within the chamber by a second body end of the fluid permeable body distal to the first body end and a second end region of the fluid impermeable barrier distal to the aperture. In some embodiments, act 410 can include inserting the substantially cylindrical and fluid permeable body into the chamber of the fluid impermeable barrier such that the fluid permeable body and the conduit fill substantially all of the chamber.

The method can include act 415, which recites inserting an inlet of a conduit into the fluid impermeable body. The conduit can be inserted into the fluid impermeable body through an aperture defined by the fluid impermeable barrier at a first end region of the fluid impermeable barrier. In some embodiments, act 415 can include inserting the inlet of the conduit into the bore at the first body end, through the bore of the fluid permeable body, through the second body end of the fluid permeable body, and into the reservoir such that the conduit extends from the reservoir, through the fluid permeable body, through the aperture to outside the fluid impermeable barrier.

The method can include an act 420, which recites inserting the inlet of the conduit at least partially into a bore at a first body end of the fluid permeable body. The bore extends at least partially through the fluid permeable body and is defined by the fluid permeable body. The conduit interfaces at least a portion of the fluid permeable body.

Acts 405, 410, 415, and 420 of the method 400 are for illustrative purposes. For example, the act 405, 410, 415, and 420 of the method 400 can be performed in different orders, split into multiple acts, modified, supplemented, or combined. In an embodiment, one or more of the acts 405, 410, 415, and 420 of the method 400 can be omitted from the method 400. Any of the acts 405, 410, 415, and 420 can include using any of the fluid collection devices or systems disclosed herein.

Figure 5A:
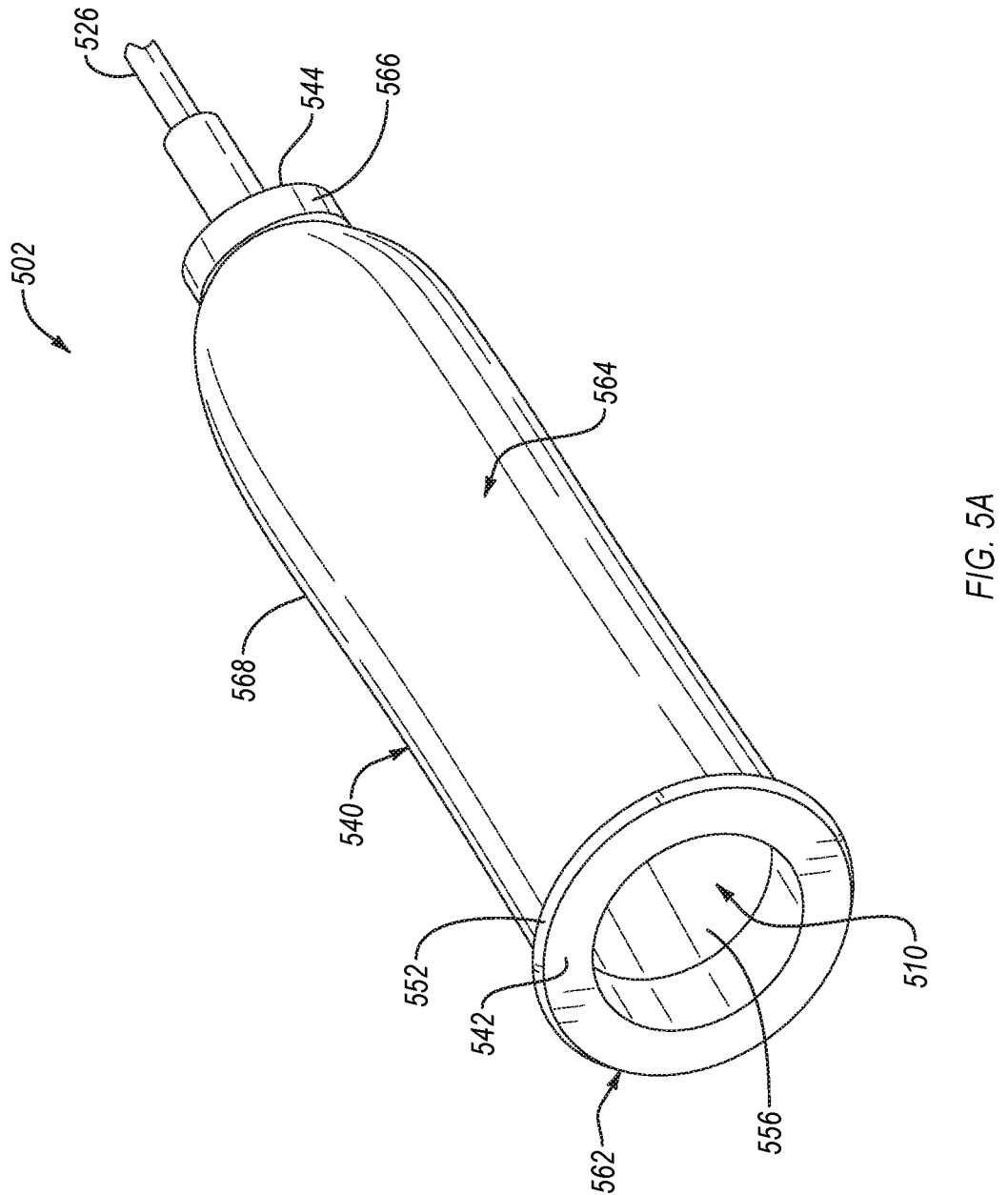
FIG. 5A is an isometric view of a urine collecting assembly, according to an embodiment.
Figure 5B:
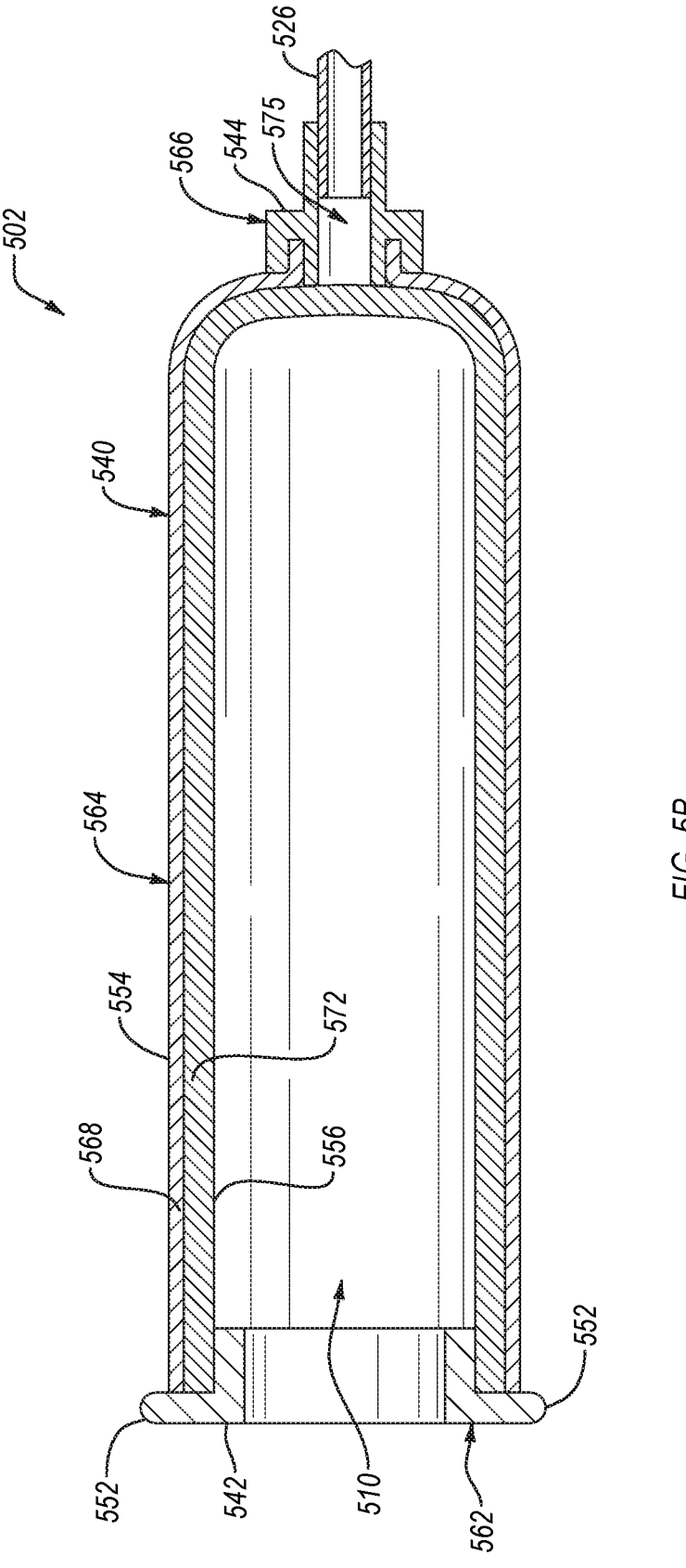
FIG. 5B is a schematic cross-sectional view of a urine collecting assembly, according to an embodiment.
Figure 5C:
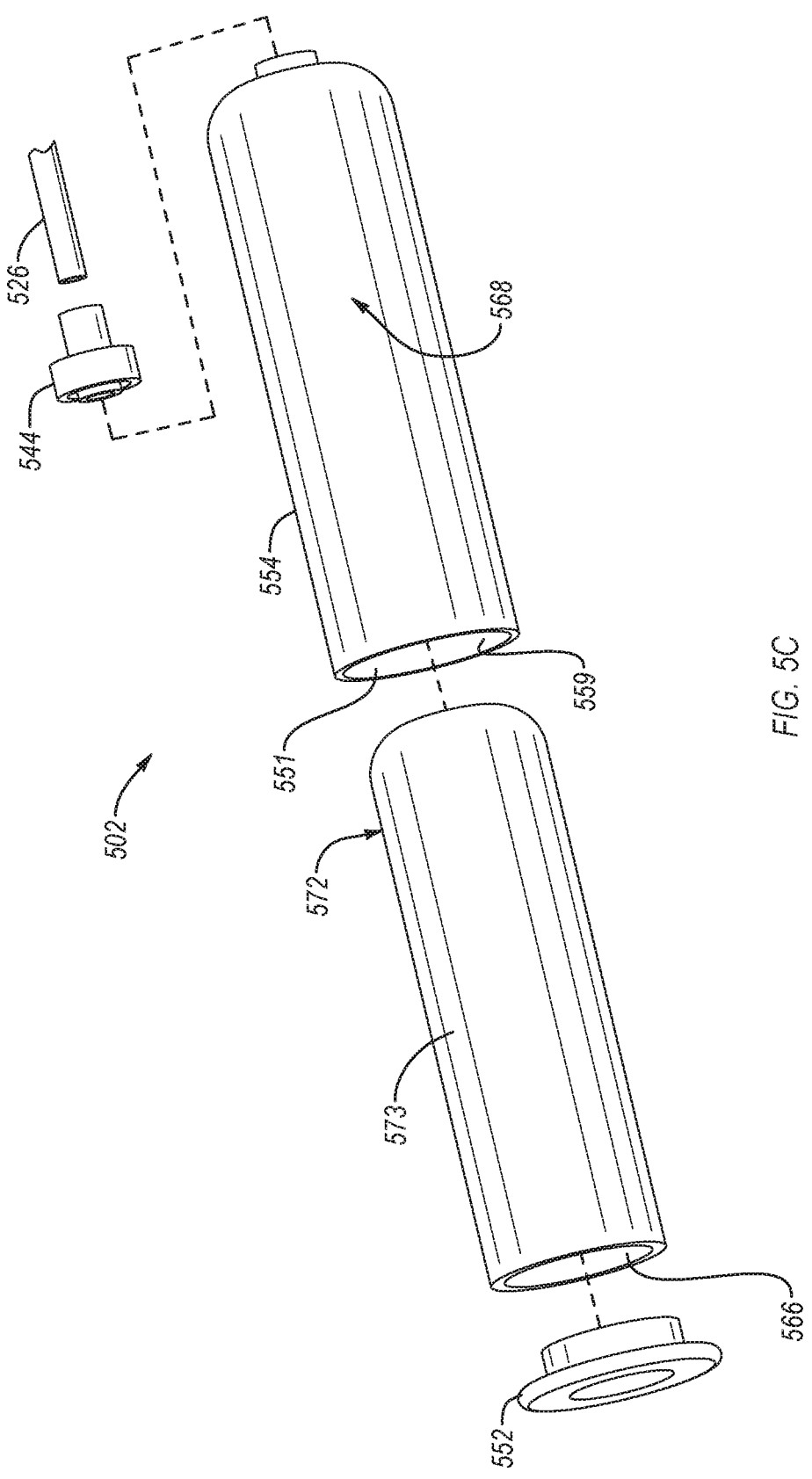
FIG. 5C is an exploded view of the urine collecting assembly of FIG. 5A, according to an embodiment.

Also disclosed herein is a fluid collection device 502 configured for use with a male user. FIGS. 5A and 5B are an isometric view and a schematic cross-sectional view, respectively, of a fluid collection device 502 (or urine collecting assembly), according to an embodiment. FIG. 5C is an exploded view of the fluid collection device 502. The fluid collection device 502 can include a body 540 having a first end 542 and a second end 544, an opening 510 at a first end of the body, a reservoir 575 at the second end 544 of the body 544, and tubing 526 (or conduit) providing fluid communication with the reservoir 575. The first end 542 may include an open proximal end and the second end 544 may include closed distal end.

The body 540 of the fluid collection device 502 can include a ring 562 at or near the first end 542 of the body 540, a sheath 564 extending from or near the first end 542 to or near the second end 544 of the body 540, and a sump 566 at the second end 544 of the body 540. The sheath 564 is configured to prevent a fluid (e.g., urine) escaping from the opening 510 and to move the fluid towards the reservoir 575 in the sump 566 and the tubing 526. As such, referring to FIG. 5B, the sheath 564 can include a plurality of layers that facilitate the operation of the sheath 564. For example, the sheath 564 can include a fluid impermeable layer 568, and a fluid permeable layer 572. The fluid impermeable layer 568 can form an external surface 554 of the body 540 and prevent the fluid from leaking through the sheath 564. The fluid permeable layer 572 can form an internal surface 556 of the body 540 at least partially defining the opening 510 within the sheath 564. The fluid impermeable layer 568 may be substantially cylindrical in shape.

The fluid permeable layer 572 can be configured to substantially prevent the fluid that is in the fluid permeable layer 572 from flowing back into the opening 510. As such, fluid permeable layer 572 can remove fluid from around a penis thereby leaving the penis dry. The fluid permeable layer 572 can include a one-way fluid movement fabric. The fluid permeable layer 572 can enable the fluid to flow generally towards the tubing 526. The fluid permeable layer 572 can include any material that can wick the fluid. For example, the fluid permeable layer 572 can include a porous or fibrous material, such as hydrophilic polyolefin. In some embodiments, the fluid permeable layer 572 consists of or consists essentially of a porous or fibrous material, such as hydrophilic polyolefin. Examples of polyolefin that can be used in the fluid permeable layer 572 include, but are not limited to, polyethylene, polypropylene, polyisobutylene, ethylene propylene rubber, ethylene propylene diene monomer, or combinations thereof. The fluid permeable layer 572 can include varying densities or dimensions. Moreover, the fluid permeable layer 572 can be manufactured according to various manufacturing methods, such as molding, extrusion, or sintering. The fluid permeable layer 572 may be substantially cylindrical in shape, and may fit within the fluid impermeable layer 568. In some embodiments, and majority of the outer surface 573 (shown in FIG. 5C) of the fluid permeable layer 572 interfaces with an inner surface 559 (shown in FIG. 5C) of the fluid impermeable layer 568.

The sheath 564 is configured to have a penis disposed therein. To facilitate fluid collection and improve comfort, the sheath 564 can be flexible thereby allowing the sheath 564 to correspond to the shape of a penis. For example, the flexible sheath 564 can at least partially collapse when the penis is flaccid and at least partially expand and bend to the shape of the penis as the penis becomes erect. Forming the layers of the sheath 564 from at least one of thin layers (e.g., less than 500 μm thick, and more particularly less than 250 μm thick, less than 100 μm thick, or less than 50 μm thick), flexible layers, or fabric can allow the sheath 564 to be sufficiently flexible.

The opening 510 is at least partially defined by the body 540 and extends from the first end 542 at least partially to the second end 544, thereby enabling a penis to enter the body 540. With a penis inserted into the opening 510 of the body 540, a male urethra is positioned within the fluid collection device 502 via the opening 510. The fluid collection device 502 is configured to receive the urine into the chamber 551 via the opening 510. For example, the opening 510 can exhibit an elongated shape that is configured to receive at least a portion of the penis, including the urethra. The opening 510 can exhibit an elongated shape to receive at least a portion of the penis, thereby only permitting the flow of the fluids along a path that corresponds to the elongated shape of the opening 510.

The ring 562 can be more rigid than the sheath 564. For example, the ring 562 can be formed from a flexible polymer that is at least one of thicker than the entire sheath 564 or exhibits a Young's modulus that is greater than sheath 564. As such, the ring 562 can provide some structure at or near the first end 542 of the body 540. The increased rigidity of the ring 562 can cause the first end 542 to remain open, thereby facilitating insertion of a penis into the urine collecting assembly 502. Further, in an embodiment, the increased rigidity of the ring 562 can enable the ring 562 to act as an attachment mechanism. For example, as illustrated, the ring 562 can include at least one protrusion 552 that extends from the rest of the body 540. In another example, the ring 562 can define a recess, include threads, or include any other attachment mechanism disclosed herein.

The sump 566 is configured to attach the rest of the urine collecting assembly 502 to the tubing 526. For example, the sump 566 can partially define an reservoir 575 extending through at least the fluid impermeable layer 568 thereby coupling the tubing 526 to the porous layer 572 and/or the opening 510. The tubing 526 can include an outlet and an inlet extending to or into the reservoir 575. Further, the sump 566 can close the second end 544 of the body 540. For example, the sump 566 can bunch up the sheath 542 and close any gaps that may form. The sump 566 can store fluids in the reservoir 575 therein. The reservoir 575 is an unoccupied portion of the sump 566 and is void of other material. In some embodiments, the reservoir 575 is defined at least partially by the fluid permeable layer 572 and the sump 566. During use, the fluids that are in the chamber 551 can flow through the fluid permeable layer 572 to the reservoir 575. The reservoir 575 can store at least some of the fluids therein and/or position the fluids for removal by the tubing 526. In some embodiments, at least a portion of the singular porous material of the fluid permeable layer 572 extends continuously between at least a portion of the opening 510 and the reservoir 575 to wick any fluid from the opening 510 directly to the reservoir 575.

The ring 562, the sheath 564, the sump 566, and the tubing 526 can be attached together using any suitable method. For example, at least two of the ring 562, the sheath 564, the sump 566, or the tubing 526 can be attached together using at least one of an interference fit, an adhesive, stitching, welding (e.g., ultrasonic welding), tape, any other suitable method, or combinations thereof.

Figure 6:
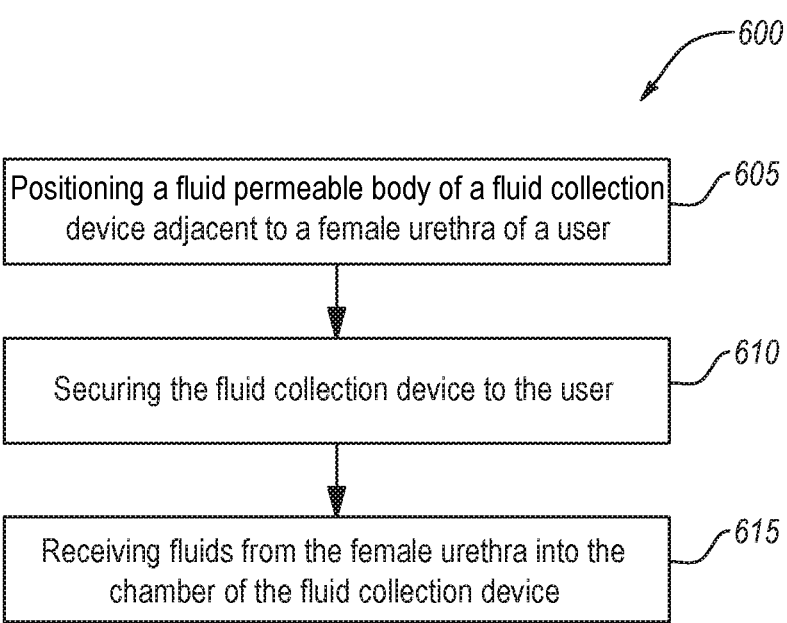
FIG. 6 is a flow diagram of a method to collect fluid, according to an embodiment.

FIG. 6 is a flow diagram of a method 600 for collecting fluids. The method 600 includes an act 605 of positioning a fluid permeable body of a fluid collection device adjacent to a female urethra of a user. The fluid permeable body is disposed within a chamber of a fluid impermeable barrier of the fluid collection device and exposed to the female urethra of the user through an opening in the fluid collection device defined by the fluid impermeable barrier. The method 600 also includes an act 610 of securing the fluid collection device to the user. The method 600 also includes an act 615 of receiving fluids from the female urethra into the chamber of the fluid collection device. In some embodiments, the method 600 an act of applying suction effective to suction the fluids from the chamber via a conduit disposed therein.

While various aspects and embodiments have been disclosed herein, other aspects and embodiments are contemplated. The various aspects and embodiment disclosed herein are for purposes of illustration and are not intended to be limiting.

I claim:

1. A fluid collection device, comprising:
   a fluid impermeable barrier at least partially defining a chamber, the fluid impermeable barrier including an opening extending therethrough, the opening configured to be positioned adjacent to or receive therein a urethra of a subject;
   a fluid permeable body that is extruded to form a singular fibrous material in a cylindrical shape defining a bore extending at least partially therethrough and positioned at least partially within the chamber, wherein the singular fibrous material consists essentially of a singular and fibrous polyolefin material;

a reservoir being at least partially defined by the fluid permeable body, wherein the fluid permeable body is configured to wick fluid away from the opening to the reservoir; and
   a conduit positioned at least partially within the bore and including an inlet and an outlet, the inlet being in fluid communication with the reservoir,
   wherein the singular fibrous material extends substantially continuously from the conduit to an outer surface of the fluid permeable body,
   wherein a portion of the outer surface of the fluid permeable body defines at least a portion of an outer surface of the fluid collection device, and the portion of the outer surface of the fluid collection device is free from coverage by gauze or other wicking material; and
   wherein a portion of the singular fibrous material of the fluid permeable body extends continuously between the opening and the reservoir to wick any fluid from the opening to the reservoir.

2. The fluid collection device of claim 1, wherein the fluid impermeable barrier defines the opening and the opening is configured to be placed adjacent to the urethra of a female subject.

3. The fluid collection device of claim 2, wherein:
   the fluid impermeable barrier defines an aperture at a first end region of the fluid impermeable barrier;
   the fluid permeable body extends across at least a portion of the opening;
   the conduit extends through the aperture into the fluid impermeable barrier and into the bore of the fluid permeable body at a first body end of the fluid permeable body, the aperture forming a fluid tight seal against the conduit extending therethrough; and
   the outlet of the conduit is positioned outside the fluid impermeable barrier.

4. The fluid collection device of claim 3, wherein the reservoir is defined by:
   a second body end of the fluid permeable body distal to the first body end; and
   a second end region of the fluid impermeable barrier distal to the aperture.

5. The fluid collection device of claim 4, wherein:
   the bore of the fluid permeable body extends through the fluid permeable body from the first body end to the second body end; and
   the conduit extends through the bore of the fluid permeable body into the reservoir such that the inlet of the conduit is positioned within the reservoir.

6. The fluid collection device of claim 1, wherein the fluid permeable body consists of polyolefin material.

7. The fluid collection device of claim 1, wherein:
   the fluid impermeable barrier includes an open proximal end and a closed distal end;
   the opening includes an elongated opening extending into the chamber from the open proximal end, the elongated opening being at least partially defined within the chamber by the fluid permeable body and being sized to dispose a penis of the subject therein; and
   the reservoir is positioned at the closed distal end.

* * * * *